United States Patent
Dorin et al.

(10) Patent No.: US 11,759,358 B2
(45) Date of Patent: Sep. 19, 2023

(54) LASER THERAPY FOR TREATMENT AND PREVENTION OF EYE DISEASES

(71) Applicant: ALEYEGN TECHNOLOGIES LLC, Saratoga, CA (US)

(72) Inventors: Giorgio Dorin, Cupertino, CA (US); John Randall Samples, Olympia, WA (US); Michael K. Ballard, Saratoga, CA (US); Satish Herekar, Palo Alto, CA (US); William Eddington, Sunnyvale, CA (US); Perry Binder, Hailey, ID (US)

(73) Assignee: ALeyeGN Technologies LLC, Saratoga, CA (US)

(*) Notice: Subject to any disclaimer, the term of this patent is extended or adjusted under 35 U.S.C. 154(b) by 0 days.

(21) Appl. No.: 17/290,969

(22) PCT Filed: Nov. 4, 2019

(86) PCT No.: PCT/US2019/059709
§ 371 (c)(1),
(2) Date: May 3, 2021

(87) PCT Pub. No.: WO2020/093060
PCT Pub. Date: May 7, 2020

(65) Prior Publication Data
US 2022/0031503 A1    Feb. 3, 2022

Related U.S. Application Data

(60) Provisional application No. 62/888,153, filed on Aug. 16, 2019, provisional application No. 62/755,298, filed on Nov. 2, 2018.

(51) Int. Cl.
*A61F 9/008* (2006.01)

(52) U.S. Cl.
CPC .... *A61F 9/008* (2013.01); *A61F 2009/00865* (2013.01); *A61F 2009/00868* (2013.01); (Continued)

(58) Field of Classification Search
CPC .. A61F 9/008; A61F 9/00802; A61F 9/00814; A61F 9/0084; A61F 2009/00844; (Continued)

(56) References Cited

U.S. PATENT DOCUMENTS

| 6,540,391 B2 | 4/2003 | Lanzetta et al. |
| 8,827,990 B2 | 9/2014 | Van Valen et al. |

(Continued)

FOREIGN PATENT DOCUMENTS

| CN | 104507427 | 4/2015 |
| EP | 3160379 | 5/2017 |

(Continued)

OTHER PUBLICATIONS

Acott et al., "Extracellular Matrix in the Trabecular Meshwork," *Exp. Eye Res.*, 86(4):543-561 (Apr. 2008).
(Continued)

*Primary Examiner* — Ahmed M Farah
(74) *Attorney, Agent, or Firm* — Klarquist Sparkman, LLP

(57) ABSTRACT

An ab externo automated laser treatment system for treating an eye in a subject, includes a non-contact laser source configured to generate a laser beam having at least one wavelength to treat the eye by directing the laser beam from a location spaced from the eye, wherein the at least one wavelength is a near-infrared wavelength in the range of about 0.5-2.2 μm, a laser scanner optically coupled to the non-contact laser source to receive the laser beam from the non-contact laser source and to scan the laser beam relative to the eye, and a processor, and memory including stored (Continued)

computer-readable instructions that, responsive to execution by the processor, cause the laser treatment system to direct the laser beam to a plurality of trans-scleral treatment locations to be irradiated in a predetermined treatment pattern on an external surface of the eye, wherein the trans-scleral treatment locations are 0-4 mm posterior to the corneolimbal junction, and wherein the laser beam is repetitively directed to the same irradiated trans-scleral treatment locations on the surface of the eye, and the trans-scleral treatment locations are irradiated at intervals sufficient to induce protective thermal preconditioning and therapeutic bio-stimulation of one or more of the trabecular meshwork and/or ciliary body without photocoagulation of the tissue of the eye. Trans-pupillary systems, patient interfaces, and methods are also disclosed.

41 Claims, 50 Drawing Sheets

(52) U.S. Cl.
CPC ............... *A61F 2009/00891* (2013.01); *A61F 2009/00897* (2013.01)

(58) Field of Classification Search
CPC .. A61F 2009/00851; A61F 2009/00861; A61F 2009/00865; A61F 2009/00868; A61F 2009/00872; A61F 2009/00891; A61F 2009/00897
USPC ................................. 606/3–4, 10–12, 17, 18
See application file for complete search history.

(56) References Cited

U.S. PATENT DOCUMENTS

| | | | |
|---|---|---|---|
| 8,995,618 B2* | 3/2015 | Gertner | A61B 6/506 378/68 |
| 9,962,291 B2 | 5/2018 | Luttrull et al. | |
| 10,285,859 B2 | 5/2019 | Luttrull et al. | |
| 2003/0078567 A1 | 4/2003 | Dorin et al. | |
| 2007/0129709 A1 | 6/2007 | Andersen et al. | |
| 2008/0319427 A1 | 12/2008 | Palanker | |
| 2010/0076419 A1 | 3/2010 | Chew et al. | |
| 2011/0282333 A1 | 11/2011 | Herekar et al. | |
| 2012/0116372 A1 | 5/2012 | Degani et al. | |
| 2013/0103011 A1 | 4/2013 | Grant et al. | |
| 2014/0243805 A1 | 8/2014 | Dick et al. | |
| 2015/0209179 A1* | 7/2015 | Chew | A61F 9/009 606/6 |
| 2015/0247199 A1 | 9/2015 | Fletcher et al. | |
| 2015/0283265 A1* | 10/2015 | Peyman | A61N 5/0622 424/491 |
| 2015/0366706 A1 | 12/2015 | Belkin et al. | |
| 2016/0067086 A1 | 3/2016 | Tedford et al. | |
| 2017/0087014 A1 | 3/2017 | Potter, Jr. et al. | |
| 2017/0112572 A1 | 4/2017 | Shazly et al. | |
| 2018/0207029 A1* | 7/2018 | Herekar | A61N 5/0625 |
| 2019/0151151 A1 | 5/2019 | Luttrull et al. | |
| 2020/0306080 A1* | 10/2020 | Herekar | A61F 9/00802 |

FOREIGN PATENT DOCUMENTS

| | | |
|---|---|---|
| JP | 2016-507321 | 3/2016 |
| JP | 2016-511118 | 4/2016 |
| WO | WO 2011/050056 | 4/2011 |
| WO | WO 2014/015061 | 1/2014 |
| WO | WO 2014/150601 | 9/2014 |
| WO | WO 2018/049246 | 3/2018 |

OTHER PUBLICATIONS

Acott et al., "Trabecular Repopulation by Anterior Trabecular Meshwork Cells After Laser Trabeculoplasty," *American Journal of Ophthalmology*, 107(1):1-6 (Jan. 1989).

Aquino et al., "External Micropulse Diode Laser Trabeculoplasty (EMDLT) for Primary Open Angle Glaucoma: A Pilot Study," *NUHS*, 1 page (2018).

Bylsma et al., "Laser trabeculoplasty renewed," Glaucoma Research 2018-2020, pp. 255-265, Amsterdam: Kugler Publications 2018.

Fea et al., "Laser Treatment of Glaucoma: Evolution of Laser Trabeculoplasty Techniques," *Techniques in Ophthalmology*, 6(2):45-52 (Jun. 2008).

Bradley et al., "Mediation of Laser Trabeculoplasty-Induced Matrix Metalloproteinase Expression by IL-1β and TNFα," *Investigative Ophthalmology & Visual Science*, 41(2):422-430 (Feb. 2000).

Dorin, "The 810 Nm I.R. Diode Laser in the pivotal paradigm shift from laser photocoagulation to laser photostimulation," *Glaucoma Research and Clinical Advances*, pp. 287-293 (Feb. 23, 2016).

Dorin et al., "Laser alteration of the collector channels ostia. Pivotal paradigm shift from laser photocoagulation to laser photostimulation," *Glaucoma Research and Clinical Advances*, pp. 283-288 (Jan. 2016).

Dueker et al., "Stimulation of Cell Division by Argon and Nd: YAG Laser Trabeculoplasty in Cynomolgus Monkeys," *Investigative Ophthalmology & Visual Science*, 31(1):115-124 (Jan. 1, 1990).

Kim et al., "Thermal Injury Induces Heat Shock Protein in the Optic Nerve Head in Vivo," *Investigative Ophthalmology & Visual Science*, 47(11):4888-4894 (Nov. 2006).

Lavinsky et al., "Nondamaging Retinal Laser Therapy: Rationale and Application to the Macula," *Investigative Ophthalmology & Visual Science*, 57(6):2488-2500 (May 2016).

Luttrull, "Improved retinal and visual function following panmacular subthreshold diode micropulse laser for retinitis pigmentosa," *The Royal College of Ophthalmologists*, https://doi.org/10.1038/s41433-018-0017-3, 12 pages (Feb. 16, 2018).

Luttrull et al., "Long-Term Safety, High-Resolution Imaging, and Tissue Temperature Modeling of Subvisible Diode Micropulse Photocoagulation for Retinovascular Macular Edema," *Retina*, 32(2):375-386 (Feb. 2012).

Luttrull et al., "Panmacular subthreshold diode micropulse laser (SDM) as neuroprotective therapy in primary open-angle glaucoma," *Glaucoma Research*, pp. 277-290 (Apr. 15, 2018).

Ma et al., "Neuroprotective effect on retinal ganglion cells by transpupillary laser irradiation of the optic nerve head," *Neuroscience Letters*, 476:3-8 (Jan. 4, 2010).

Paulus et al., "Selective Retinal Therapy with Microsecond Exposures Using a Continuous Line Scanning Laser," Retina, 31(2):380-388 (Oct. 2010).

Examination Report for related European Application No. 19809343.7, 5 pages, dated Jul. 27, 2021.

Communication under Rule 71(3) for related European Application No. 19809343.7, 129 pages, dated Feb. 9, 2022.

Communication under Rule 71(3) for related European Application No. 19809343.7, 128 pages, dated Jun. 14, 2022.

Bylsma et al., "Trabecular Cell Division After Argon Laser Trabeculoplasty," *Archives of ophthalmology*, 106(4): 544-547 (Apr. 1988).

Van Buskirk et al., "Argon Laser Trabeculoplasty: Studies of Mechanism of Action," *Ophthalmology*, 91(9): 1005-1010 (Sep. 1984).

Examination Report (w/ Eng. translation) for related IN App. No. 202117024518, dated Jan. 12, 2023, 2022, 8 pages.

Japanese Office Action (w/ Eng. translation) for related JP App. No. 2021-523889, dated Aug. 18, 2022, 5 pages.

\* cited by examiner

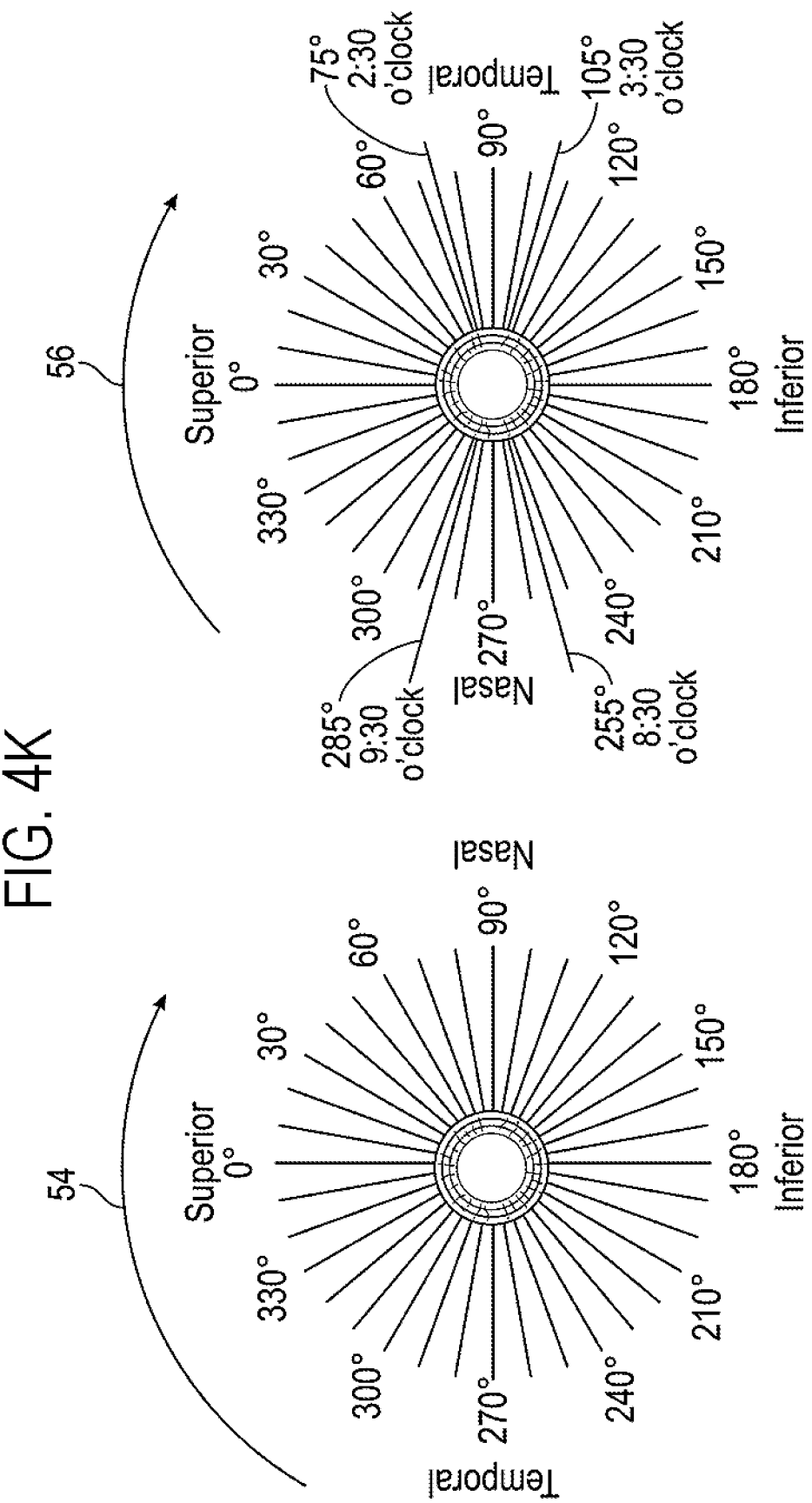

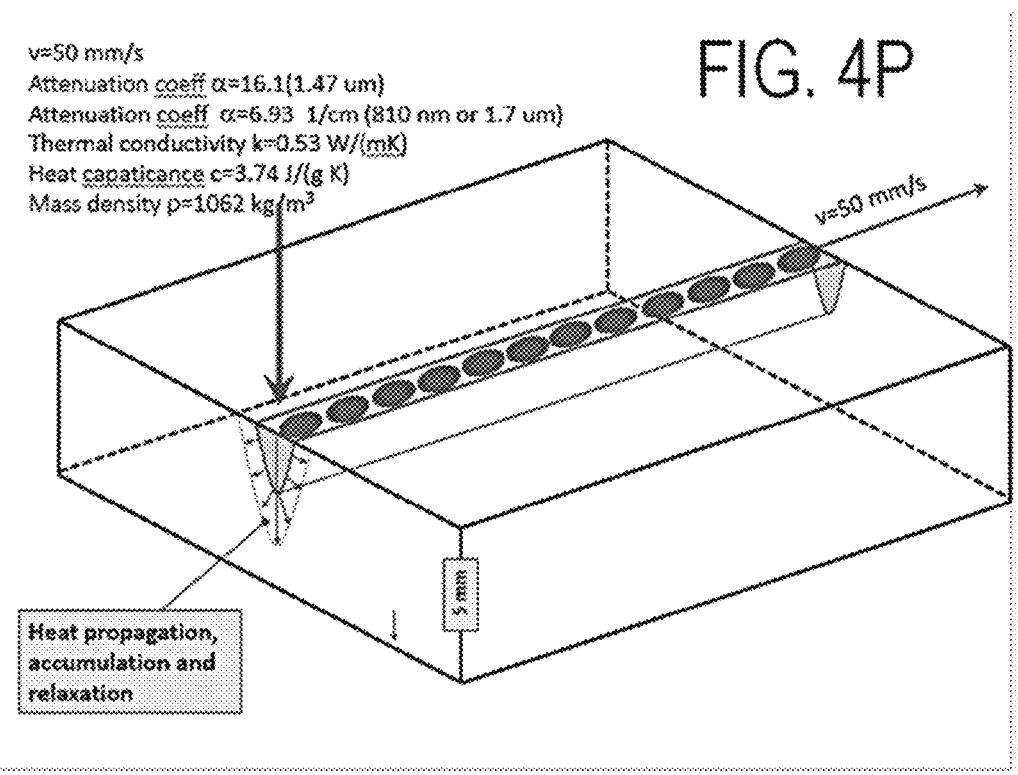
FIG. 4P
FIG. 4Q
5 scans every 0.4s, 1W, 50 mm/s, 1.47 micron
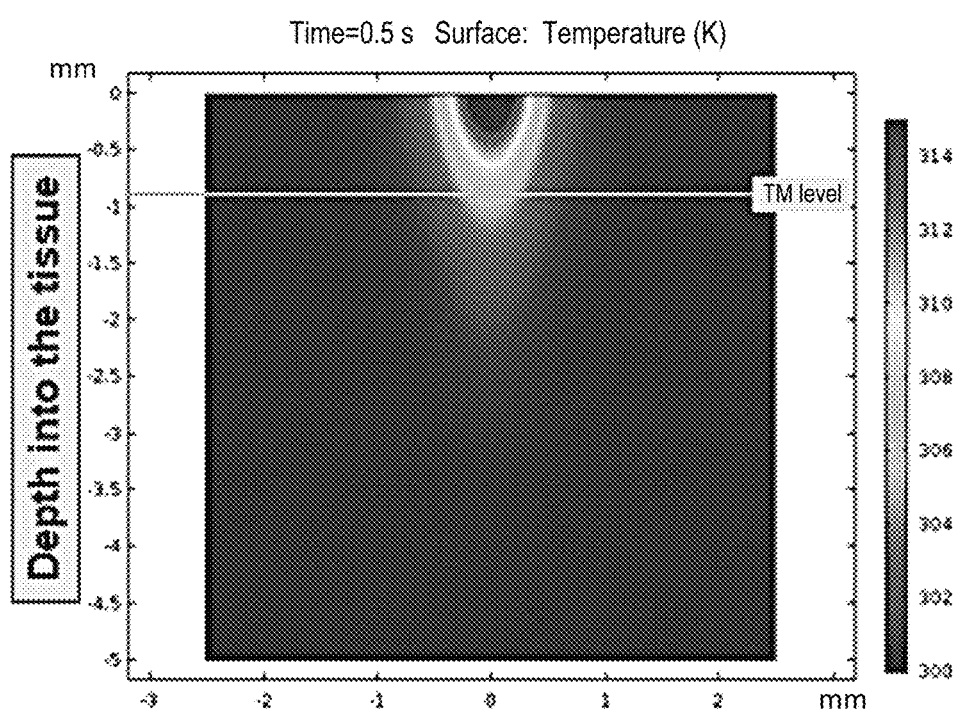

Time=4.88 s   Surface: Temperature (K)

FIG. 4Y   Speed affects peak temperature 0.8 W 50-25-10-5 mm/sec Arc 200 deg DC 3.44%

Duty Cycle Affects Peak Temperature 0.8 W, 50-25-10-5 mm/sec, Arc 60 deg, Duty cycle 11.5%

0.8 W, 50-25-10-5 mm/sec, Arc 4 deg, Duty cycle 172%

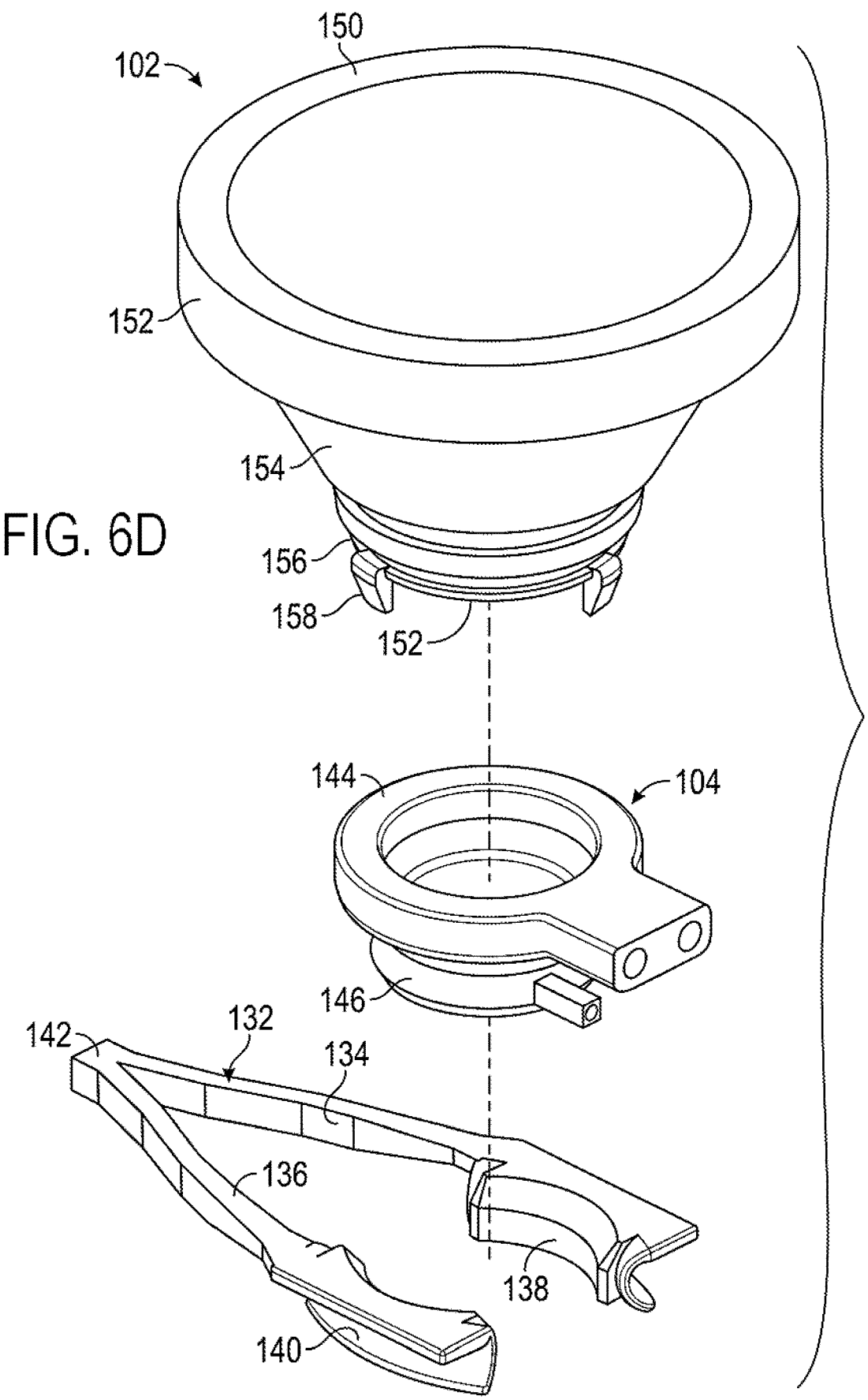

LASER THERAPY FOR TREATMENT AND PREVENTION OF EYE DISEASES

CROSS REFERENCE TO RELATED APPLICATIONS

This is the U.S. National Stage of International Application No. PCT/US2019/059709, filed Nov. 4, 2019, which was published in English under PCT Article 21(2), which in turn claims the benefit of U.S. Provisional Application No. 62/755,298, filed Nov. 2, 2018 and U.S. Provisional Application 62/888,153 filed Aug. 16, 2019, each of which is incorporated by reference in its entirety.

FIELD

Trans-scleral ab externo IOP lowering and trans-pupillary neuroprotection laser treatments are disclosed for the clinical management of patients with ocular hypertension and/or glaucoma and for the treatment and/or prevention of related diseases.

BACKGROUND

Glaucoma is an optic neuropathy characterized by increased intraocular pressure (IOP) that damages the retina ganglion cells and the nerve fibers in the optic disc. Aqueous humor is produced from the ciliary processes, moves through the pupil then into the anterior chamber and through the trabecular meshwork, Schlemm's canal, and uveoscleral outflow pathways. Increased IOP results from an imbalance between the production of aqueous humor and resistance to its outflow through the normal outflow tracts. Glaucoma can lead to chronic, progressive deterioration of the optic nerve that results in cupping and atrophy of the optic disc. The nerve damage causes a progressive loss of the peripheral visual field followed by a loss of central vision and irreversible blindness if not timely treated. The goal of current glaucoma treatments is to stop or slow disease progression by reducing IOP, which has been the only known modifiable risk factor. The most common treatment for glaucoma is the life-long use of IOP-lowering medication, such as eye drops containing prostaglandin analogs, beta-adrenergic receptor antagonists, alpha2-adrenergic agonists, and miotic agents. Although these medications have improved the treatment of glaucoma, they have local and systemic side-effects. Patient adherence to medication protocols is also unpredictable and life-long use of the medication can be expensive. Poor compliance with medication use is a major cause of vision loss in glaucoma patients.

Glaucoma surgeries, such as trabeculotomies and tube shunts with antifibrotics, avoid some of these problems. Laser-based therapies, such as Laser Trabeculoplasty (LT) and Laser Cyclophotocoagulation, have been performed to lower IOP, the former by increasing aqueous humor (AH) outflow and the latter by decreasing its production. Argon laser trabeculoplasty (ALT) uses a gonioscopic lens applied to the eye to deflect a laser beam through the cornea and into the angle of the anterior chamber of the eye to directly irradiate the trabecular meshwork. ALT was the first type of LT introduced in the 1970s and it has subsequently been practiced using a variety of lasers, wavelengths, and treatment techniques. Some of these techniques are Diode Laser Trabeculoplasty (DLT), Selective Laser Trabeculoplasty (SLT), Micropulse Laser Trabeculoplasty (MLT), and Titanium-Sapphire Laser Trabeculoplasty (TLT).

However, LT is normally an ab interno procedure that is performed trans-corneally using a slit-lamp delivery system and a corneal contact goniolens to visualize and precisely direct the laser beam into the anterior angle of the eye, below the Schwalbe Line (SL), to the pigmented trabecular meshwork where the laser energy is absorbed and converted into heat. Laser wavelengths in the 488-810 nm range have been used for these procedures to specifically interact with the darkly pigmented cells in the TM. Trans-corneal LT procedures are challenging and contact between the gonioscopy lens and the eye can induce iatrogenic corneal lesions such as punctate keratopathies and infections.

LT has also been performed ab externo using a trans-scleral approach with a 532 nm SLT frequency-doubled Q-switched 3-ns Nd:YAG laser beam (Geffen et al., J. Glaucoma 26:201-207, 2017) or a 810 nm MDLT micropulsed laser beam (see Aquino M C and Chew P K, External Micropulse Diode Laser Trabeculoplasty (EMDLT) for Primary Open Angle Glaucoma: a pilot study. P4-097 European Glaucoma Society 2018 Annual Congress, Firenze, Italy; and U.S. Pat. No. 8,945,103). The SLT or the EMDLT laser beam is applied ab-externo over the perilimbal area through the corneoscleral junction to affect the conventional outflow pathway structures (collector channels, Schlemm's canal, juxtacanalicular, corneoscleral and uveal TM). Trans-scleral procedures have generally not used infrared wavelengths that are known to be absorbed by water in the superficial scleral cells because superficial absorption would prevent the laser energy from reaching the targeted deeper structures, such as the trabecular meshwork. U.S. Pat. No. 6,319,274 uses longer wavelength laser energy directed trans-sclerally from a probe that indents the surface of the eye to facilitate the laser energy penetration through the thickness of the sclera (750-950 µm) to reach the trabecular meshwork.

Hand guidance of a physical probe against the eye irritates the ocular surface and produces variable operator-dependent outcomes. Scleral indentation can also induce intraocular pressure spikes and cause glaucomatous damage to the eye. Laser energy in the probe-conjunctiva interface can cause contact burns, and the probe that touches the eye is a potential infectious disease vector. Despite these problems a scleral indentation probe has generally been considered necessary to maximize laser energy penetration deep into the sclera. Scleral indentation moves the laser energy source closer to the deep scleral targets and expresses water from underlying scleral cells to reduce both absorption and scattering of the light energy by water molecules in the superficial sclera. Manual movement of the laser probe against the eye, however, limits the laser movement speed because fast movements abrade or otherwise traumatize the eye being treated. Furthermore, in manual movement, the speed and the positioning of the laser probe cannot be precisely controlled by the surgeon in a consistent manner resulting in practically unrepeatable and grossly variable laser energy deposition in each treatment.

Lowering and controlling IOP has been and remains a major goal in the management of glaucomatous patients. Unfortunately, even when IOP is successfully controlled, almost 60% of glaucoma patients experience progression of visual field loss due to continued neurodegenerative process with loss of retinal ganglion cells and thinning of papillary nerve fiber axons.

Optical coherence tomography angiography (OCTA) has facilitated the detection of areas of retinal capillary hypoperfusion in patients with chronic progressive neurotrophic neurodegenerative retinopathies including age-related macular degeneration (AMD), diabetic retinopathy (DR), retinitis pigmentosa (RP), and in patients with POAG. Glaucoma has been associated with reduced blood perfusion in the retina, and the presence of capillary hypo-perfusion correlates to later measures of nerve fiber thinning and visual field defect progression. The concern that IOP lowering treatments alone may not be sufficient to prevent visual loss progression has led to increased interest in neuroprotective treatments to improve the neurotrophic balance, thus the health and function of the optic nerve and retina. For example, U.S. Pat. No. 9,962,291 discloses the use of subthreshold photocoagulation of the retina, in the pattern of a grid or rotated line. However, a need remains for improved systems and methods for treating glaucoma by reducing/controlling IOP and by administering an effective neuroprotective therapy to slow, stop, and possibly reverse the neurodegenerative progression.

SUMMARY

A laser beam that irradiates an eye structure is moved rapidly in a periodic cycle, such as a circular motion, to heat targeted eye tissue. The temperature of the targeted tissue increases during irradiation, then decreases during the remaining interval of the cycle until the tissue is again irradiated in the next cycle. The rapidly moving laser beam can be directed to different locations on or in the eye, for example by using contact lenses of different refractive indices. The wavelength of the laser may also be selected to improve laser energy delivery to the targeted eye structure. A laser beam can be directed trans-sclerally and/or trans-pupillary, and the wavelength of the laser beam can be different for different targeted eye structures. Trans-pupillary beams can be scanned continuously at selected scan speeds while delivering continuous-wave and/or pulsed laser energy to treatment location patterns. Examples can irradiate a laser beam in the absence of specific glaucoma indicators, so as to provide a preventative treatment for various eye diseases.

In an example, a trans-scleral IOP-lowering laser treatment is performed without a laser probe contacting the eye. The laser beam does not directly irradiate deep scleral and sub-scleral target structures such as the trabecular meshwork or the ciliary processes, but instead indirectly thermally stimulates them with heat generated by absorption of laser energy in more superficial layers of the eye. The laser beam is projected over the eye and moved rapidly to induce thermal waves that are propagated from surface structures to the targeted sub-scleral or intraocular structures. Rapid laser movement repeatedly irradiates the same treatment locations on the sclera at spaced intervals during sequential cycles of treatment. For example, the laser may move in a cycle through 360° and repeatedly return to a prior treatment location in subsequent cycles to irradiate that same treatment location during the subsequent cycle(s). In some examples the laser irradiates the scleral surface continuously or at spaced locations around the 360° path to induce a thermal wave in the tissue below the surface of the sclera throughout the path of irradiation. The thermal wave propagates by conduction through sub-scleral tissue three-dimensionally 360° to reach targeted sub-scleral structures (such as the trabecular meshwork, the ciliary body, and/or other targets of aqueous production and outflow) without direct laser irradiation.

A patient interface docked to the eye may hold the laser emission source at a position spaced from the eye. The laser wavelength may be in the range that targets selected tissue, for example that penetrates the scleral surface and interacts with cellular water of the superficial sclera. In some embodiments the wavelength may be a near-infrared wavelength of 0.8-2.2 µm or 1-2.2 µm, such as 1.0 to 1.7 µm, for example a wavelength of about 0.80-0.85 µm or a wavelength of about 1.4-1.6 µm. In some disclosed embodiments the wavelength is 1.47 µm. The laser energy heats the superficial sclera (for example to a depth of 100-700 µm, such as 100-200 µm, 100-550 µm or 100-500 µm) at a treatment location for a brief period without directly reaching and being absorbed by the deeper scleral structures (such as structures deeper than 700 µm). These deeper structures that are not directly irradiated and/or heated include the trabecular meshwork, the uveoscleral outflow network, the collector channels and/or ostia, and/or the ciliary body.

Superficial scleral heating is followed by a period of thermal relaxation during which heat conducts deeper into the sclera toward the trabecular meshwork and/or ciliary body. Cycles of repeated heating and thermal relaxation are intended to achieve protective thermal preconditioning, hyperthermia and therapeutic bio-stimulation of the intended target(s) such as the trabecular meshwork, the uveoscleral outflow network, and/or the ciliary body. In disclosed examples the cycles of repeated heating are specifically targeted to the same location on the scleral surface by an imaging system that repetitively targets the same treatment location throughout multiple cycles of heating, thermal relaxation, and heat wave propagation to the deeper target tissues. The treatment locations may be 0-4 mm (for example 1-4 mm) posterior to the corneolimbal junction.

Methods of precisely delivering a pre-programmed pattern of laser energy while cooling the surface of the eye are described, as are methods of lowering IOP, for example by carrying out any of the steps performed by the system.

According to an aspect of the disclosed technology, ab externo automated laser treatment systems for treating an eye in a subject, comprise a non-contact laser source configured to generate a laser beam having at least one wavelength to treat the eye by directing the laser beam from a location spaced from the eye, wherein the at least one wavelength is a near-infrared wavelength in the range of about 0.5-2.2 µm, a laser scanner optically coupled to the non-contact laser source to receive the laser beam from the non-contact laser source and to scan the laser beam relative to the eye, and a processor, and memory including stored computer-readable instructions that, responsive to execution by the processor, cause the laser treatment system to direct the laser beam to a plurality of trans-scleral treatment locations to be irradiated in a predetermined treatment pattern on an external surface of the eye, wherein the trans-scleral treatment locations are 0-4 mm posterior to the corneolimbal junction, and wherein the laser beam is repetitively directed to the same irradiated trans-scleral treatment locations on the surface of the eye, and the trans-scleral treatment locations are irradiated at intervals sufficient to induce protective thermal preconditioning and therapeutic bio-stimulation of one or more of the trabecular meshwork and/or ciliary body without photocoagulation of the tissue of the eye.

In some examples, memory includes stored computer-readable instructions that cause the laser treatment system to direct the laser beam to a plurality of trans-pupillary treatment locations and to induce sublethal thermal elevations eliciting therapeutic biomodulation at the target eye tissue within a predetermined therapeutic temperature range, the plurality of trans-pupillary treatment locations including various singular or combinations of (a) a predetermined curvilinear treatment pattern on target eye tissue of the eye comprising multiple concentric annuli on the macula around but not on the foveal avascular zone, (b) an area (i) surrounding the macula, but not on the foveal avascular zone, and (ii) surrounding the optic disk, but not on the optic disk or adjacent peripapillary crescent, (c) an area surrounding the optic disk, but not on the optic disk or adjacent peripapillary crescent, or (d) an area adjacent to the foveal avascular zone, but not on the area of the papillomacular bundle.

In some examples, stored computer-readable instructions cause the laser treatment system to direct the laser beam to the plurality of trans-scleral and/or trans-pupillary treatment locations with the subject having clinically normal intraocular pressure and/or having an absence of glaucoma symptoms or diagnosis.

In selected examples, stored computer-readable instructions cause the laser treatment system to direct the laser beam to the plurality of trans-scleral treatment locations at the intervals sufficient to induce the protective thermal preconditioning and bio-stimulation of targeted structures eliciting biomechanical and biochemical responses to lower intraocular pressure of the eye of the subject. In some examples, the processor is configured with instructions to repetitively deliver the laser beam to the plurality of irradiated trans-scleral treatment locations at intervals that target an increase in the temperature of the outer 200-500 µm scleral layers to a temperature of about 45-57° C. Examples can include laser parameters configured to provide irradiance of the laser beam and a scanning speed with which the laser beam moves around the predetermined treatment pattern increases the temperature of the outer 200 µm scleral layers to the temperature of about 43-57° C., optionally about 43-45° C.

In some examples, the processor is configured with instructions to receive an input corresponding to a location of the corneolimbal junction or limbus of the subject and wherein the processor is configured to determine the plurality of trans-scleral treatment locations in response to the input and wherein the plurality of trans-scleral treatment locations is offset radially outward from the input location corresponding to corneolimbal junction or limbus to contour the treatment pattern to the anatomy of the eye of the subject. In some examples, the trans-scleral treatment locations are in a 360° annular pattern posterior to the corneolimbal junction, and the processor is configured to direct the laser beam to a set of pre-identified trans-scleral treatment locations on the surface of the eye during a first treatment cycle, and during a subsequent treatment cycle direct the laser beam to the same pre-identified trans-scleral treatment locations, to achieve precise cyclic thermal elevation of scleral tissue underlying the pre-identified trans-scleral treatment locations at intervals of time with thermal relaxation of the irradiated tissue between treatment cycles. In some examples, the processor is configured to set the speed of each treatment cycle to achieve the thermal relaxation by spacing irradiation of the trans-scleral treatment locations at sufficient intervals that an exposure time and relaxation time produce a targeted time-temperature history. In some examples, the interval between irradiation of the same trans-scleral treatment location produces a duty factor, corresponding to the ratio between the active exposure ON time/(active exposure+relaxation OFF time), in the 2-50% range. Example intervals between irradiation of the same trans-scleral treatment location can be about 10-300 ms, optionally about 100-200 ms. In some examples, the predetermined treatment pattern is located about 1.5 mm posterior to the corneolimbal junction. In particular examples, the predetermined treatment pattern comprises multiple annular treatment patterns, and wherein the multiple annular treatment patterns are spaced about 1.5 mm, 2.5 mm and 3.5 mm posterior to the corneolimbal junction, wherein the annular treatment patterns comprise one or more of circular, oval, elliptical, egg-like, non-circular, non-elliptical, or asymmetrical patterns, or patterns that correspond to the shape of Schlemm's canal or the limbus. In further examples, the 360° pattern is interrupted nasally by 10-30° and temporally by 10-30°. In some examples, the multiple annular treatment patterns target the perilimbal outflow structure, pars plicata, and pars plana.

Some examples further include a heat sink placed in contact with the eye over the trans-scleral treatment locations to conduct heat away from the surface of the eye. In some examples, the heat sink comprises a curved contact lens placed on the surface of the eye. In some examples, the contact lens comprises a cooled contact lens that substantially conforms to the surface of the eye. In examples, the laser beam has a near-infrared wavelength of 0.8-2.2 µm, optionally including a wavelength of 1-2.2 µm, 1.0-1.7 µm, 0.80-0.85 µm, 1.4-1.6 µm, and/or 1.47 µm. In some examples, the laser beam has a near-infrared wavelength of about 1.4-1.5 µm, optionally at 1.47 µm. In some examples, the protective thermal preconditioning and therapeutic bio-stimulation are controlled by one or more of the laser's power, irradiance, scanning speed, cycle repetition rate, number of cycle repetitions, spot size, and duty cycle. In some examples, the processor is configured to direct the laser beam to the trans-scleral treatment location in a spot having a diameter of 500-1000 µm, optionally about 600 µm. Some examples further include an optical imaging system for detecting the limbus and/or corneolimbal junction of the subject. In some examples, the processor is configured to identify the predetermined trans-scleral treatment locations at locations determined by the shape of the limbus and/or corneolimbal junction of the eye of the subject.

Some examples further include a patient interface for docking the non-contact laser source spaced away from the eye, the patient interface comprising a spacer that maintains the eye in a substantially fixed location for imaging and treatment, and the spacer maintains the non-contact laser source spaced from and not contacting the surface of the eye. In some examples, the patient interface further comprises a speculum for placement between the eyelids of the subject to expose the eye to the laser beam. In further examples, the patient interface further comprises a fixation ring for a contact lens, and the fixation ring comprises a resilient sealing face, wherein the system is configured to maintain negative pressure between the contact lens and the fixation ring to secure the patient interface to the surface of the eye and substantially immobilize the eye of the subject. In some examples, the negative pressure is adjustable. In further examples, the system is configured to cool the spacer and/or fixation ring and/or contact lens. In some examples, the spacer and/or fixation ring comprise internal fluid flow channels, and the system is configured to introduce a cooled fluid through the fluid flow channels to cool the spacer and/or fixation ring and/or contact lens. Some examples further include a positioning arm for positioning the patient interface in a location relative to the surface of the eye of the subject.

In some examples, each annulus on the macula of the curvilinear treatment pattern comprises a plurality of evenly-spaced and overlapping laser pulse spots sequentially delivered along a complete circle to produce an irradiated annular treatment zone within each annulus, wherein the laser pulse spots are delivered at a common scan speed for all macular annuli. In some examples, the multiple concentric annuli comprise radially contiguous irradiated annular treatment zones on the macula. In some examples, each concentric annulus has a width of between 400 μm and 600 μm. In various examples, the laser source is configured to produce the laser beam with pulses at a pulse repetition period in the range of 1-3 ms, pulse repetition rate of 1000 to 333 pulses per second and a pulse duration in the range of 20-500 μs. In some examples, the laser source is configured to produce the laser beam with pulses at a pulse repetition period in the range of 1.5-2.5 ms, pulse repetition rate of 666 to 400 pulses per second, and a pulse duration in the range of 50-150 μs. In selected examples, the laser source is configured to produce the laser beam with pulses at a pulse repetition period in the range of 1.8-2.2 ms, pulse repetition rate of 556 to 455 pulses per second, and a pulse duration in the range of 80-120 μs. In some examples, the annuli comprise three to five contiguous concentric annuli on the macula, each annulus having a substantially equal width, and wherein the plurality of trans-scleral treatment locations comprises three concentric annuli on the sclera around the limbus at radii $R_1$, $R_2$ and $R_3$ that correspond respectively to locations overlying the primary aqueous outflow pathway, the pars plicata ciliary body, and the pars plana. In some examples, annuli comprise five contiguous annuli on the sclera, each annulus having a width of approximately 500 microns, and wherein the plurality of trans-scleral treatment locations comprises three concentric annuli on the sclera at distances of approximately 1.5, 2.5, and 3.5 mm from the corneoscleral junction. In some examples, the sublethal thermal elevations correspond to a raise in the temperature of the target tissue in the annuli on the macula to a temperature of no more than 47° C., and the laser beam raises the temperature of the target tissue in the trans-scleral treatment locations to no more than 57° C.

In some examples, the laser source comprises a first diode laser source operable to produce a pulsed laser beam at 810 nm for directing to the trans-pupillary treatment locations, a second diode laser source operable to produce a continuous-wave laser beam at 1475 nm for directing to the trans-scleral treatment locations, and at least one beam splitter situated to receive and direct the beam at 810 nm and the beam at 1475 nm along a common optical path for receiving by the laser scanner. Some examples further include a detector optically coupled to the target eye tissue and wherein stored computer-readable instructions cause the laser scanner to selectively direct the laser beam to the target eye location based on a change in a position of the target eye tissue detected with the detector.

According to another aspect of the disclosed technology, ab externo automated methods for treating an eye in a subject, include directing laser energy having a near-infrared wavelength of about 0.5-2.2 μm from a location spaced from the eye to a plurality of trans-scleral treatment locations to be irradiated in a predetermined treatment pattern on an external surface of the eye, wherein the trans-scleral treatment locations are 0-4 mm posterior to the corneolimbal junction, and wherein the laser energy is repetitively directed to the same irradiated trans-scleral treatment locations on the surface of the eye, and the trans-scleral treatment locations are irradiated at intervals sufficient to induce protective thermal preconditioning and therapeutic bio-stimulation of one or more of the trabecular meshwork and/or ciliary body without photocoagulation of the tissue of the eye.

Some examples further include directing laser energy having a near-infrared wavelength of about 0.5-2.2 μm from the location spaced from the eye to a plurality of trans-pupillary treatment locations to induce sublethal thermal elevations eliciting therapeutic biomodulation at the target eye tissue within a predetermined therapeutic temperature range, the plurality of trans-pupillary treatment locations including various singular or combinations of (a) a predetermined curvilinear treatment pattern on target eye tissue of the eye comprising multiple concentric annuli on the macula around but not on the foveal avascular zone, (b) an area (i) surrounding the macula, but not on the foveal avascular zone, and (ii) surrounding the optic disk, but not on the optic disk or adjacent peripapillary crescent, (c) an area surrounding the optic disk, but not on the optic disk or adjacent peripapillary crescent, or (d) an area adjacent to the foveal avascular zone, but not on the area of the papillomacular bundle.

In some examples, the directing of the laser energy to the plurality of trans-scleral and/or trans-pupillary treatment locations is performed based on the subject having clinically normal intraocular pressure and/or having an absence of glaucoma symptoms or diagnosis.

In some examples, the directing the laser energy to the plurality of trans-scleral treatment locations at the intervals sufficient to induce the protective thermal preconditioning and bio-stimulation of targeted structures eliciting biomechanical and biochemical responses is configured to lower intraocular pressure of the eye. In some examples, repetitively delivering the energy to the plurality of irradiated trans-scleral treatment locations comprises delivering the energy at intervals that target an increase in the temperature of the outer 200-500 μm scleral layers to a temperature of about 45-57° C. In some examples, the directing the laser energy includes at a selected irradiance and scanning speed that increases the temperature of the outer 200 μm scleral layers to the temperature of about 43-57° C., optionally about 43-45° C.

In some examples, the plurality of trans-scleral treatment locations are offset radially outward a substantially uniform distance from the corneolimbal junction or limbus to contour the treatment pattern to the anatomy of the eye of the subject. In some examples, the trans-scleral treatment locations are in a 360° annular pattern posterior to the corneolimbal junction, and the laser energy is directed to a set of pre-identified trans-scleral treatment locations on the surface of the eye during a first treatment cycle, and during a subsequent treatment cycle the laser energy is directed to the same pre-identified trans-scleral treatment locations, to achieve precise cyclic thermal elevation of scleral tissue underlying the pre-identified trans-scleral treatment locations at intervals of time with thermal relaxation of the irradiated tissue between treatment cycles. In some examples, each treatment cycle is performed during a duration that achieves the thermal relaxation by spacing irradiation of the trans-scleral treatment locations at sufficient intervals that an exposure time and relaxation time produce a targeted time-temperature history. In some examples, the same trans-scleral treatment location is irradiated at intervals that produce a duty factor, corresponding to the ratio between the active exposure ON time/(active exposure+relaxation OFF time), in the 2-50% range. In some examples, the same trans-scleral treatment location is irradiated at intervals of about 10-300 ms, optionally about 100-200 ms. In some examples, the predetermined treatment pattern to which the laser energy is directed is located about 1.5 mm posterior to the corneolimbal junction. In some examples, the predetermined treatment pattern to which the laser energy is directed comprises multiple annular treatment patterns, and wherein the multiple annular treatment patterns are spaced about 1.5 mm, 2.5 mm and 3.5 mm posterior to the corneolimbal junction, and wherein the multiple annular treatment patterns comprise one or more of circular, oval, elliptical, egg-like, non-circular, non-elliptical, or asymmetrical patterns, or patterns that correspond to the shape of the corneolimbal junction or the limbus. In some examples, the laser energy is directed to a 360° predetermined treatment pattern that is interrupted nasally by 10-30° and temporally by 10-30°. In some examples, the laser energy is directed to trans-scleral treatment locations on multiple annular treatment patterns that target the perilimbal outflow structure, pars plicata, and pars plana.

Some examples further include placing a heat sink in contact with the eye over the trans-scleral treatment locations to conduct heat away from the surface of the eye. In some examples, placing the heat sink in contact with the eye comprises placing a curved contact lens on the surface of the eye. In some examples, placing the contact lens on the eye comprises placing a cooled contact lens that substantially conforms to the surface of the eye. In some examples, the contact lens is cooled in situ on the surface of the eye. In various examples, the laser energy has a near-infrared wavelength of 0.8-2.2 µm, optionally including a wavelength of about 1-2.2 µm, 1.0-1.7 µm, 0.80-0.85 µm, 1.4-1.6 µm, and/or 1.47 µm. In some examples, the laser energy has a near-infrared wavelength of about 1.4-1.5 µm, optionally at 1.47 µm. In some examples, the protective thermal preconditioning and therapeutic bio-stimulation are controlled by one or more of the laser's power, irradiance, scanning speed, cycle repetition rate, number of cycle repetitions, spot size, and duty cycle. In some examples, the laser energy is directed to the treatment location in a spot having a diameter of 500-1000 µm, optionally about 600 µm. Some examples further include detecting the limbus and/or corneolimbal junction of the subject with an optical imaging system. In some examples, the predetermined trans-scleral treatment locations are determined by the shape of the limbus and/or corneolimbal junction of the eye of the subject.

Some examples further include spacing the non-contact laser away from the eye with a patient interface, the patient interface comprising a spacer that maintains the eye in a substantially fixed location for imaging and treatment, and the spacer maintains a non-contact laser energy source, configured to produce the laser energy, spaced from and not contacting the surface of the eye. In some examples, the patient interface further comprises a speculum for placement between the eyelids of the subject to expose the eye to the laser energy, and the speculum is placed between the eyelids to expose the sclera of the subject. In some examples, the patient interface further comprises a fixation ring for a contact lens, and the fixation ring comprises a resilient sealing face, and the fixation ring is placed against the eye of the subject and suction is applied to between the contact lens and eye to create negative pressure and secure the fixation ring to the eye and substantially immobilize the eye of the subject. In some examples, the negative pressure is adjustable. In some examples, the spacer and/or fixation ring and/or contact lens are cooled while the method is being performed. In some examples, the spacer and/or fixation ring are cooled by introducing a cooling fluid through internal fluid flow channels in the spacer and/or fixation ring and/or contact lens. Some examples further include positioning the patient interface in a treatment location relative to the surface of the eye of the subject with a positioning arm.

In some examples, the laser energy is directed in the curvilinear pattern to form contiguous concentric annular treatment zones at different radii from the foveal avascular zone. In some examples, the laser energy is directed in the curvilinear pattern on the macula through all macular annuli at a common scanning speed so that for each macular annulus a plurality of evenly-spaced and overlapping laser pulse spots are sequentially delivered along a complete circle to produce an irradiated annular treatment zone within each annulus. In various examples, the laser energy is directed to the annuli to deliver a total laser energy in the range of 50 mJ to 12 J in an area of 20 $cm^2$ to 30 $cm^2$ at a peak pulse power in the range of 100 mW to 2 W. In some examples, the laser energy is directed to three to five contiguous concentric annuli on the macula, each annulus having a substantially equal width, and wherein the plurality of trans-scleral treatment locations comprises three concentric annuli on the sclera around the limbus at radii $R_1$, $R_2$ and $R_3$ that correspond respectively to locations overlying the primary aqueous outflow pathway, the pars plicata ciliary body, and the pars plana. In some examples, the laser energy is directed to five contiguous annuli on the sclera, each annulus having a width of approximately 500 microns, and wherein the plurality of trans-scleral treatment locations comprises three concentric annuli on the sclera at distances of approximately 1.5, 2.5, and 3.5 mm from the corneoscleral junction. In some examples, the sublethal thermal elevations correspond to a raise in the temperature of the target tissue in the annuli on the macula to a temperature of no more than 47° C., and the laser beam raises the temperature of the target tissue in the trans-scleral treatment locations to no more than 57° C.

In some examples, the laser energy directed to the trans-pupillary treatment locations comprises a pulsed laser beam at 810 nm, the laser energy directed to the trans-scleral treatment locations comprises a continuous-wave laser beam at 1475 nm, and wherein the laser energies are directed along a common optical path from at least one beam splitter. Some examples further include detecting a position of the target eye tissue and wherein the directing the laser energy is performed with a laser scanner based on the detected position. Some examples further include detecting a position of the foveal avascular zone and/or optic disk of the subject. In some examples, the laser energy is directed in the curvilinear pattern at a constant circumferential scan speed of between 1.5 mm/s and 2 mm/s that produces a pulse-to-pulse overlap of 99% or greater. In some examples, the laser energy is directed trans-pupillary at a pulse repetition period of 2 ms and a pulse duration of 100 µs. In representative examples, the curvilinear pattern is configured to target retinal pigment epithelial (RPE) cells.

According to a further aspect of the disclosed technology, patient interface assemblies for docking a laser treatment device to an eye to be treated with the laser treatment device, include a lens holder configured to retain a contact lens heat sink against the eye, wherein the lens holder includes internal cooling channels that communicate with fluid flow inlet and outlet ports, and a spacer dockable to the lens holder for holding a laser output a spaced distance from the contact lens heat sink. Some examples further include a resilient sealing ring on the lens holder that extends around the contact lens to create a sealing chamber between the contact lens and the eye to retain the lens holder against an eye when a suction is applied to the sealing chamber, and the sealing chamber communicates with a suction port. In some examples, the contact lens comprises a contact lens with a central opening to permit air to pass into the sealing chamber while still maintaining the negative pressure in the sealing chamber. Some examples further include a speculum, wherein the speculum comprises jaws that hold opposing eyelid blades in a spaced relationship, and the blades are configured to fit around and retain the lens holder. Some examples further include a laser triangulation system for Z-focus camera viewing of the contact lens. Some examples further include an X-Y-Z positioner for positioning the patient interface with the sealing ring of the lens holder against the eye of the subject, and the spacer docked to the lens holder.

According to a further aspect of the disclosed technology, patient interfaces for docking a laser treatment device to an eye to be treated with the laser treatment device, include a spacer, such as a frustoconical spacer, that tapers from an enlarged first face to a smaller second face, and a laser emission source carried by the cone and spaced away from the smaller second face, a lens holder collar that tapers from a larger first face for mating with the second face of the spacer to a smaller second face that is circumscribed by a resilient patient fixation ring to form a seal against the eye to be treated, wherein the collar comprises an internal cooling fluid passageway, an inlet port and an outlet port for circulating cooling fluid through the collar, a heat sink contact lens held in the collar above the fixation ring to form a suction chamber between the contact lens and the eye when the collar is docked against the eye of the subject, and a suction port that communicates with the suction chamber. According to a further aspect of the disclosed technology, methods of docking the laser treatment devices to an eye to be treated with a laser treatment device, include inserting the blades of the speculum into the eye to separate the eyelids and expose the sclera, retaining the lens holder between the blades of the speculum and optionally suctioning air from the sealing chamber, activating the X-Y-Z positioner to dock the spacer to the lens holder, and introducing cooling liquid through the internal cooling channels of the lens holder by introducing cooling liquid through the fluid inlet port and out of the fluid outlet port. Some examples further include viewing the contact lens and eye with optical viewing software. Some examples further include viewing the retina of the eye with optical viewing software. Some examples further include performing a laser treatment of the sclera and/or retina through the patient interface, with the laser held in a spaced relationship to the sclera.

The foregoing summary describes various aspects of the systems, devices and methods that are disclosed in more detail throughout this specification. The summary is provided for the convenience of the reader and is not limiting on the scope of any claims. The foregoing and other objects, features, and advantages of the disclosed technology will become more apparent from the following detailed description, which proceeds with reference to the accompanying figures.

BRIEF DESCRIPTION OF THE DRAWINGS

FIG. 6D is an exploded view of the interface cone, contact lens holder and speculum.

DETAILED DESCRIPTION

Terms

Figure 1:
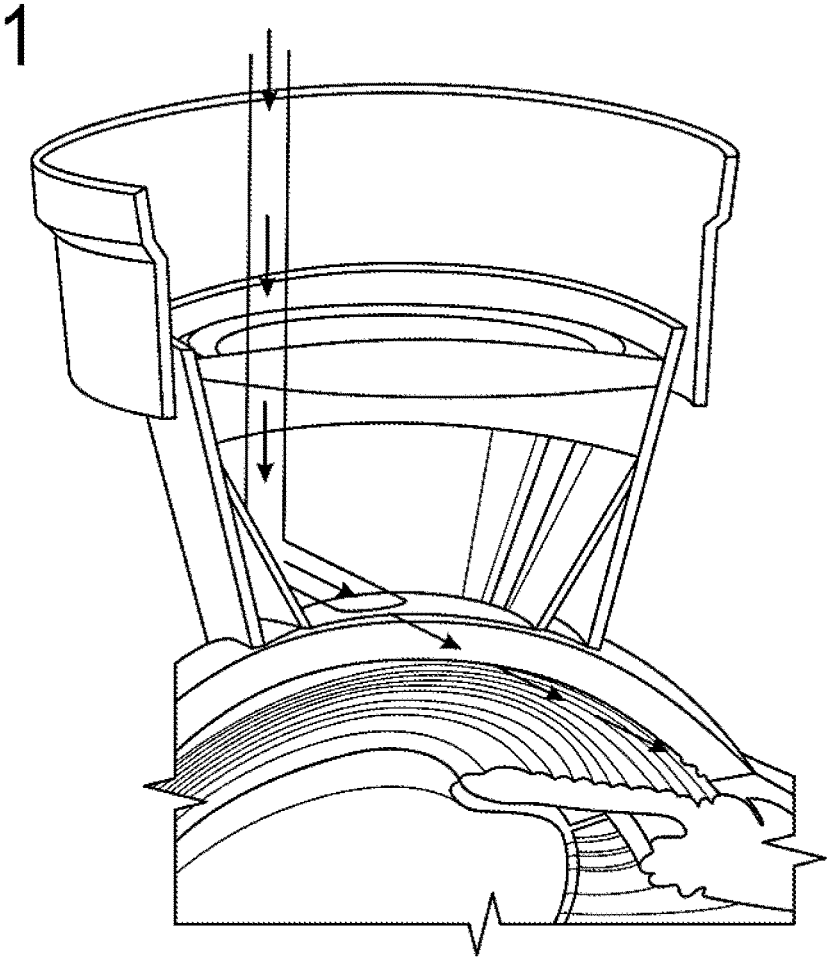
FIG. 1 schematically illustrates traditional prior art trans-corneal laser trabeculoplasty performed using a slit-lamp laser delivery system and a corneal contact gonioscopy lens to visualize and direct the laser beam ab-intern at the pigmented trabecular meshwork (TM) below the Schwalbe Line (SL) in the angle of the eye's anterior chamber.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular sequence for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show various ways in which the disclosed systems, methods, and apparatus can be used in conjunction with other systems, methods, and apparatus.

With reference to eye anatomy, "anterior" refers to the front of the eye, toward the anterior pole. "Posterior" refers to the back of the eye, toward the posterior pole.

A "limbus-contoured" treatment pattern refers to treating locations on the surface of the eye that mimic the outline of the limbus of that eye. The treatment pattern may be at the limbus itself, or spaced posterior to the corneolimbal junction, but retaining the limbal outline of the specific patient being treated.

A "non-contact laser source" refers to a laser source (e.g., including one or more diodes at the same or different wavelengths, beam splitting optics, beam shaping optics, optical scanner components, etc.) that produces a laser beam that is directed to the intended target and that does not have parts in contact with the target surface irradiated by the laser source. For example, in a non-contact laser source, the laser beam is not emitted from a probe in contact with the irradiated surface.

The "optical axis" of the eye is the straight line passing through the geometrical center of the cornea and the nodal (central) point of the eye.

"Therapeutic biostimulation" refers to stimulation of biological mechanisms that achieve a therapeutic effect (such as lowering IOP or improving the trophism in the retina).

"Thermal preconditioning" refers to preliminary mild step-rise heating of tissue to protect it from thermal damage and make it more damage-resistant at even more elevated temperatures. Without being bound by theory, it is believed that initial mild heating ("hyperthermia") induces heat-shock proteins that minimize folding or promote productive refolding of still viable cells, such as cells that are stressed but non lethally damaged by the laser irradiation.

Treatment patterns may have various shapes. A circumferential pattern surrounds a curved structure, such as the limbus, for example in a curved or polygonal shape. An "annular" pattern surrounds a reference structure (such as the limbus or foveal avascular zone) and is generally ring/oval-like.

References to dimensions of macula, and related fovea, foveal avascular zone (FAZ), umbo, perifovea, parafovea, etc., refers to retinal anatomical features for the typical human eye.

Introduction

An ab externo trans-scleral automated photothermal laser delivery system lower intraocular pressure by irradiating an eye in a subject from a non-contact laser energy source that is configured to direct laser energy from a location spaced from the eye. In disclosed examples, the laser energy has a near-infrared wavelength of 0.8-2.2 µm or 1-2.2 µm, such as 1.0 to 1.7 µm, for example a wavelength of about 0.80-0.85 µm or a wavelength of about 1.4-1.6 µm. In some disclosed embodiments the wavelength is 1.47 µm. A processor may be configured with instructions to direct the laser energy to a plurality of treatment locations irradiated in a predetermined treatment pattern on an external surface of the eye. The treatment locations are for example 0-5 mm (such as 1-5 mm) anterior or 0-4 mm (such as 1~4 mm) posterior to the corneolimbal junction, and the laser energy is repetitively directed to the same irradiated treatment locations of the eye. The treatment locations are irradiated at time intervals that induce protective thermal preconditioning and therapeutic bio-stimulation of one or more structures of the eye, i.e. the trabecular meshwork and/or ciliary body to lower IOP.

An energy delivery system coupled to the energy source and the processor is configured to repetitively deliver the energy specifically to the plurality of predetermined irradiated treatment locations on the predetermined treatment pattern at the intervals that induce protective thermal preconditioning, propagation of a heat wave to targeted structure deeper in the eye, and hyperthermia and bio-stimulation of the targeted structures. Without being bound by theory, it is believed that these photo-thermal effects activate cellular biological cascades that induce biomechanical and biochemical responses, such as modification of the extracellular matrix, that ultimately lower the intraocular pressure without photocoagulation and destruction of tissue.

In some examples a processor is configured with instructions to repetitively deliver the energy specifically to the plurality of irradiated treatment locations at intervals that target an increase in the temperature of the outer 200-550 µm scleral layers to a temperature of about 43-57° C. For example, the irradiance of the laser energy and a scanning speed with which the laser energy moves around the treatment pattern increases the temperature of the outer 200-550 µm scleral layers to a temperature of about 43-57° C., or less than 45° C. or about 43-45° C. The increase in temperature of the tissue is, for example, no more than 8 or 10° C. above the baseline temperature of the tissue. The peak temperature of the tissue is below a coagulation temperature of the irradiated tissue. The processor may be configured with instructions to receive an input corresponding to a location of the corneolimbal junction or limbus of the subject and determine the plurality of treatment locations in response to the input. The treatment locations are offset radially outward from the input location corresponding to corneolimbal junction or limbus to contour the treatment pattern to the anatomy of the eye of the subject and achieve customized delivery of the heat wave to the targeted deeper structures.

In some examples, the treatment locations are within a 360° pattern posterior to the corneolimbal junction. The treatment locations can be coextensive with the 360° treatment pattern, or only along portions of the treatment pattern (for example in multiple arcs or spots on the treatment pattern). The processor directs the laser energy to a set of pre-identified treatment locations on the surface of the eye during a first treatment cycle, and during one or more subsequent treatment cycles (repeat cycles) directs the laser energy to the same or a subset of the same pre-identified treatment locations. Precise cyclic thermal elevation of scleral tissue underlying the pre-identified treatment locations at intervals of time induces thermal elevation/relaxation cycles of the irradiated tissue to occur between treatment cycles and propagation of the heat wave to target structures deeper in the eye.

In some embodiments, the processor sets the speed of each treatment cycle to achieve the thermal relaxation by spacing irradiation of the treatment locations at intervals that produce a targeted time-temperature history. For example, the interval between irradiation of the same treatment location produces a duty factor, (the ratio between the active exposure ON time/[active exposure+relaxation OFF time]), in the 2-50% range. In some examples, the interval between irradiation of the same treatment location is about 10-300 ms, for example 100-200 ms. However, the time interval between irradiations of a specific treatment location may vary depending on other parameters.

In some examples, the predetermined treatment pattern extends through all or a portion of a 360° limbus-guided circumferential pattern or annulus which is located about 1-1.5 mm posterior to the corneolimbal junction. Although reference is made to generally annular treatment patterns, the energy pattern can be delivered in many configurations, for example a portion of an annulus, a polygon, or intermittent treatment along a generally circumferential pattern. In one example the treatment pattern extends through a 120° arc. Other predetermined treatment patterns may extend through a generally annular shape about 2 mm to 3 mm and/or 3 mm to 4 mm posterior to the corneolimbal junction. Since the limbus and corneolimbal junction may be other than circular, a pattern spaced a fixed distance from the corneolimbal junction through 360° will mimic the shape of the limbus and corneolimbal junction. Limbus-guided patterns may for example be ovoid, elliptical, generally arcuate with non-arcuate segments, or irregularly-shaped but otherwise surrounding the limbus. A treatment pattern provides a template on which treatment locations may be located, and the treatment locations on the treatment pattern may be either contiguous (in a continuous pattern) or not contiguous (spaced treatment locations such as spots or arcs positioned at intervals around the treatment pattern).

The predetermined treatment pattern may be one or more treatment patterns that specifically and/or differently target the aqueous production and outflow pathways such as the ciliary body and the trabecular meshwork. In some examples the annuli are spaced about 1.5 mm, 2.5 mm and 3.5 mm posterior to the corneolimbal junction to target the outflow pathways at 1.5 mm, the pars plicata at 2.5 mm and the pars plana at 3.5 mm. The 360° pattern may be interrupted to avoid anatomic structures within the eye that could be harmed by irradiation. For example, the pattern is interrupted nasally and temporally, such as by 10-30° nasally and/or 10-30° temporally. In some examples a heat sink, such as a curved contact lens, is placed in contact with the eye over the treatment locations to conduct heat externally away from the treated surface of the eye. The lens may be a cooled lens that substantially conforms to the surface of the eye, and which is either pre-cooled or cooled in situ while applanated on the surface of the eye.

The protective thermal preconditioning and therapeutic bio-stimulation may be controlled by one or more of the laser's power, irradiance, scanning speed, cycle repetition rate, number of cycle repetitions, spot size and duty cycle. For example, the processor is configured to direct the laser energy to the treatment location in a spot having a diameter of 500-1000 µm, for example about 600 µm. The system may also include an optical imaging system for detecting the limbus and/or corneolimbal junction of the subject. The processor may be configured to identify the predetermined treatment locations as determined by the shape and size of the limbus and/or corneolimbal junction of the eye of the subject. The 360° locations identified by the processor may be circular, oval, elliptical, egg-like, non-circular, non-elliptical, asymmetrical or other shapes determined by the anatomy of an individual limbus. The contoured annulus patterned by the shape of the limbus or corneolimbal junction is in effect a larger (such as greater diameter) version of the limbus or corneolimbal junction of the specific subject being treated.

Disclosed embodiments of the present method transsclerally deliver laser energy, for example near infrared laser energy (such as from a 1.475 µm IR laser), with low scattering. The laser may be a continuous wave (CW) infrared laser. The laser energy interacts with water-containing cells in the superficial sclera (for example to a depth of 200-500 µm beneath the surface of the sclera) instead of interacting primarily with pigmented cells in deeper ocular structures such as the trabecular meshwork. When water in the cells absorb the laser energy in the superficial sclera, a thermal elevation is created and cell transduction cascades in the deeper ocular structures are affected. The laser energy may be repetitively and specifically applied to the same treatment locations at intervals spaced in time by the period of a treatment cycle to generate a heat wave at each treatment location that propagates three-dimensionally or 360° spherically into deeper scleral layers and to the structures of the aqueous outflow tract and/or the ciliary body. The energy delivery achieves a photo-stimulation therapeutic threshold through a gentle photothermal rise that avoids complications, such as those associated with ALT burns or with SLT's cavitation interaction. This method avoids the necessity of gonioscopic targeting of the laser to the trabecular meshwork in the iridocorneal angle (FIG. 1) and avoids the iatrogenic drawbacks of moving a contact probe over the surface of the eye. The procedure may also be performed under topical anesthesia and without peri-retrobulbar block.

In one disclosed embodiment the laser continuously irradiates a 360° treatment pattern, or portions of the pattern, in a clockwise direction beginning at 0° and moving in one direction through 360° before beginning and repeating the cycle again. Such a cycle could alternatively proceed in a counter clockwise direction or ping pong around to non-adjacent locations on the treatment pattern to complete the cycle. For example, a laser spot of a specified diameter may sequentially irradiate the target pattern om a ping pong manner at 0°, 180°, 10°, 190°, 20°, 200°, 30°, 210°, 40°, 220°, etc. through an entire 360° pattern to form either a continuous or discontinuous pattern. In some disclosed examples each cycle irradiates selected treatment locations, and all the treatment locations may be irradiated before proceeding to the next cycle. The plurality of treatment locations on the pattern may correspond to an angle within a range from about 30° to about 360° around a sclera of the eye, for example within a range from about 90° to about 360°, within a range from about 90° to about 150, 160, 170 or 180°, or within a range from about 180° to about 360°. A plurality of treatment locations may correspond to an angle of about 30°, about 45°, about 60°, about 75°, about 90°, about 150°, about 180°, about 270°, or about 360°.

The treatment pattern may be a continuous treatment pattern such as an annulus that forms an uninterrupted curve, or a discontinuous treatment pattern having spaces between "dashes" or "spots" of treatment along the treatment pattern. The treatment pattern may be a plurality of treatment patterns, and the plurality of patterns may be overlapping or non-overlapping. For example, the plurality of annuli may overlap to generate a treatment annulus with a width greater than the spot size of the laser energy beam. Non-overlapping annuli will have a pre-determined radial distance between each of the plurality of treatment patterns. For example each non-overlapping treatment pattern may be a different fixed distance from the corneolimbal junction so that each of the patterns is a limbus contour-guided pattern of different circumference.

In some examples the scanning speed of circumferential movement of the laser around the treatment pattern to treat all the treatment locations determines the interval between irradiation of each treatment location on the annulus. Movement of the laser during the interval between repetitive irradiations of a specific treatment location fractionates delivery of energy to each treatment location to permit thermal relaxation between irradiation of each treatment location. The total energy delivered to each treatment location may be determined in part by the number of cycles, with total energy being a product of the number of cycles times the energy applied per cycle.

Figure 2A:
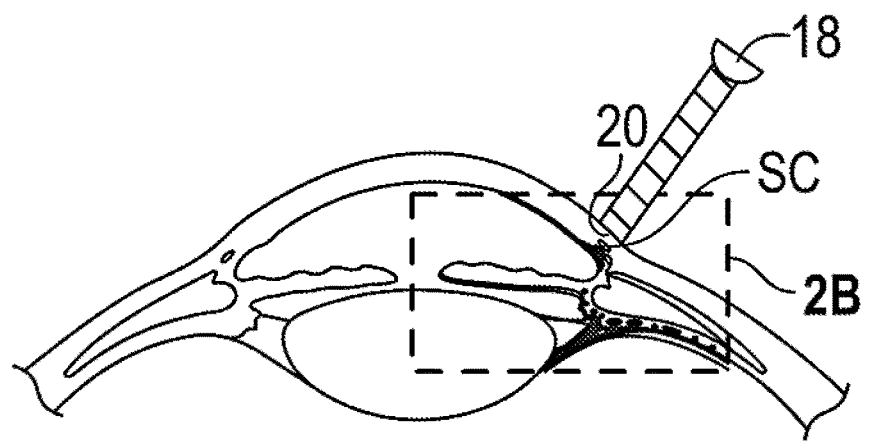
FIGS. 2A and 2B schematically illustrate an example of a trans-scleral laser trabeculoplasty method which directs laser energy at the surface of the eye without contacting that surface. A laser beam is directed ab-externo to the perilimbal area through the corneoscleral junction over the outflow pathway structures.
Figure 2B:
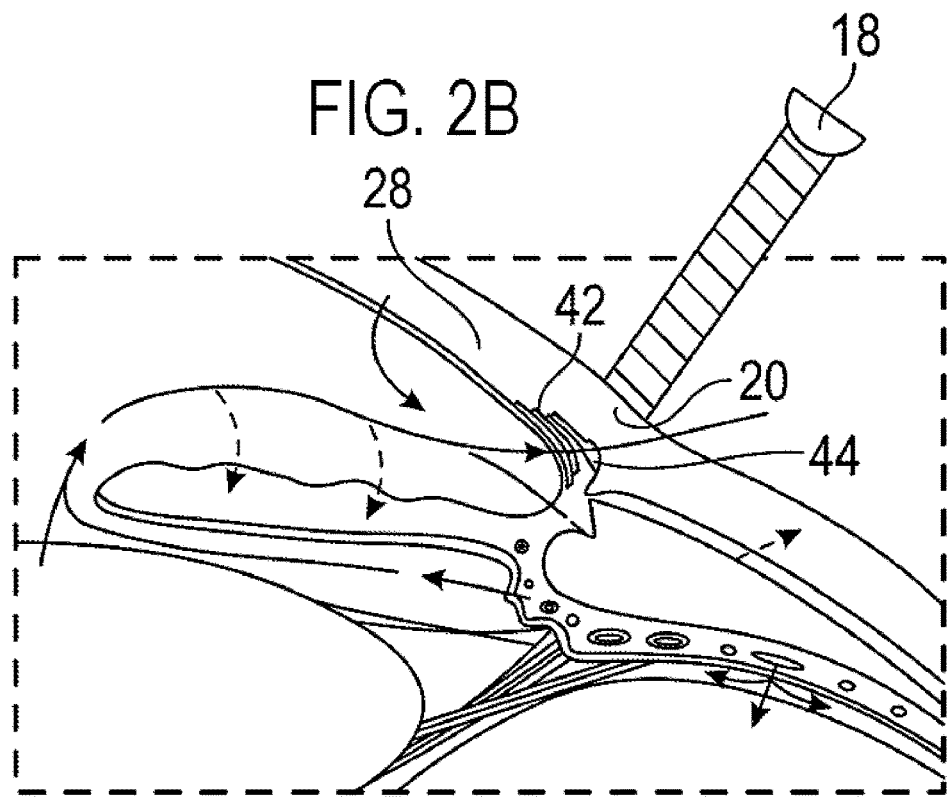
Figure 3:
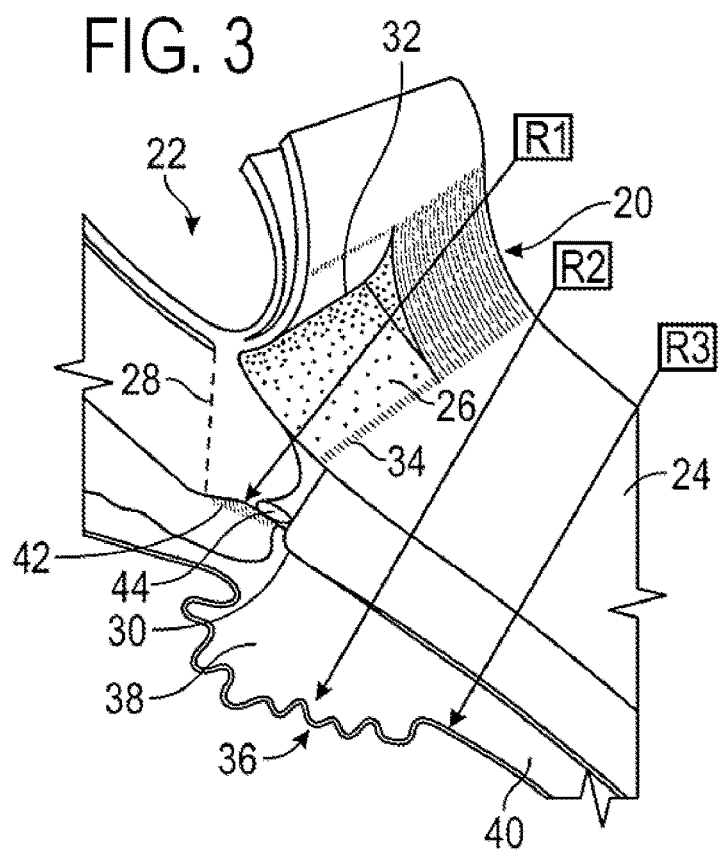
FIG. 3 schematically illustrates the anatomy of the corneoscleral junction bounded anteriorly by the corneolimbal junction and posteriorly by the sclerolimbal junction.

Detailed Description of Illustrated Embodiments
(FIGS. 2-4)

Detailed embodiments of the method and system are described with reference to the drawings. FIG. 2A schematically illustrates a method of lowering IOP. Laser energy is emitted from a non-eye contacting laser energy source 18 spaced from the surface of the eye and directed toward the corneoscleral junction 20, which is the transition zone between the cornea and the sclera. FIG. 2B is an enlarged view of the box in FIG. 2A to better illustrate the corneoscleral junction at which the laser energy is directed to propagate heat waves to the underlying trabecular meshwork and other structures of the aqueous outflow tract. FIG. 3 is a further enlarged view of the corneoscleral junction 20 where the cornea 22 meets the sclera 24. The limbus 26 which forms the corneoscleral junction is bounded internally (within the eye) by Schwalbe's line (SL) 28 and the scleral spur (SS) 30. Limbus 26 is bounded externally (at the surface of the eye) by the corneolimbal junction (CU) 32 and sclerolimbal junction (SLJ) 34. The CU 32 is also known as the apparent or anterior limbus, and the SLJ 34 is also known as the surgical or posterior limbus. The conjunctiva and capsule of Tenon (not shown) fuse before inserting approximately 0.5 mm posterior to the CU. The underlying ciliary body 36 that produces the aqueous humor is divided into the pars plicata 38 and pars plana 40. The trabecular meshwork (TM) 42 is located around the base of cornea 22, near ciliary body 36, and is part of the apparatus for draining aqueous humor from the eye. Schlemm's Canal 44 is a circular lymphatic-like vessel around the base of the cornea 22 adjacent trabecular meshwork 42 that is also part of the aqueous outflow tract. The distance from the corneolimbal junction 32 to the sclerolimbal junction 34 is about 2 mm in a typical eye.

Irradiating the limbus and/or perilimbal region propagates the heat waves that travel through the sclera to photostimulate most of the structures of the primary aqueous humor outflow pathway, such as the collector channels and/or their ostia, Schlemm's Canal, the juxtacanalicular TM, Corneoscleral TM and Uveal TM. All these structures lie in the space underneath the limbus. In some instances only a single treatment pattern at a distance $R_1$ posterior to the corneolimbal junction is used. In other instances, two treatment patterns at $R_1$, $R_2$ posterior to the corneolimbal junction are used to achieve greater spread of the thermal wave to more of the structures of the aqueous humor outflow pathway and/or the aqueous humor production structures (in the ciliary body). In yet other instances three treatment patterns $R_1$, $R_2$, $R_3$ posterior to the corneolimbal junction are treated to achieve extensive spread of the thermal wave to the targeted structures of aqueous humor production and outflow. In other embodiments, more than three treatment patterns can be used, for example four, five or six treatment patterns each at a fixed distance from the corneoscleral junction.

The distances $R_1$, $R_2$, $R_3$ from the corneolimbal junction can be a custom pattern that mimics the often-irregular contour of the corneolimbal junction such that each of $R_1$, $R_2$, $R_3$ are a constant distance from the corneolimbal junction but different distances from the optical axis throughout the 360° of the pattern. Alternatively, the distances $R_1$, $R_2$, $R_3$ are fixed distances from the optical axis throughout the 360° of the pattern such that the treatment pattern has a substantially constant radius. For example, in a subject having an average corneal radius of 6 mm (measured from the optical axis), $R_1$ may have a fixed radius of 7.5 mm from the optical axis to space it on average 1.5 mm from the corneolimbal junction. $R_2$ may have a fixed radius of 8.5 mm from the optical axis to space it on average a distance of 2.5 mm from the corneolimbal junction, and $R_3$ may have a fixed radius of 9.5 mm from the optical axis to space it on average a distance of 3.5 mm from the corneolimbal junction.

Figure 4A:
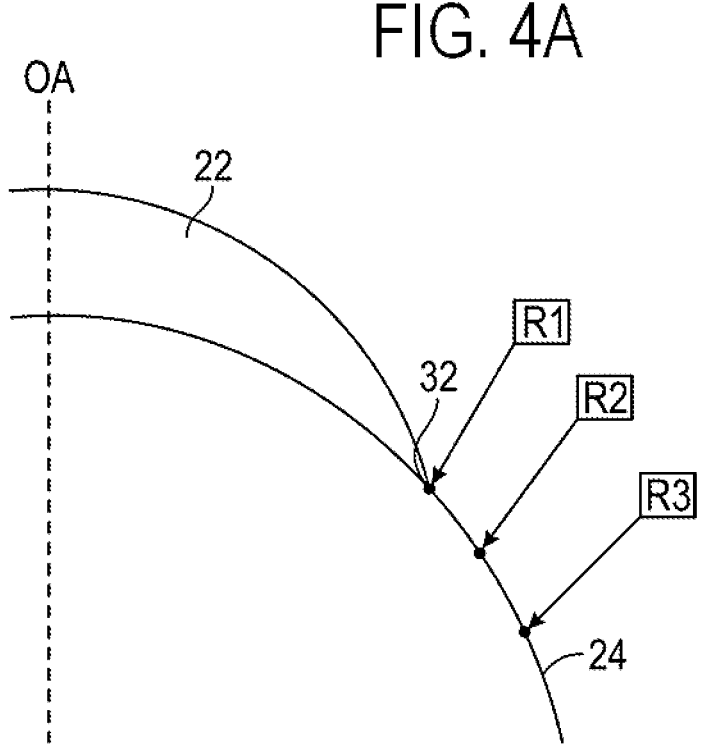
FIGS. 4A and 4B are schematic drawings that show one or more locations of generally annular treatment patterns with various radii $R_1$, $R_2$ and $R_3$ at which the trans-scleral laser can be directed at the eye. OA is the optical axis of the eye.
Figure 4B:
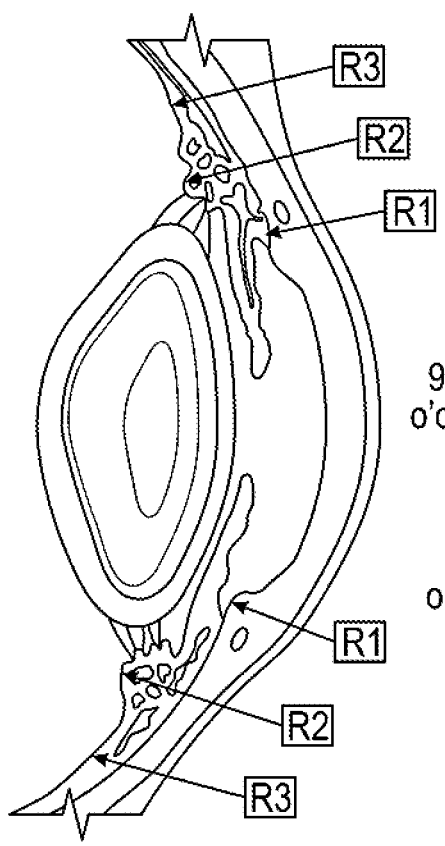

FIGS. 3, 4A and 4B show examples of locations where the perilimbal region may be irradiated at distances $R_1$, $R_2$, and/or $R_3$ posterior to the corneolimbal junction 32. For example, $R_1$, $R_2$, and $R_3$ may respectively be about 0, 1.5 and 2.5 mm posterior to the corneolimbal junction 32, or about 1.5 mm, 2.5 mm and 3.5 mm posterior to corneolimbal junction 32. In some examples $R_1$ may be 0-2 mm posterior to the corneolimbal junction, $R_2$ may be 2-3 mm posterior to corneolimbal junction 32, and $R_3$ may be 3-4 mm posterior to corneolimbal junction 32. In other iterations $R_1$, $R_2$, and $R_3$ may be any combination, for example, of $R_1$=0, 0.25, 0.5, 0.75, 1.0, 1.25, 1.5, or 1.7 mm or more posterior to the corneolimbal junction, $R_2$=2.25, 2.5, 2.75, 3.0, or 3.25, or more posterior to the corneolimbal junction, and $R_3$=3.5, 3.75, 4.0, 4.25, 4.5, 4.75 mm or more posterior to the corneolimbal junction. In some embodiments $R_1$ is between about 1-2 mm from the corneolimbal junction, $R_2$ is between about 2-3 mm posterior to the corneolimbal junction, $R_3$ is between about 3-4 mm posterior to the corneolimbal junction, and $R_1$, $R_2$, and $R_3$ are different distances.

In some embodiments the anatomy of the eye may be imaged, for example using an operating microscope, to identify the shape of the limbus to overlay a treatment pattern that may then be applied to the eye by automated irradiation of treatment locations at the designated treatment locations. In other embodiments, an image analysis software program will recognize the limbus and its anterior margin (the corneolimbal junction). An automated system may be programmed to identify the treatment pattern based on the "custom-limbus" pattern that is posteriorly offset from the corneolimbal junction by a selected constant distance from the corneolimbal junction so that the treatment annulus mimics the actual shape of the limbus of the patient. The shape of the limbus often varies between patients hence customizing the contour of the treatment pattern to the contour of the patient's limbus improves treatment outcomes and/or avoids side-effects that may be caused by unintentional irradiation of eye structures in patients with unusual eye anatomies.

Imaging and automated movement of the laser beam along the treatment pattern, for example in a pre-programmed treatment pattern, achieves precise irradiation of sequential treatment locations on the custom limbus pattern. The automated process permits controlled timing of the interval required for the laser to move through the sequential treatment locations to set pre-selected periods of delay before subsequent irradiation of the sequential treatment locations during a subsequent treatment cycle of the cyclic treatment. Since the laser energy is not applied from a contact probe, the laser beam may moved over the sclera or other portions of the eye at a much faster speed than could generally be achieved with a contact and indented probe.

Optical coherence tomography (OCT) or high intensity focused ultrasound (HIFU) are examples of imaging modalities used to identify one or more of the targeted structures. For example, the 360° locations of the inner and outer margins of the limbus may be imaged by OCT, as disclosed in U.S. Pat. No. 9,618,322. Once the anterior margin of the limbus has been identified and mapped, treatment locations may be selected on annuli that are offset by the desired distances $R_1$, $R_2$, and/or $R_3$ from that anterior margin. An automated system can then precisely irradiate the treatment annulus or annuli at repeatable locations.

The locations $R_1$, $R_2$, and $R_3$ irradiate the sclera overlying different structures of IOP homeostasis, such as the aqueous outflow and production structures. In the illustrated example, $R_1$ is positioned to irradiate the primary aqueous outflow pathways, $R_2$ is positioned to irradiate the pars plicata ciliary body that produces aqueous humor, and $R_3$ is positioned to irradiate the pars plana and the unconventional uveoscleral outflow pathway. Tailoring the locations of the treatment patterns to the specific anatomy of the eye of the subject improve treatment outcomes while reducing the likelihood of complications. The operator may assess the reason(s) for the loss of IOP homeostasis in a particular patient and direct the laser energy to the targeted location(s) that will restore IOP homeostasis. In one example, if the increased IOP is likely due to excessive aqueous humor production then the laser energy and hyperthermic stimulation may be directed at least or exclusively to the ciliary body (such as the pars plicata at $R_2$, and/or the pars plana at $R_3$). If the increased IOP is considered to be due to resistance in the conventional or in the uveoscleral outflow pathways, the laser energy and hypothermic stimulation may be directed at least or exclusively to $R_1$. If increased IOP is likely due to both over-production of aqueous and impaired outflow, then both production and outflow pathways may be targeted, for example at $R_1$, $R_2$, and $R_3$.

Figure 4C:
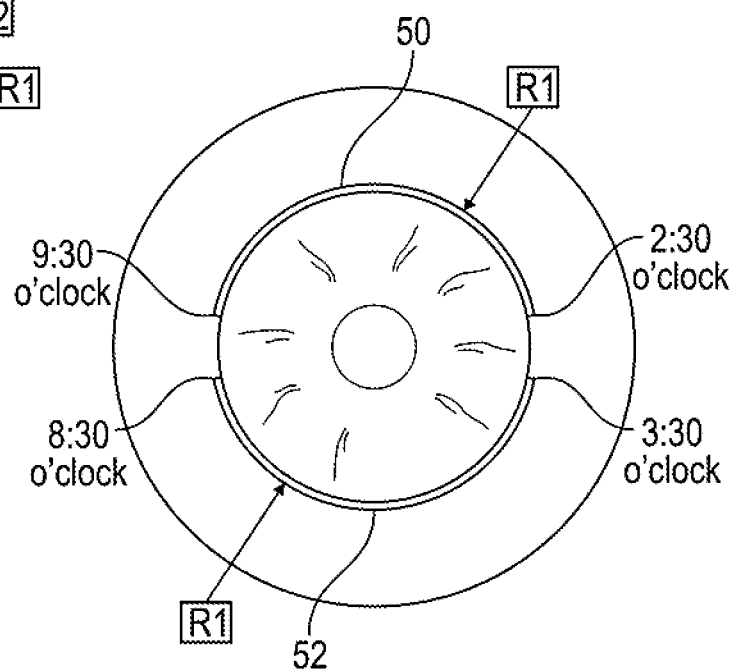
FIG. 4C is a front view of the eye, schematically illustrating a treatment pattern of laser irradiation is directed to the region of the corneoscleral junction to lower IOP. The arcuate pattern is interrupted nasally and temporally; the illustrated superior and inferior arcs are continuous in that they have no internal interruption of either arc.

In the embodiment shown in FIG. 4C an annular treatment pattern is applied at a distance of about 1.5 mm posterior to the corneolimbal junction, with the treatment locations interrupted to form multiple arcs, such as a superior arc 50 and an inferior arc 52. Each of these illustrated arcs is uninterrupted in that the treatment locations are contiguous and not spaced, but the arcs are separated by temporal and nasal interruptions to avoid irradiation of structures in the region. The contiguous locations are treated by moving a continuous wave laser beam along the arc with the laser on. Interruptions may be formed by turning the laser off and on in pulses to form the non-contiguous treatment locations. In some embodiments, the laser beam is circumferentially moved over the superior and/or inferior arcs 50, 52 with steady and repeatable speed by a computer-driven electro-optical scanner that assures consistent and always repeatable treatments with reliable amounts of laser energy deposition. In FIGS. 4C and 4E, the laser energy is delivered in an arcuate pattern to produce two 150° arcs. The illustrated arcs are continuous except for being interrupted from about 8:30-9:30 o'clock (255° to 285°) and the 2:30-3:30 o'clock (75° to 105°) positions to avoid the long ciliary nerves, minimize pain, and avoid the risk of anterior segment ischemia.

Figure 4D:
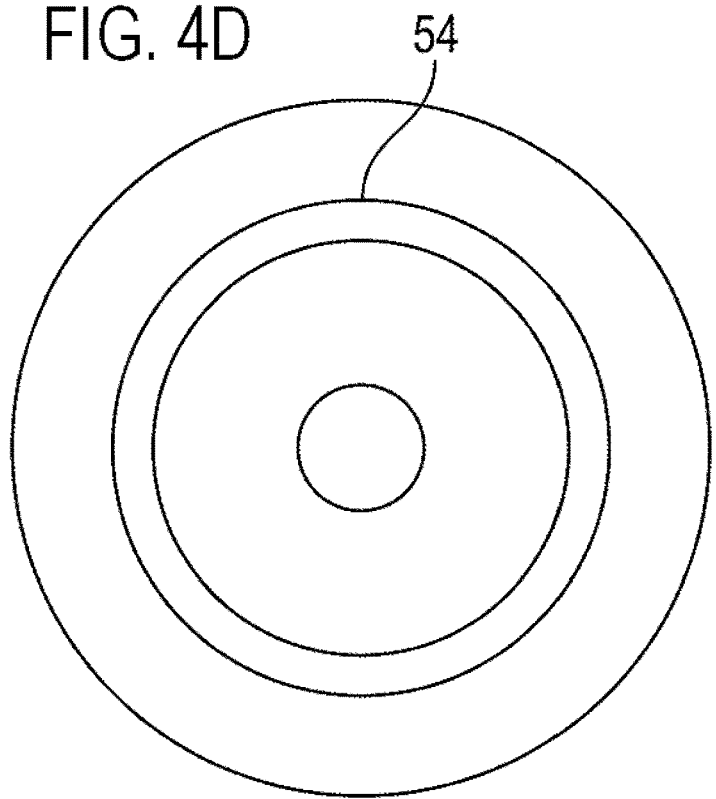
FIG. 4D is a view similar to FIG. 4C but illustrating a treatment pattern of laser irradiation continuously directed to the perilimbal region without the nasal and temporal interruptions.
Figure 4E:
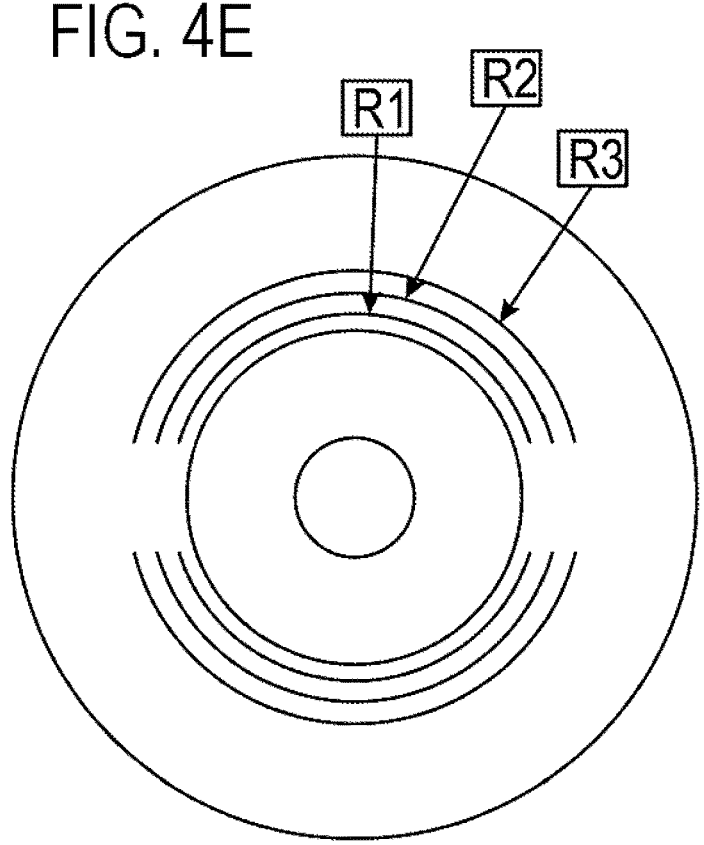
FIG. 4E is a front view of the eye similar to FIG. 4C but showing multiple annular patterns with laser energy directed to the region of the corneoscleral junction at locations $R_1$, $R_2$ and $R_3$ to lower IOP. The arcs have the optical axis as the common center of curvature but are spaced at different distances posterior to the external limbus, and thus from the center of the optical axis.
Figure 4F:
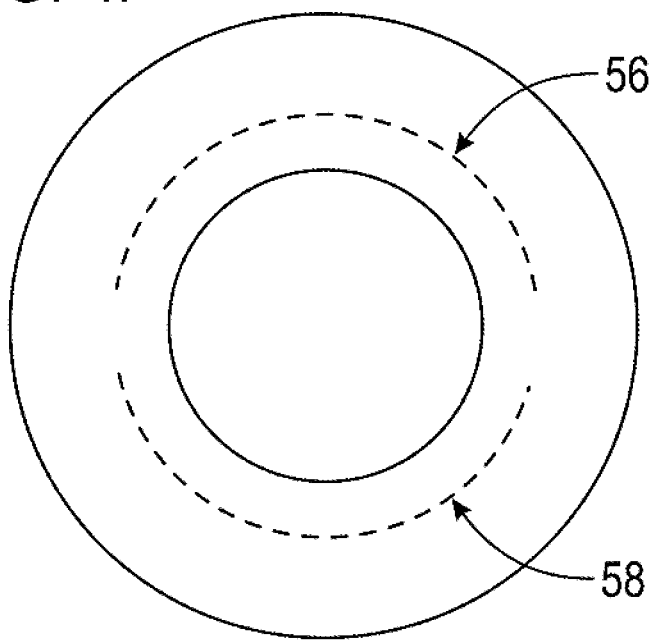
FIG. 4F illustrates the method of applying the trans-scleral laser energy to the eye without contacting the surface of the eye.
Figure 4G:
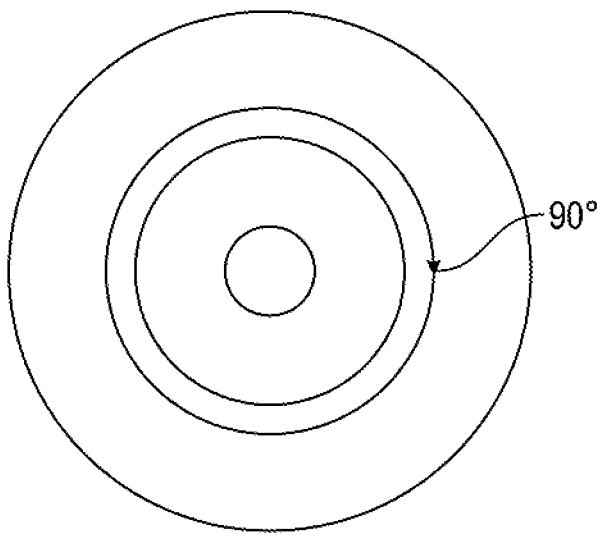
FIGS. 4G, 4H, 4I and 4J illustrate examples of a cycle of the cyclic treatment.

In FIG. 4D, an annular treatment pattern 54 is applied at a distance of about 3.5 mm posterior to the corneolimbal junction, but in a non-discontinuous pattern which is not divided into superior and inferior arcs. In FIG. 4E, multiple annular treatment patterns are applied at $R_1$, $R_2$, and $R_3$ in a superior and inferior arc. FIG. 4F illustrates a treatment pattern that includes a superior primary arc 56 and inferior primary arc 58, but each of the superior and inferior arcs is itself a series of subsidiary discontinuous arcs that is each irradiated by a laser beam of that path or shape that pulses (on/off) as it moves through arcs 56, 58. The laser beam in this instance does not continuously irradiate the eye along the entire path of superior primary arc 56 or inferior primary arc 58. The sequence of irradiating treatment locations need not always be in a circular direction progressively around the eye. For example, one of the subsidiary arcs in primary arc 56 could be irradiated, followed by irradiation of a subsidiary arc in inferior arc 58, and the irradiation pattern could ping-pong back and forth between the arcs 56, 58. However, the sequence in which the subsidiary arcs is irradiated would generally be the same in each treatment cycle to set a preselected period during which the desired thermal relaxation can occur at each treatment location before the next irradiation cycle begins.

The speed of movement of the laser beam along the arc and/or the use of a pulsed laser can both affect the duty cycle, and selection of a uniform period for each cycle establishes a fixed interval between irradiation of each treatment location. The period of each cycle is the time between beginning a first cycle and starting the next cycle. A uniform period for each cycle may be achieved by moving the laser beam at a constant velocity through the multiple cycles. The laser beam is moved at a sufficient velocity, such as 1-100 mm/s or 1-50 mm/s to achieve the desired thermal preconditioning and relaxation. In some examples the velocity is at least 5, 10, 15, 20, 25, 30, 35, 40, 45, or 50 mm/s. In some examples the velocity is no more than 200 mm/s.

A period of thermal relaxation at each treatment location is also set by the period of each cycle. For example, in FIG. 4G a single cycle is illustrated that begins with irradiation of the eye at the 90° location and continues in a clockwise direction around the eye through the 180°, 270° and 360° locations before returning to the 90° location. The next cycle then repeats that process. This pattern can be repeated, for example, by moving the laser beam of a continuous wave (CW) laser over the surface of the eye at a velocity, such as a preselected constant velocity, in the treatment pattern to set the period of thermal relaxation for each of the treatment locations. For example, the treatment location at 90° will be the first location irradiated in the first cycle, and the first location irradiated in the second cycle and subsequent cycles. The interval between irradiations of the 90° treatment location in this example is equal to the period of the cycle.

Figure 4H:
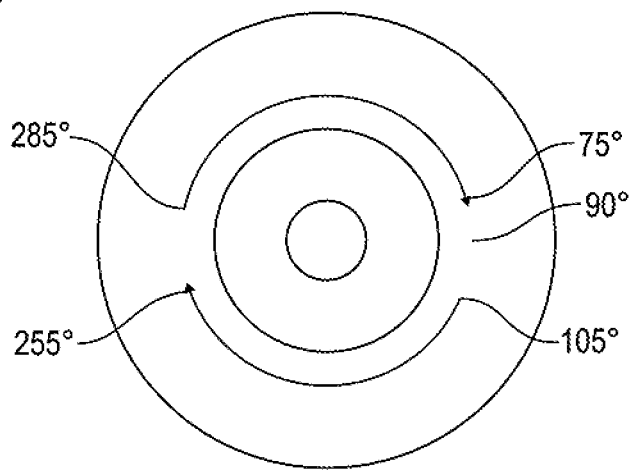

In the example of FIG. 4H and FIG. 4K, a cycle begins with the laser irradiating the surface of the eye at 285° and moving along the treatment annulus to the 75° location. The laser is then turned off as the laser moves over the 75° to 105° locations, but the laser is then turned on again from the 105° to 255° locations. In this instance the formation of the superior and inferior arcs occurs in one cycle. In some examples, only one of a superior or inferior arc would be irradiated, and in such an instance the laser may start, for example, at 285° and move to 75° for the completion of one cycle. The next cycle would then begin at 285° and move to 75° for the completion of subsequent cycles, either by continuing the clockwise movement of the laser beam around the eye or by redirecting the laser beam directly from the 75° location to the 285° location. Each movement of the laser through the 360° annular pattern (or treatment of all the locations in the pattern being used) will be one cycle of treatment that can be repeated a desired number of times. The period for thermal relaxation (the period of the cycle) is generally fixed throughout the multiple cycles of irradiation by moving the laser beam at a constant velocity throughout the cycles, however variable intervals may also be used as desired to achieve the therapeutic effect.

Figure 4I:
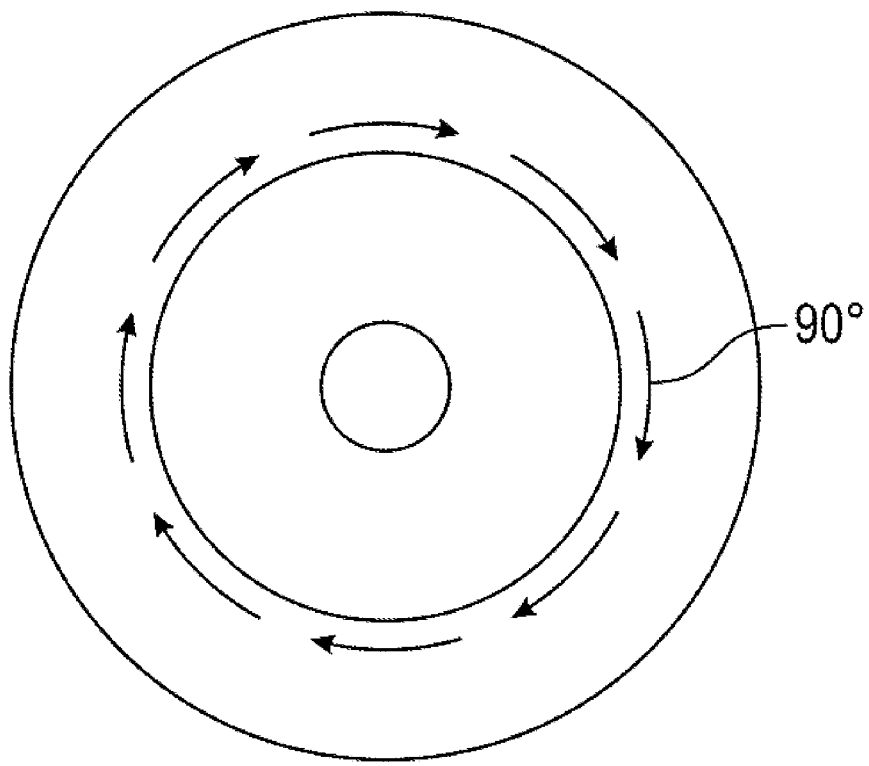
Figure 4J:
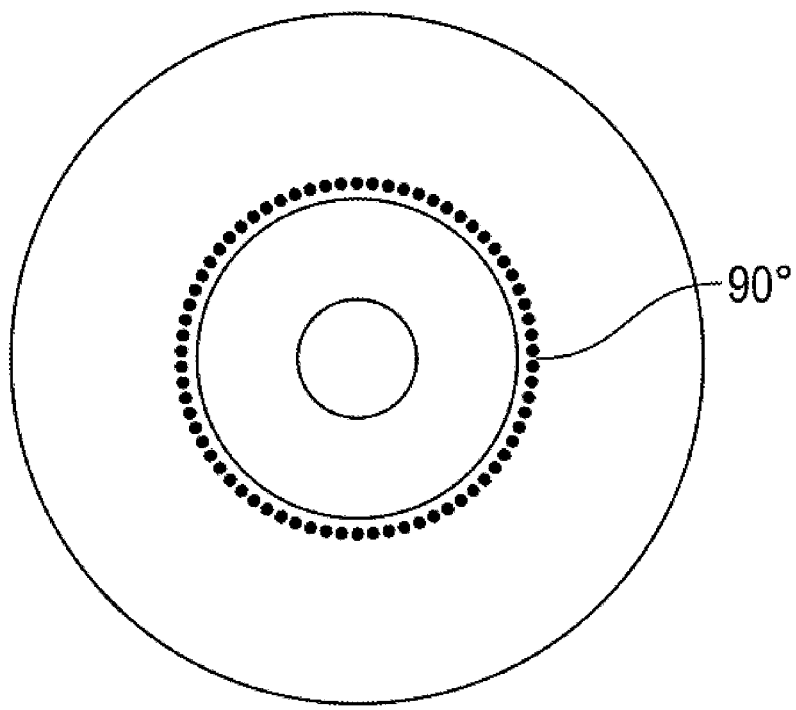

FIG. 4I illustrates yet another example of a treatment pattern that includes multiple arcs of intermediate length around the treatment annulus that are applied in a clockwise fashion. FIG. 4J illustrates yet another treatment pattern in which the treatment annulus is made of multiple laser spots or arcs that are applied in a sequential fashion. A first cycle may constitute the completion of the sequence of arcs in FIG. 4I or the sequence of laser spots shown in FIG. 4J, and subsequent cycles would constitute subsequent scleral irradiation in the same locations and in the same sequence in which they were applied in the first cycle.

For purposes of illustration the described treatment patterns are applied in a clockwise direction, but they may of course also be applied counterclockwise or in other patterns that do not move uniformly in one direction or the other around the eye. The cyclic nature of the repetitive irradiation of the same locations is illustrated with respect to FIG. 4K which divides the right and left eyes into thirty-six equally spaced 10° segments. Treatment locations may for example be identified at each of the 10° locations or a subset of those locations. Treatment locations may also be located between the 10° locations. A direction of clockwise movement of the laser beam around each eye is illustrated by arrows 54, 56.

Figure 4L:
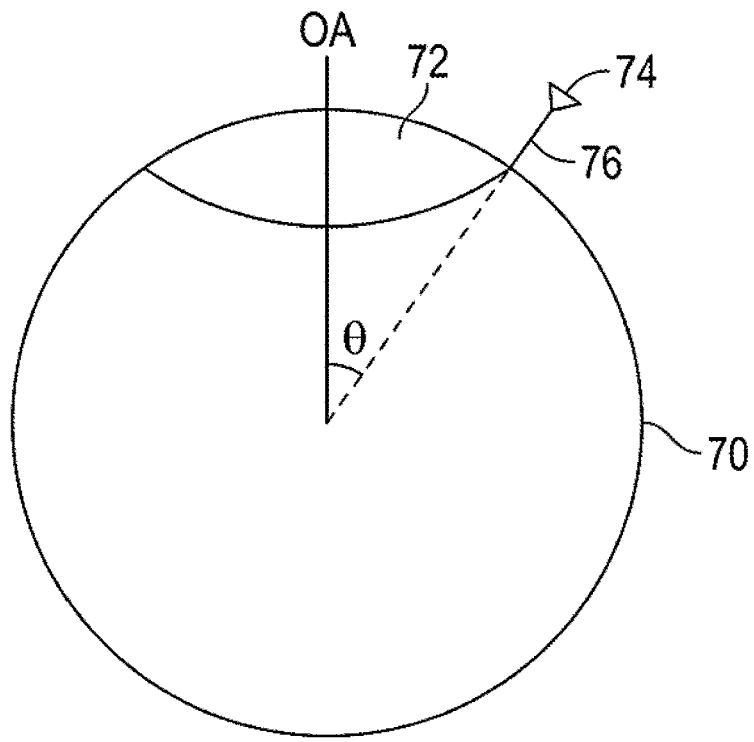
FIG. 4L schematically illustrates an angle between the optical axis of the eye and the incident laser beam at the surface of the eye.

FIG. 4L schematically illustrates an eye 70 having a cornea 72 and an optical axis OA that passes near the center of the cornea and is normal (perpendicular) to the surface of the cornea. A laser energy source (such as a CW diode laser)

74 is spaced outwardly from eye 70 and directs a laser beam 76 toward the surface of the eye at an angle θ to OA to irradiate the surface of the eye and create a thermal wave that penetrates to the aqueous outflow structures and/or the ciliary body. The laser beam does not continue into the center of the globe, but to illustrate the angle between the laser beam and OA the path of the laser is traced in a dashed line to the center of the eye. In this example, the angle θ is 30-50°, for example 35-40°, but the angle at which beam 76 impinges the eye may vary because the therapeutic effect of the disclosed method is achieved by the generation of a heat wave that can nonspecifically propagate through the sclera to heat the aqueous outflow structures and/or the ciliary body. The laser beam therefore need not be aimed directly at a structure to take advantage of the propagated thermal wave.

Figure 4M:
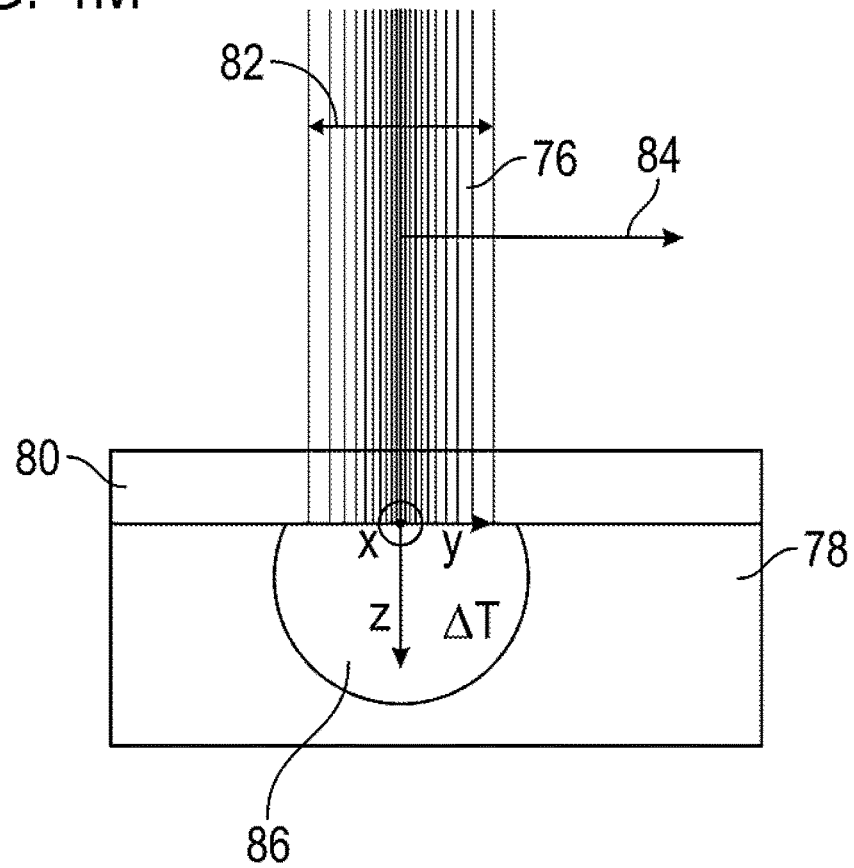
FIG. 4M schematically illustrates the continuous movement of the laser beam as it moves along an annular treatment pattern and through a contact lens to induce a heat wave in the sclera.

FIG. 4M illustrates a laser beam 76 directed at sclera 78 through a heat sink contact lens 80 on the surface of sclera 78. Beam 76 has a width 82 (e.g. 600 nm) and beam 76 moves with a selected velocity in a direction of movement 84 to create a heat wave 86 that spreads three-dimensionally in the x-y-z direction through the superficial sclera toward the underlying targets for modulating IOP homeostasis. As beam 76 moves along the sclera 78 in the y direction, the heat wave is three-dimensionally propagated to the underlying tissue along the path of the laser. For example, the laser is moved along a pattern shown in any one of FIGS. 4C through 4J. The angle of impact with the sclera may be chosen to minimize reflection and scattering of the laser energy and promote effective tissue penetration. In some examples, the laser impinges sclera at an angle of 90±45° with respect to the eye globe tangent at the point of impingement. As discussed below, a contact lens 80 or the sclera 78 itself can contribute or produce a general direction of propagation of the beam 76 into the sclera 78.

Contact lens 80 (FIG. 4M) acts as a heat sink that conducts heat away from the surface of the eye. The heat sink is more fully disclosed in US2018/0177632 that is incorporated by reference to the extent it is not incompatible with the present disclosure. Briefly, the lens has suitable optical properties to allow visualization of the eye through the lens and also to provide or assist with providing the selected angle of incidence on the sclera. In typical examples, light is directed with a laser scanner (such as a 2-mirror galvanometer scanner) through an objective lens (such as an FO lens) and parallel to an optical axis of the objective lens to the eye, typically with the OA of the eye collinearly aligned with the optical axis of the objective lens. Because the sclera and eye have a refractive index (e.g., 1.3-1.5) greater than the refractive index of the air (about 1.0) and the radial position of impingement at the sclera is associated with a tangent that is not perpendicular to the OA of the eye, the incident laser beam, even without the presence of the contact lens 80 is refracted at an angle towards the OA of the eye rather than parallel to it. The contact lens 80 can also assist with this refraction with a preconfigured refractive index or curvature that produces a desired angle of incidence to the sclera for a beam received at the contact lens 80 that is propagating parallel to the OA of the eye.

In general the lens has optical smoothness with maximized transmission of the laser beam, and low amounts of light scatter to permit visualization of the eye, e.g., through a CCD or CMOS camera or through an operating microscope. The lens may be multi-layered and contain for example a layer of graphene to enhance the heat conducting properties of the lens. The lens is also cooled, for example by one or both of pre-cooling or in situ cooling on the eye. A patient interface for performing in situ cooling is described in FIGS. 5A-5C.

Three-Dimensional Propagation of Thermal Wave Over Time

Figure 4N:
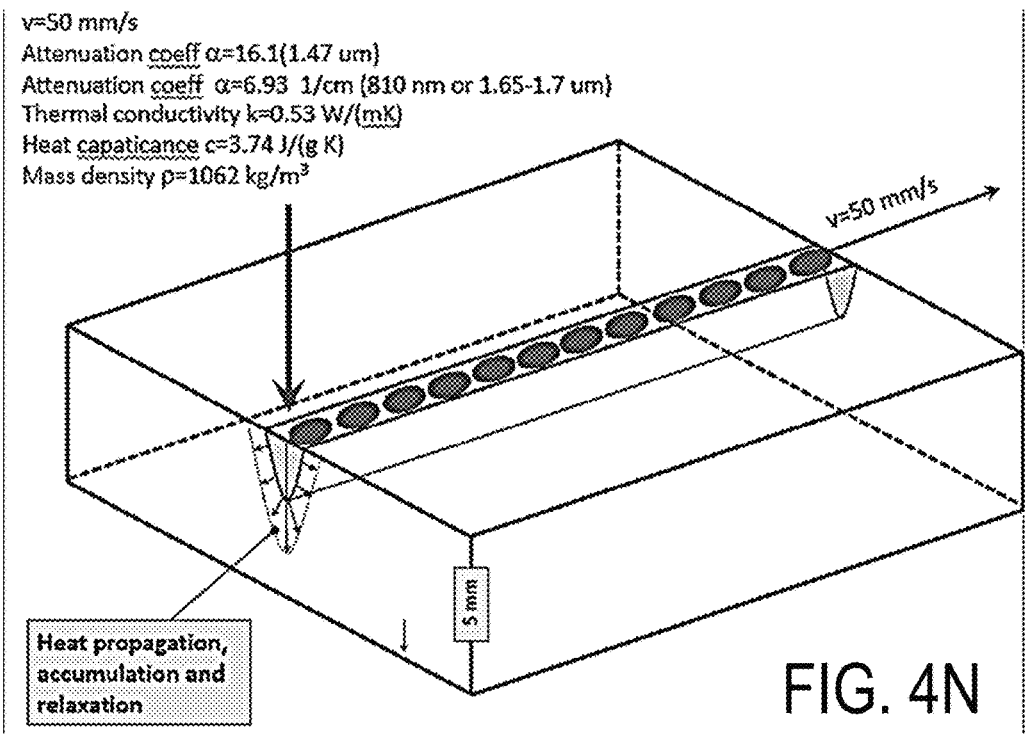
FIGS. 4N, O and P schematically illustrate three-dimensional heat propagation, accumulation and relaxation in the scleral wall as a non-contact laser directed at the scleral surface moves rapidly across the sclera.
Figure 4O:
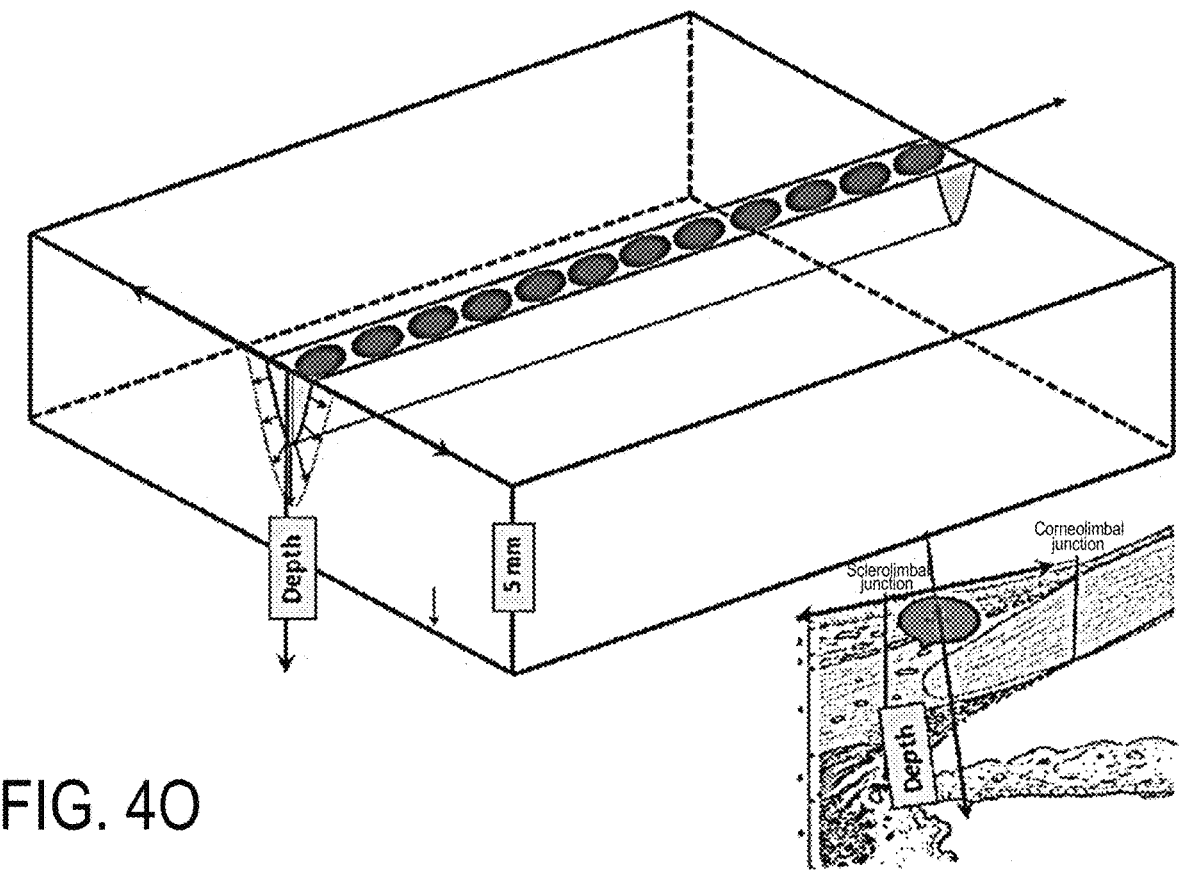
FIG. 4K schematically illustrates angular locations around the right and left eyes.
FIGS. 4Q, R, S, T, U, V, W and X are a two-dimensional illustration of the advance and retreat of the thermal wave through the scleral wall.
FIGS. 4Y and 4Z are graphs illustrating the effect of laser speed and duty cycle on peak tissue temperature.

Propagation of the thermal wave through a section of the scleral wall over time is further illustrated in FIGS. 4N-P. These figures illustrate sequential events caused by laser irradiation on an annulus described by the sliding of a series of interrupted spots from a laser beam moving at a velocity of 50 mm/s across the scleral surface. The laser energy is applied in FIG. 4N generally perpendicular to the scleral surface, and as each laser spot is irradiated heat is propagated in a thermal wave below the scleral surface toward deeper structures. FIG. 4O shows that the thermal wave propagates deeper into the sclera until it reaches targeted sub-scleral structures such as the trabecular meshwork and ciliary body (inset). In FIG. 4P the wave recedes again toward the scleral surface as thermal relaxation occurs. Although this sequence is illustrated for one such spot in FIGS. 4N-P, the same process occurs at each of the laser spots as the laser moves across the scleral surface.

Figure 4R:
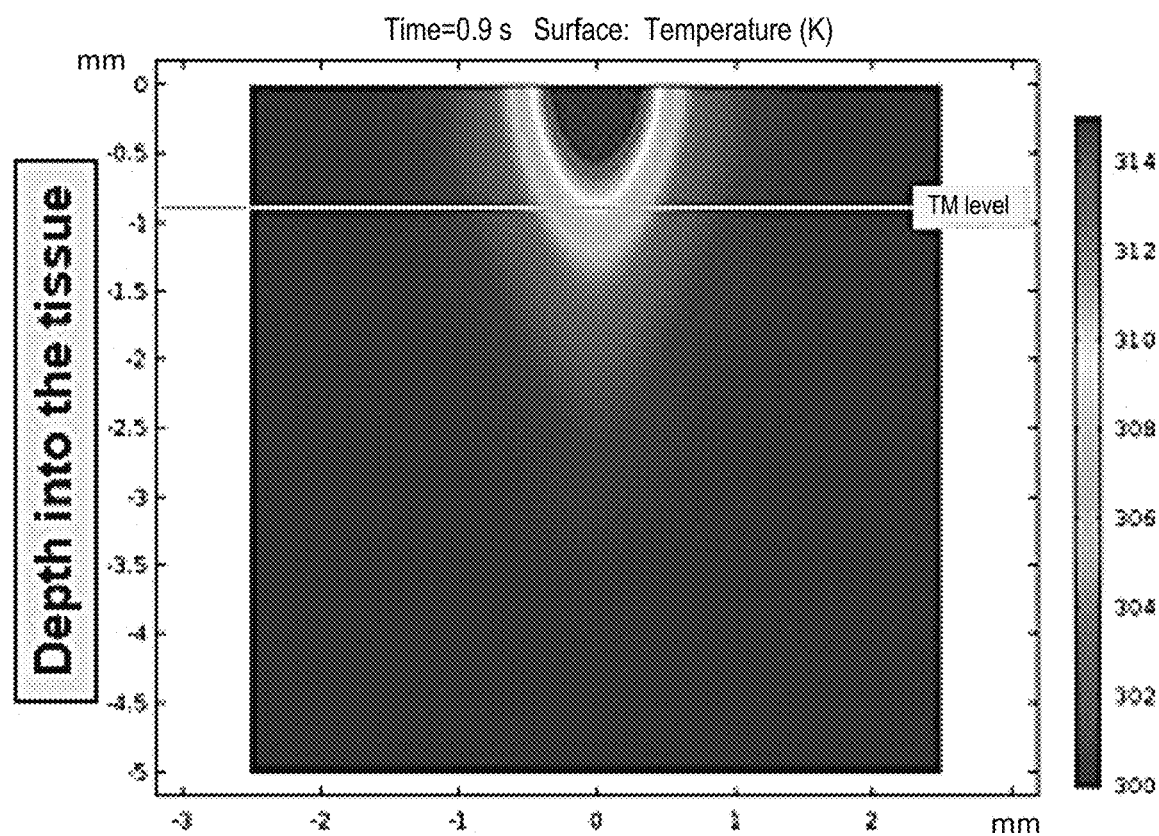
Figure 4S:
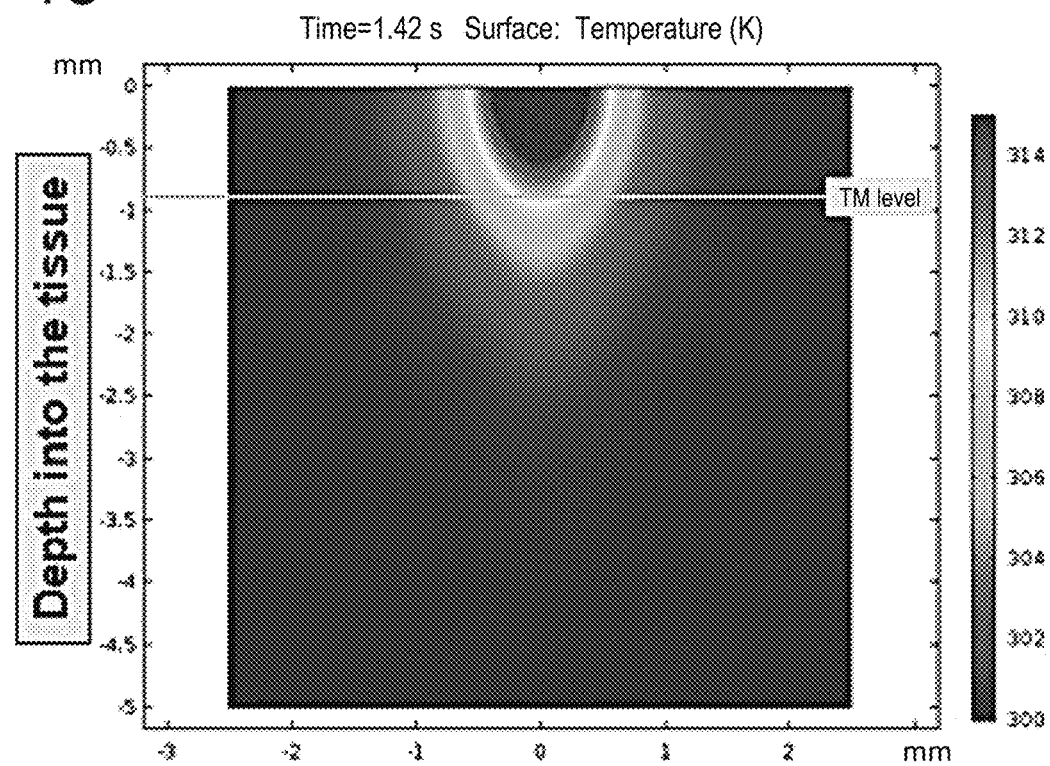
Figure 4T:
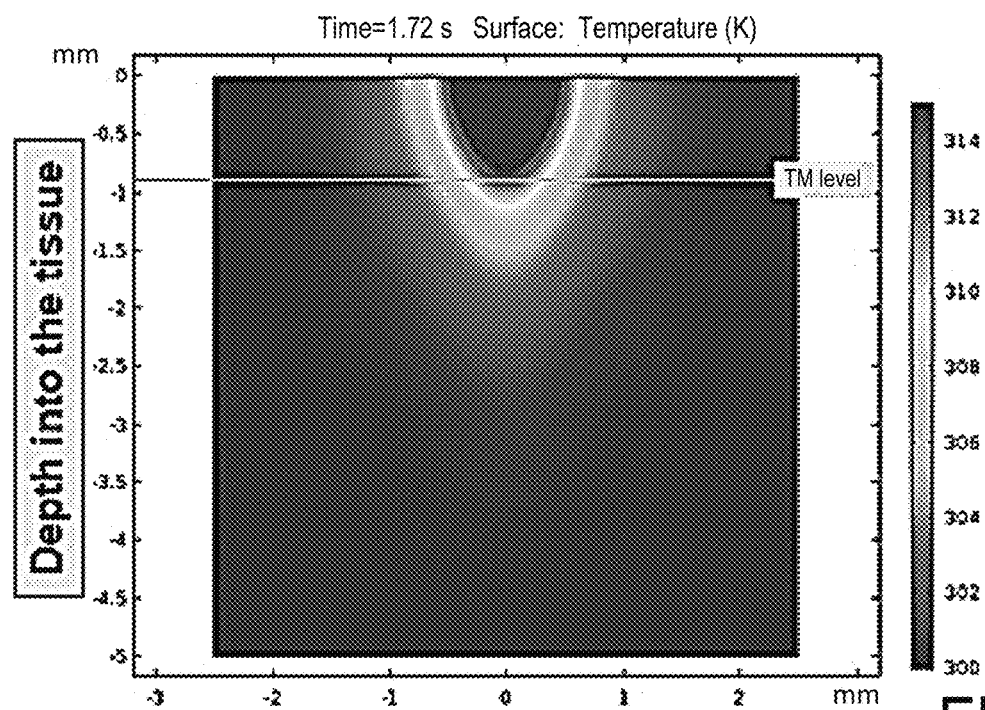
Figure 4U:
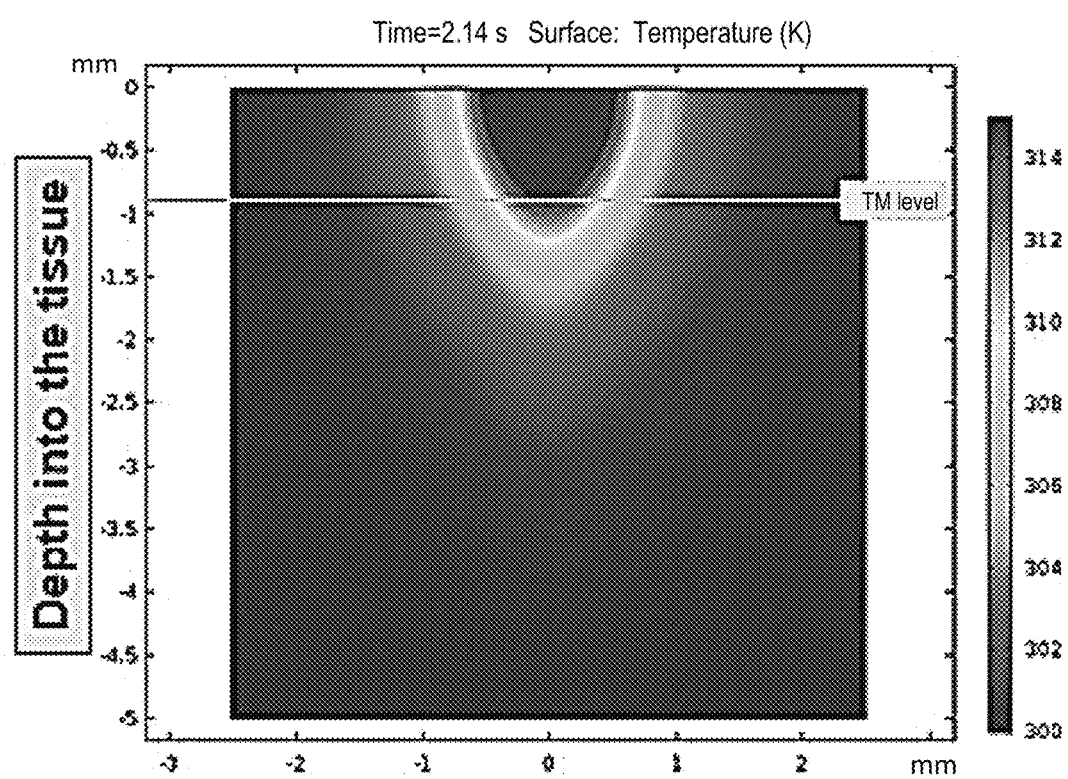
Figure 4V:
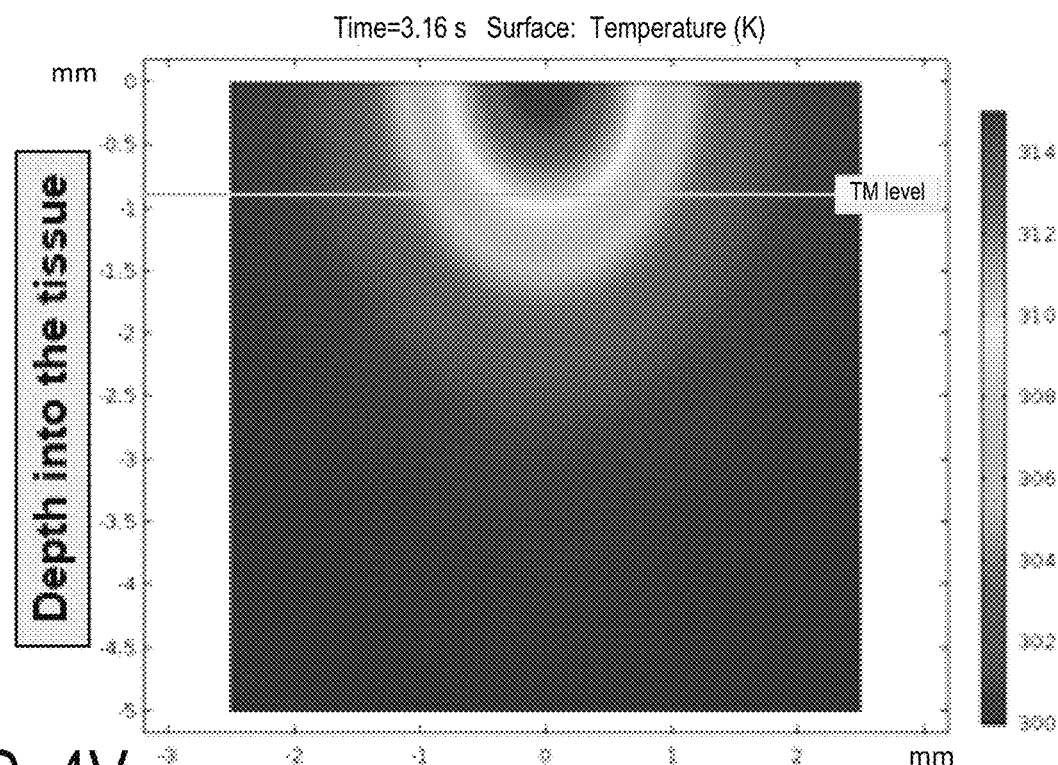
Figure 4W:
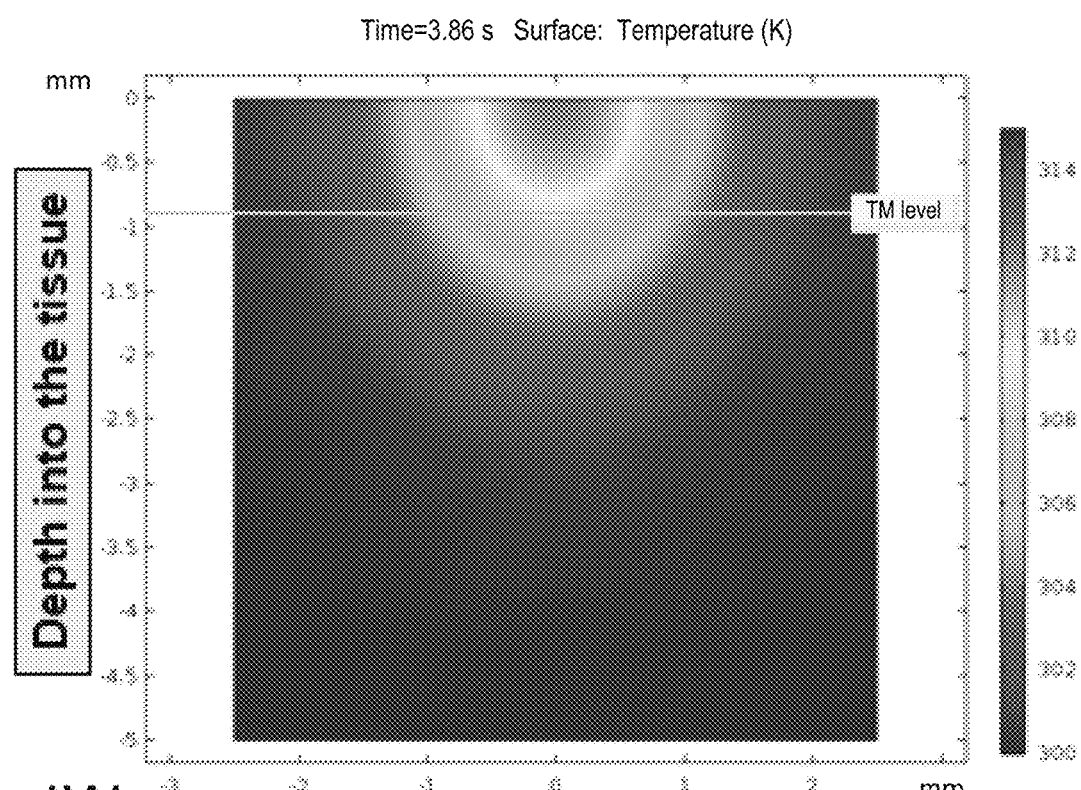
Figure 4X:
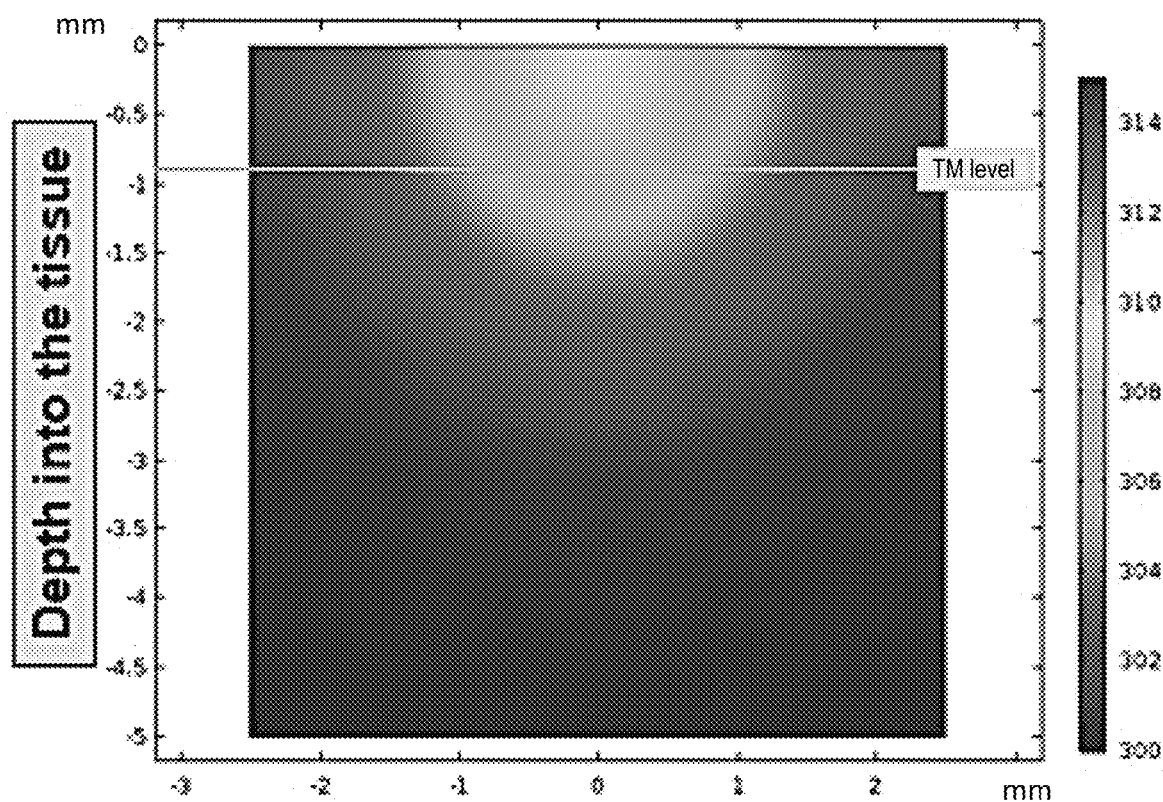
Figure 4X:
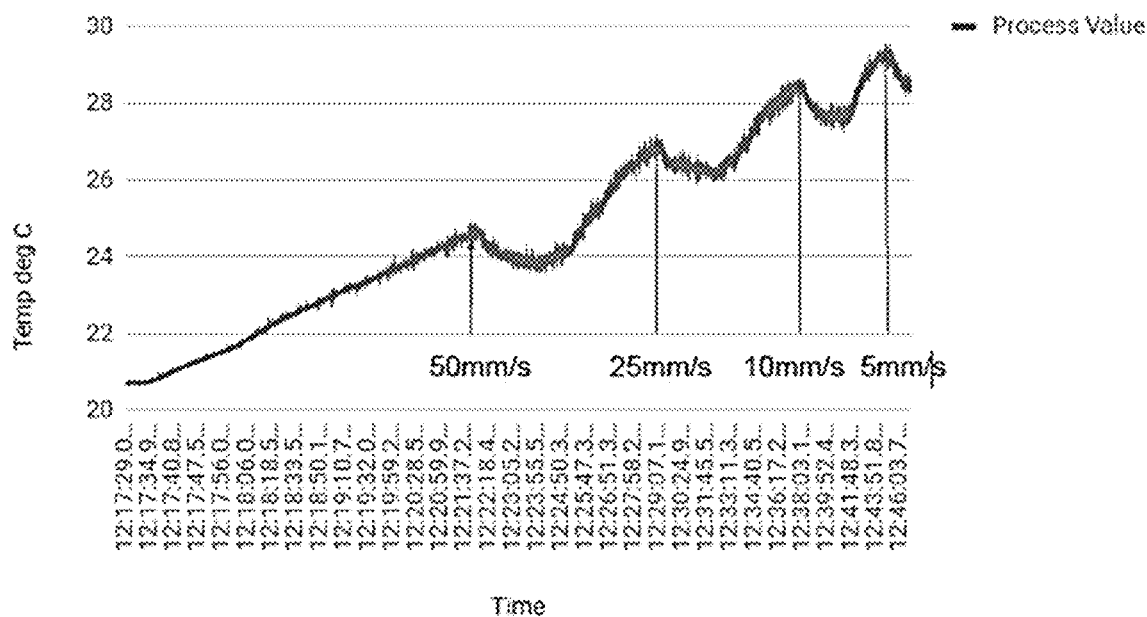

FIGS. 4Q-4X similarly illustrate propagation and retraction of a thermal wave toward and away from the trabecular meshwork (TM level). In FIG. 4Q the thermal wave is propagated at the scleral surface by laser irradiation. In FIGS. 4R, S, T and U the wave progressively advances over the next 1.64 seconds to penetrate and pass into the TM. FIGS. 4V, W and X show a period of thermal relaxation during which the thermal wave moves away from the TM level and back toward the scleral surface.

FIG. 4Y illustrates that peak temperature increase of irradiated tissues can be controlled by altering the speed of laser movement with respect to the sclera. Peak tissue temperatures increase as the speed of laser movement decreases because more energy is delivered to each irradiated lactation, at a constant laser power and duty cycle, per unit time. The graph shows peak temperature changes in irradiated scleral tissue at a laser power of 0.8 W, and a duty cycle of 3.44%, when the laser is moved at 5, 10, 25 and 50 mm/sec through a 200° arc.

Figure 4Z:
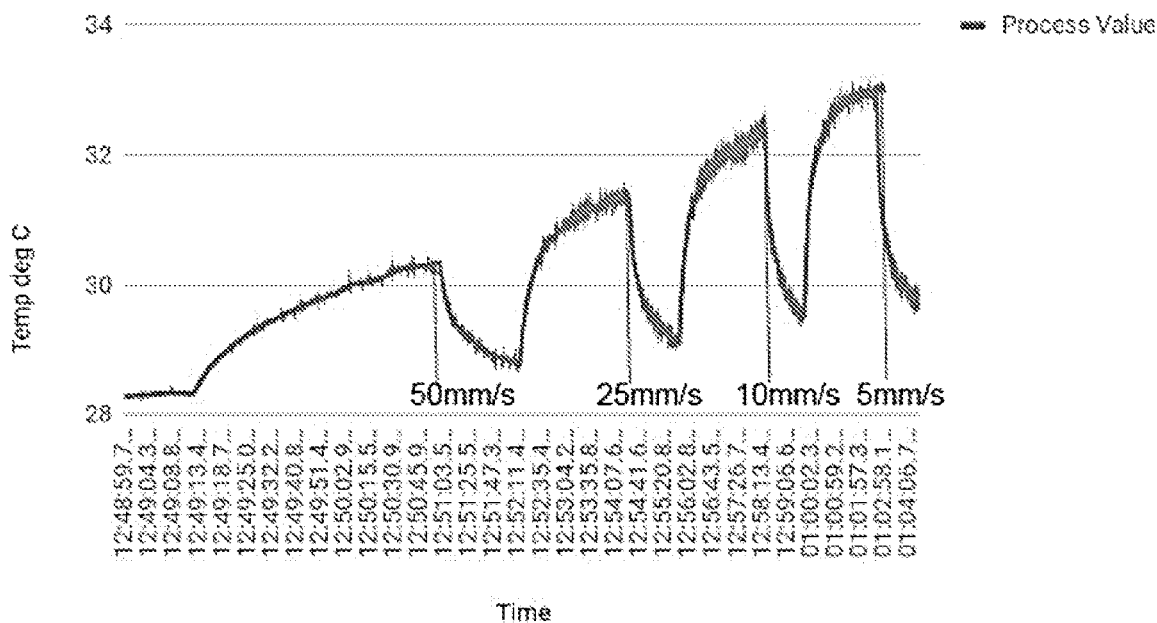
Figure 4Z:
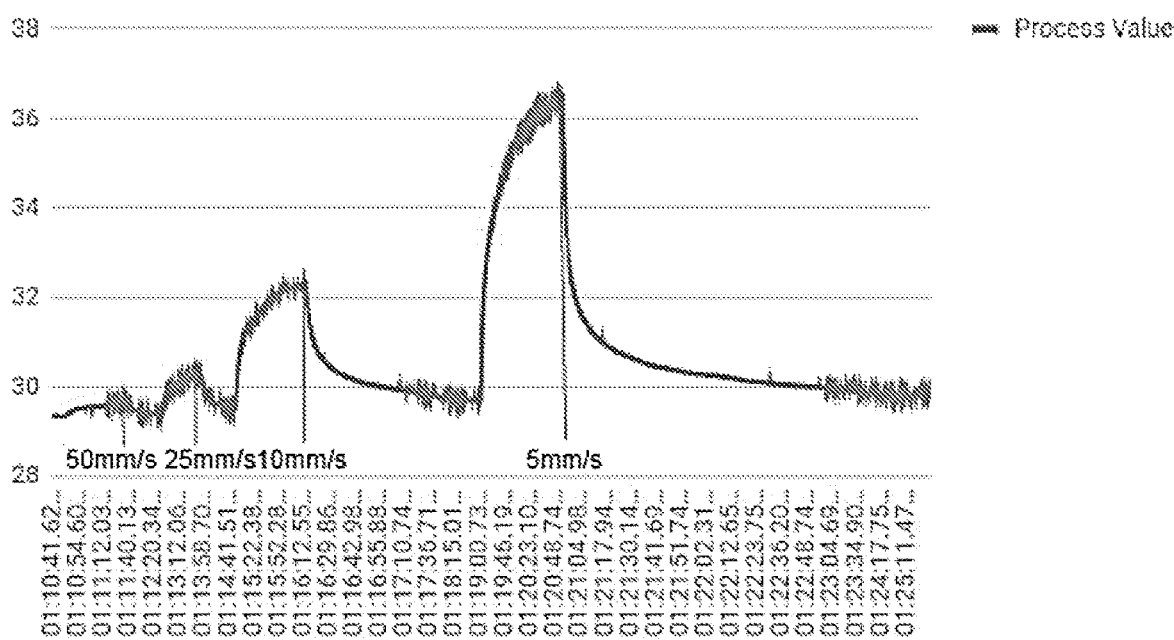

FIG. 4Z illustrates that duty cycle can also be used to control peak tissue temperature in combination with laser speed. In the illustrated example, peak temperatures were compared at a laser power of 0.8 W moving through an arc of 4° with a duty cycle of 11.5% or 172% at a laser speed of 5, 10, 25 and 50 mm/sec. Peak temperature was substantially similar for both duty cycles at 10, 25 and 50 mm/s, but at slow laser speeds of 5 mm/s the peak temperature increased from about 33° C. to 37° C.

Beam Size

The diameter of the laser beam at the surface of the eye is sufficiently large to direct the thermal wave to the targeted aqueous production and/or aqueous outflow structure(s). Beam placement refers to the location of the center of the beam with respect to a reference point. For example, the diameter of the beam may be 500-1000 μm, such as 600 μm. A 600 μm diameter laser beam may be centered on an annular treatment pattern 1.5 mm posterior to the corneolimbal junction to therapeutically stimulate most of the primary aqueous outflow pathway structures with the generated heat and spreading thermal wave. The 600 μm diameter laser beam may also be projected in an annular pattern with the beam centered 3.5 mm posterior to the corneolimbal junction to target the pars plana unconventional uveoscleral outflow pathway. In some embodiments, the 600 μm diameter laser beam may also be projected in an annular pattern with the beam centered 2.5 mm posterior to the corneolimbal junction to target the pars plicata.

The trans-scleral laser cyclic irradiation with a beam of this size causes the localized photothermal elevations that produce biomechanical responses with minute morphologic changes in the microarchitecture of the perilimbal, pars plicata and pars plana regions, with the motion and reorganization of the aqueous humor outflow pathways that enhance both conventional (trabecular meshwork) and non-conventional (uveoscleral) outflows that result in early IOP reduction. The concomitant photo-stimulating hyperthermia (for example to a temperature of 43-45° C.) without photocoagulation of the sclera leads to heat spread and decay in surrounding tissues to re-equilibrate and return the treatment location toward or to baseline body temperature. Although not wishing to be bound by theory, it is believed that the repetitive irradiation and thermal decay triggers bio-chemical responses with a biological cascade of cytokine expression and subsequent endogenous molecular transcriptional activities that contribute to long-lasting IOP lowering effect.

By way of example, the 1.475 μm IR laser wavelength imparts a safe and effective time-temperature-history profile that lowers IOP through one or more of increased trabecular meshwork outflow (trabeculoplasty-effect); increased uveoscleral outflow effect and decreased aqueous humor production (ciliary processes treatment-effect). Different time-temperature-history profiles can produce photocoagulation, photostimulation and hyperthermia without undesirable tissue coagulation by thermally-preconditioning the scleral tissue to induce thermotolerance. The thermotolerance is a temporary state of resistance to heat-induced cellular death, and the thermotolerance is achieved by the repetitive irradiation of treatment locations at spaced intervals and gradually increasing temperatures. The gradual increase in tissue temperatures is believed to activate natural protective mechanisms, such as auto-thermo-regulation and production of heat shock proteins, that ultimately increase the thermotolerance of the tissue and that have repairing and regenerative effects on surrounding dysfunctional cells. Thermotolerance permits a treatment location to be irradiated repeatedly while minimizing tissue damage to the treatment location.

Irradiance, Scanning Speed, Exposure Time, Cycle Repetition Rate

The combined therapeutic effect and protective thermal-preconditioning are controlled by a variety of factors that control the temperature generation-re-equilibration photothermal process. These parameters include the laser power (W) and irradiance (W/cm$^2$), exposure time (scanning speed in mm/s), and the cycle repetition rate (the period T between two consecutive exposures at the same cellular spot) which determines the duty factor: ON time/Period T (%) and number of cycle repetitions (total treatment duration). The laser beam may be projected through a limbal-guided scanning computer-controlled electro-optical delivery system to irradiate the sclera in the different arc patterns at the different distances posterior to the limbus at programmed scanning speeds (exposure time) and other selected variables to create unique time-temperature histories with photothermal elevations that concomitantly produce IOP lowering biomechanical and biochemical responses.

The laser irradiance (power over unit of area in W/cm$^2$) and the scanning circular speed (mm/s) may be selected to create a temperature rise within 8-20° C. above the 37° C. body temperature in the sclera when irradiated by the scanning laser beam, for example a 0.6 mm diameter laser beam. Given the absorption coefficient of the 1.475 μm IR wavelength in the sclera (18.8 cm$^{-1}$) the temperature of the first 200 μm deep scleral layers (from the conjunctiva through a scleral depth of 160-200 μm) can be elevated to about ≈45°-57° C. (37°+8° or 20°) by controlling laser irradiance (W/cm$^2$) and exposure duration (which is determined by the scanning speed in mm/s and by the number of repetition). To reduce the risk of cumulative thermal damage to the superficial first absorbing layers of the conjunctiva and sclera, the laser power for the first treatment cycle may be set to start at a fraction (such as less than 50%, 40%, 30% or 20%) of the threshold power that would cause an immediate coagulation reaction. At the completion of the first cycle, the laser power is automatically step raised at each successive cycle (for example to 25% at the 2$^{nd}$ cycle, to 30% at the 3$^{rd}$ cycle and to 35%, 40%, 45%, 50%, 55%, 60%, 65%, 70%, 75%, 80%, 85%, 90%, 95% at each successive cycle) to reach the 100% at the 17$^{th}$ cycle without causing any visible coagulation effect due to the thermoconditioning process that increases the thermotolerance or resistance to heat cellular death. In an alternative example, the targeted peak temperature may be rapidly reached and then decreased to maintain the dwelling period at the peak temperature elevation.

If the electro-optical scanner moves the beam at a constant circular speed of 50 mm/s around a treatment annulus, each portion of the scleral annulus irradiated by the 0.6 mm diameter beam receives an exposure duration of 12 ms (0.6 mm 50 mm/s=0.012 s) that causes the local temperature to rise. As the laser beam moves away, the exposure and the heat production are terminated, but the generated heat spreads and decays toward adjacent surrounding cooler tissues in a thermal relaxation process to eventually re-equilibrate with the body baseline temperature (37° C.). This thermal relaxation process is interrupted when the laser beam is returned to the same spot after having completed the 360° cycle and begins the next cycle, converting the thermal relaxation into a new temperature increase. In one example, with treatment in a circular pattern having a 13 mm diameter and a 40 mm circumference, each cycle will take about 800 ms (40 mm÷50 mm/s=0.8 s) irradiating with a 1.5% duty factor (12÷800=0.015 or 1.5%).

In some examples, the exposure duration of each portion of the scleral annulus is about 2-120 ms, for example 2-20, 10-20, 10-15, 12, 24, 60 or 120 ms. In some examples with a constant 0.6 mm (600 μm) beam diameter spot size, the duration of the irradiation at each point in the middle of the annulus width may depend on the beam circular scan speed: at 1.0 mm/s the irradiation time at each cycle is 0.6 s or 600 ms; at 5.0 mm/s the irradiation time at each cycle is 0.12 s or 120 ms; at 10.0 mm/s, 60 ms; at 15.0 mm/s, 40 ms; at 20.0 mm/s, 30 ms; at 25.0 mm/s, 24 ms; at 30.0 mm/s, 20 ms; at 50.0 mm/s, 12 ms; at 100.0 mm/s, 6 ms; at 300.0 mm/s, 2 ms.

The process is continued for N cycles to sustain the thermal elevation for the programmed time-temperature history. In addition to the thermal preconditioning that enhances the thermotolerance of the scleral first energy absorbing layers, heat may also be continuously subtracted from the conjunctival/scleral superficial layers by the heat sink, such as a chilled contact lens that cools, protects, and spares those superficial layers from cumulative thermal damage. The heat sink allows the duration of the temperature elevation to be prolonged for the time needed to permit its decaying heat-wave to reach the deep targets at the selected photo-thermal-stimulation temperature and sustain the propagation of heat waves for the duration required for an effective hyperthermia therapy, for example 25 seconds or more.

The system described herein can therefore induce the therapeutic photothermal effects without the use of contact probes having protruding fiberoptic tips that are dragged along the eye to potentially cause discomfort and scratch the sclera. The non-contact laser source may also be moved at a more rapid velocity through the treatment pattern than could generally be achieved with a contact probe moving against the eye. The automated or computer-implemented features of the system also help achieve more consistent treatment that avoids subjective variations in precisely positioning and controlling the speed of laser energy delivery. The trans-scleral cyclic laser therapy does not require retrobulbar block. It is also more efficient because it non-specifically converts electromagnetic energy into heat in cellular water, and not only in pigmented cells. The cyclic laser therapy also produces beneficial photothermal stimulation/hyperthermia by modulating the time-temperature-history of the tissue, for example through computer-controlled laser power, the beam moving speed (laser "ON" exposure time) and the cycle repetition time (Period T and duty factor) and the number of repeated cycles (duration of the sustained hyperthermia).

Patient Interface

In some examples, the system includes a patient interface for docking the non-contact laser energy source spaced away from the eye. The patient interface may include a spacer that maintains the eye in a substantially fixed location and/or focal distance for imaging and treatment. The spacer may, for example, be in soft contact with the surface of the eye and maintain the laser energy source spaced from (not contacting) the surface of the eye. The patient interface may further include a speculum for placement between the eyelids of the subject to keep the eye open and better expose the eye (particularly the sclera) to the laser energy. In some embodiments the patient interface includes a lens holder that stably positions a contact lens over the surface of the eye to serve as a heat sink and conduct heat outwardly away from the eye. For example, the lens may be a scleral contact lens that contacts the sclera at the treatment locations. In disclosed embodiments the contact lens holder may also include a fixation ring having a resilient sealing face to seat against the eye, and the system may be configured to maintain adjustable negative pressure within the fixation ring between the eye and contact lens to secure the patient interface to the surface of the eye and substantially immobilize the eye of the subject during the procedure.

In some examples a positioning arm positions the patient interface at a treatment orientation to the surface of the eye of the subject in a selected treatment orientation. The positioning arm may be driven by an X-Y-Z controller that precisely aligns and registers the spacer and ring in contact with the eye to precisely apply the laser energy to the eye.

The spacer and/or fixation ring may be cooled to protect the superficial layers of the sclera from thermal damage during laser irradiation of the eye. For example, internal flow channels are present in the spacer and/or lens holder, and the system is configured to introduce a cooled fluid (such as water or saline solution) through the fluid flow channels to cool the spacer and/or fixation ring and/or contact lens.

The spacer can dock to the lens holder for holding a laser output the spaced distance from the contact lens heat sink. The resilient sealing ring on the lens holder, which extends around the contact lens to create a sealing chamber between the contact lens and the eye, retains the lens holder against the eye to substantially immobilize the eye when a suction is applied to the sealing chamber or at least neutralize differential movement of the eye with respect to the laser. The sealing chamber under the lens communicates with a suction port through which negative pressure is selectively and/or adjustably applied to the sealing chamber to optionally secure the lens holder to the eye to control eye movement during the procedure. A laser triangulation system provides Z-focus camera viewing of the contact lens, and the X-Y-Z positioner positions the patient interface with the sealing ring of the lens holder against the eye of the subject, with the spacer docked to the lens holder.

In some examples, the patient interface assembly includes a spacer cone, such as a frustoconical spacer that tapers from an enlarged first face to a smaller second face. A laser emission source (such as an objective lens) is carried by the cone and spaced away from the smaller second face. The lens holder is a collar that tapers from a larger first face of similar shape and size to the second face of the spacer with which it docks, to a smaller second face of the lens holder collar that is circumscribed by a resilient patient fixation ring to form the seal against the eye to be treated. The lens holder collar includes an internal cooling fluid passageway, an inlet port and an outlet port for circulating cooling fluid through the collar. The heat sink contact lens is retained in the fixation ring and forms the suction chamber between the contact lens and the eye when the collar is docked against the eye of the subject and air in the suction chamber is withdrawn from the chamber. The suction applied by the suction chamber may be varied depending on clinical circumstances. For example, to avoid any potentially damaging IOP elevation in the patient's eye, the vacuum can be very low or not used at all.

In methods of using the patient interface, the blades of the speculum are inserted into the eye to separate the eyelids to expose the sclera. The lens holder is retained between the blades of the speculum and air is optionally suctioned from the sealing chamber. The X-Y-Z positioner is adjusted to dock the spacer to the lens holder, and cooling liquid is introduced through the internal cooling channels of the lens holder via the fluid inlet and outlet ports. The contact lens and eye may be viewed with optical viewing software and a laser treatment of the eye performed through the patient interface, with the laser held in a spaced relationship to the sclera.

Figure 5A:
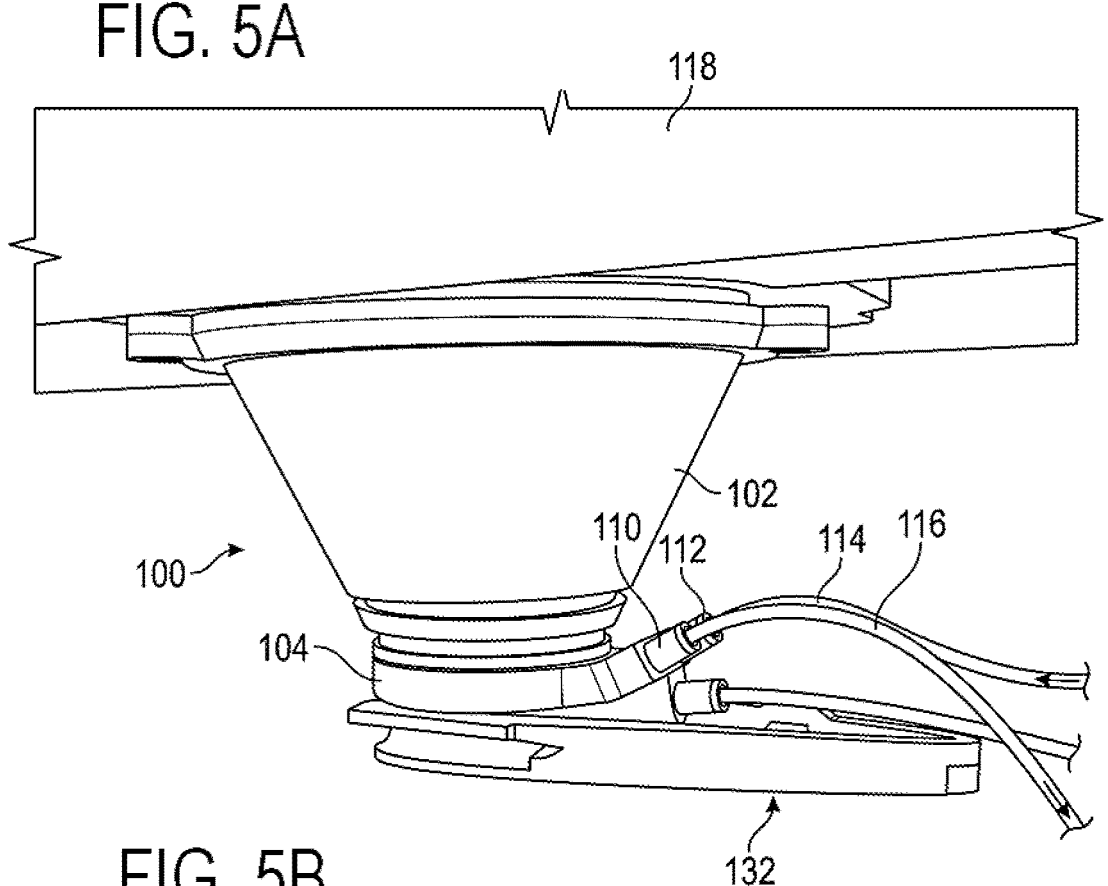
FIG. 5A is a perspective view of a patient interface for stabilizing and cooling the eye during the trans-scleral procedure.
Figure 5B:
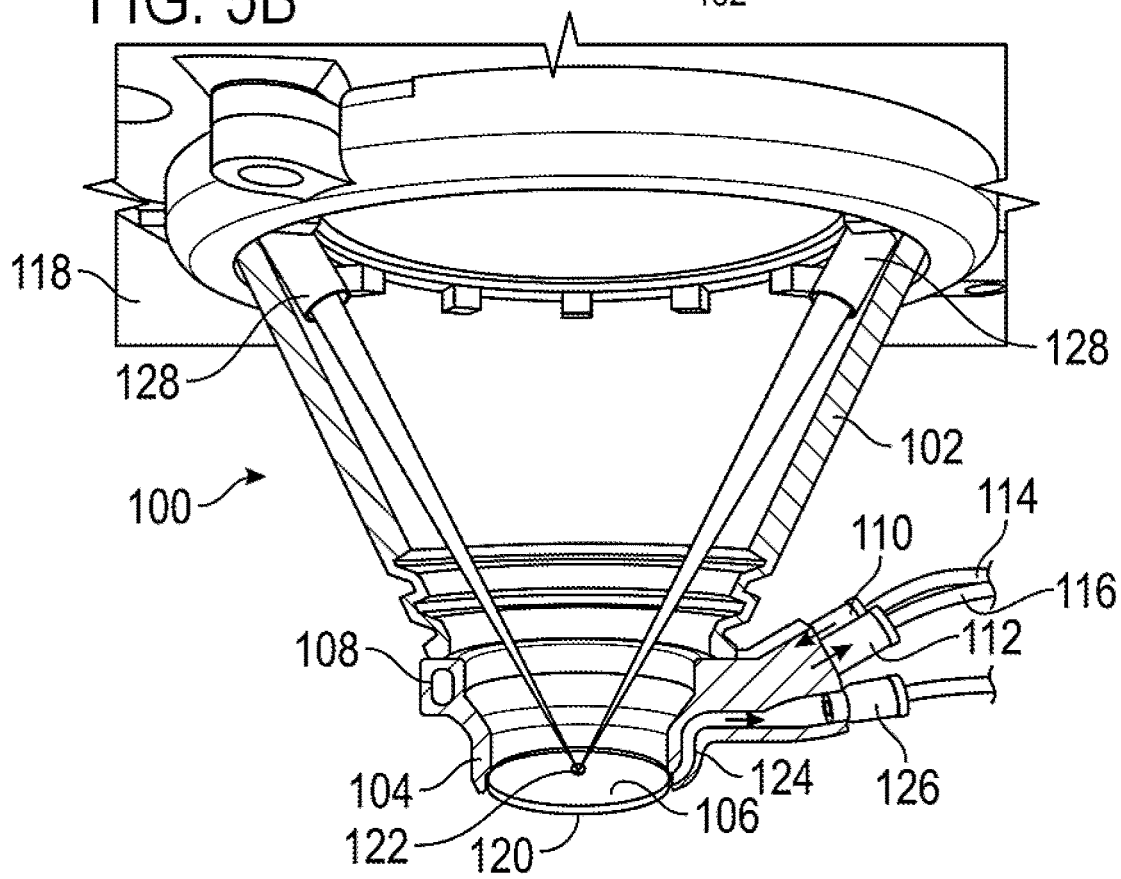
FIG. 5B is a cross-sectional view of the patient interface illustrating a graphene contact lens held by a contact lens holder that cools the lens and permits suction contact between the lens holder and the eye. Laser triangulation for Z-focus camera viewing is also illustrated.
Figure 5C:
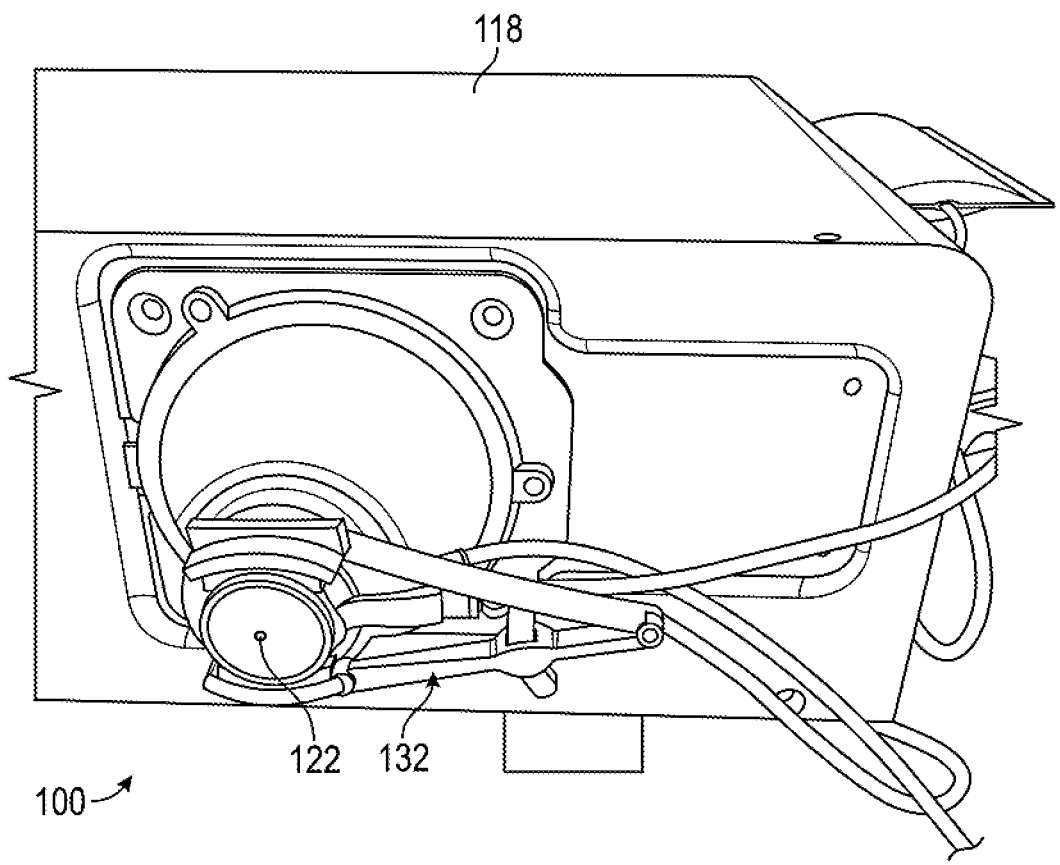
FIG. 5C is a bottom perspective view of the patient interface, showing the graphene contact lens surrounded by a silicone sealing member.

The spacer permits therapeutic laser energy to be applied to the eye from a laser energy source spaced from the surface of the eye. A specific example of such a device is shown in FIGS. 5A, 5B, and 5C in which a patient interface 100 docks the laser treatment device to an eye to be treated. Interface 100 includes a spacer 102 and lens holder 104. The lens holder 104 is configured to retain a heat sink, such as an ophthalmic contact lens 106 against the surface of an eye to be irradiated. In the illustrated embodiment the lens has a radius of curvature of about 11.5 mm and a diameter of about 15-20 mm. The lens may be a scleral lens that has an apical clearance of the cornea (for example a 1 mm apical clearance), and the peripheral edge of the lens seats against the sclera. The lens vaults over the eye to form a suction chamber.

As shown in FIG. 5B, a resilient sealing ring 120 circumscribes the peripheral edge of contact lens 106 to establish a seal between contact lens 106 and the surface of an eye to which contact lens 106 is applied. The radius of curvature of lens 106 may be greater than the radius of curvature of the cornea over which it is placed so the lens 106 vaults over the eye to form a suction chamber 123 within sealing ring 120 between contact lens 106 and the surface of the eye to which contact lens 106 is applied. A small central hole 122 in contact lens 106, for example having a diameter of 0.5 mm-2 mm or 0.5-1 mm, permits air and tear fluid to move through lens 106. As shown in FIG. 5B, a suction passageway 124 extends through a wall of lens holder 104 and communicates with an external suction port 126. Hole 122 in lens 106 permits air to pass into sealing chamber while still maintaining the negative pressure in the sealing chamber. A video camera displays docking contact proximity by triangulating on hole 122 with two low power laser spots as they converge displaying approaching proximity sensing of cone contact lens to patient eye. The triangulation laser spots generated by laser emitters 128 are coincident at the contact lens center in the treatment eye focus-plane.

The inner face of contact lens 106 that is placed against the eye may be a graphene face to enhance the heat sink properties of the lens, as disclosed in greater detail in US 2018/0177632. There are internal cooling channels 108 (FIG. 5B) within lens holder 104 that communicate with fluid flow inlet port 110 and outlet port 112 to circulate cooling fluid (such as chilled water) from inlet line 114, through channels 108, and into outlet line 116. Spacer 102 is secured to a control box 118 containing a laser source that is controllable to target laser beam 82 (FIG. 4M) through the chamber within spacer 102 and toward contact lens 106. Laser beam 84 may be controlled, for example, to move it through an arcuate path 84 (FIG. 4M and FIG. 8A) that directs laser energy toward the eye to irradiate the eye in the annular treatment pattern. Laser beam 84 passes through contact lens 106 to induce a targeted hyperthermia with the selected time-temperature history response in the sclera and/or in the retina of the treated eye that propagates the thermal wave to adjacent tissues in the eye. Angles of incidence can depend on the selected treatment locations. For example, impingement of a treatment beam at the sclera can be normal to the tangent of the sclera (or otherwise at an angle that is not parallel to the optical axis of the eye) and impingement of a treatment beam that passes trans-pupillary through the pupil will generally propagate parallel to the optical axis (or close to parallel) to treat pan-macular annuli concentric to the foveal avascular zone or other fundus features. A common lens can be used for beam delivery or alternative lenses may be used in some examples, in providing a larger angle of incidence at scleral treatment locations. In further examples, a mirror surface similar to a gonioscopy lens delivery configuration may be used to provide ab externo delivery to the sclera, such as by having a conical reflective inner surface of the patient interface 100 (such as with the conical spacer 154 discussed below).

Figure 6A:
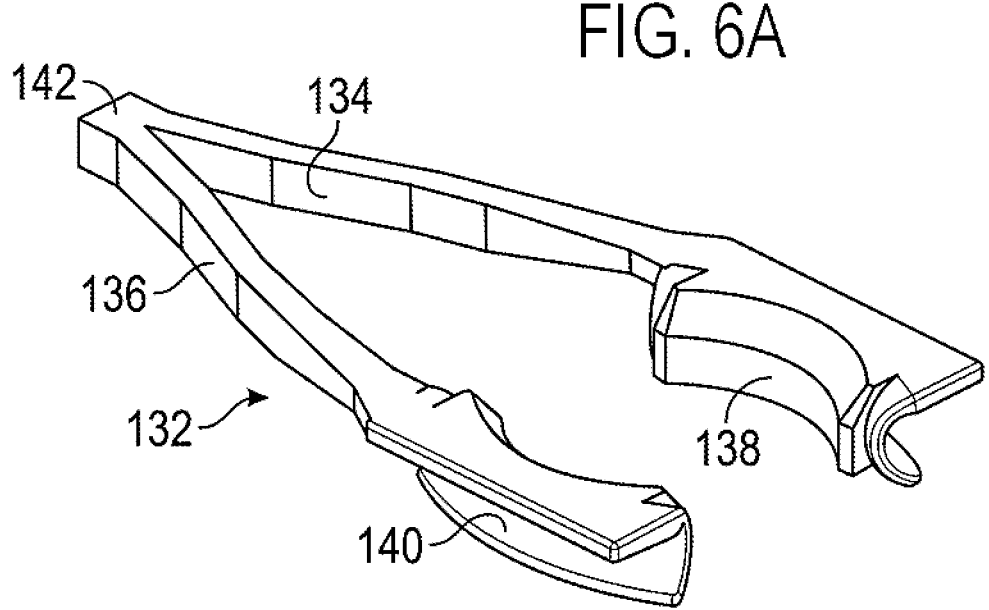
FIG. 6A is a perspective view of the speculum.
Figure 6B:
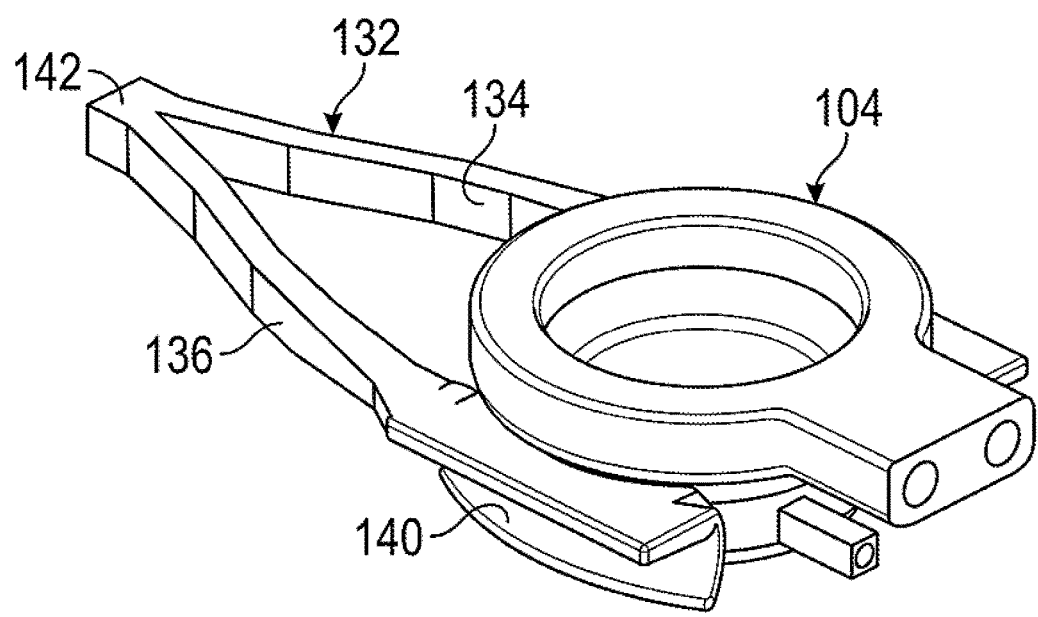
FIG. 6B is a perspective view of an embodiment of the contact lens holder retained within the speculum.

Interface 100 may also include an eye speculum 132 (FIGS. 6A and 6B) that includes a pair of opposing plastic arms 134, 136 that are joined at a flexible pivot point 142 that biases arms 134, 136 to the open positions shown in FIGS. 6A and 6B. The unjoined open ends of arms 134, 136 each carry curved a speculum blade 138, 140 that are configured to fit within the palpebral fissure of the eye. Speculum 132 is sufficiently flexible about pivot point 142 that the speculum arms 134, 136 may be moved toward one another to narrow the distance between blades 138, 140 and facilitate insertion of the speculum into an eye to better expose the sclera that is to be irradiated. The outward bias of arms 134, 136 will return the arms to the open position shown in FIGS. 6A and 6B to maintain exposure of the targeted eye tissue to be treated. Different size speculums may be used to open the eyelids to a preselected distance, for example 20 mm, 22 mm or 24 mm at the point of greatest separation between the eyelids.

Figure 6C:
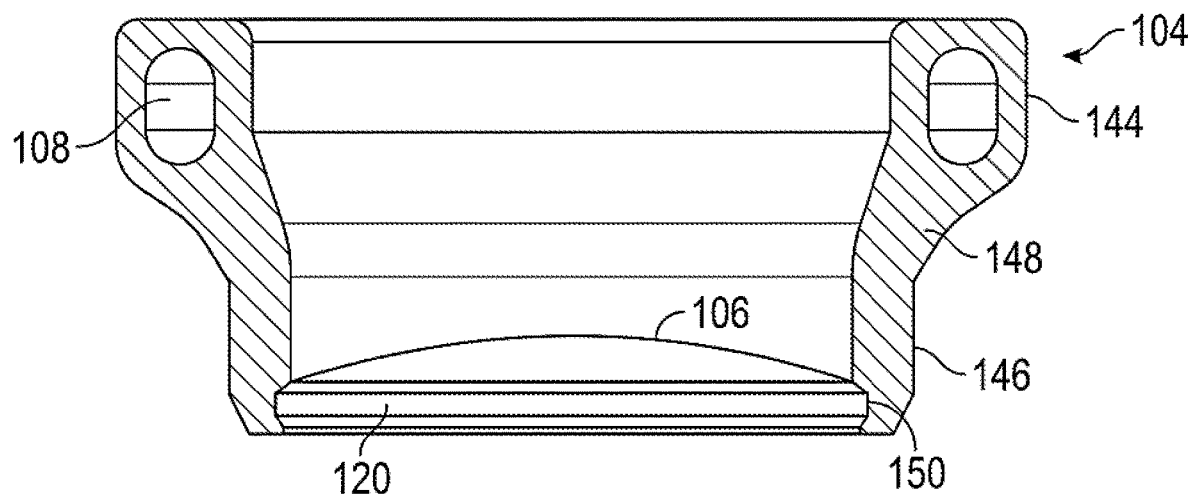
FIG. 6C is an isolated cross-sectional view of the contact lens holder with an internal cooling channel to circulate cooling fluid and cool the contact lens.

Speculum 132 is also configured to conform to and secure collar 104 between blades 138, 140. As shown in FIG. 6C, collar 104 includes a substantially cylindrical top portion 144 and a substantially cylindrical lower portion 146 joined by an angled shoulder 148 that narrows the inner diameter of collar 104 from the top portion to the bottom portion. Internal fluid passageway 108 extends circumferentially around top portion 144. Resilient sealing ring 120 seats in a circumferential recess on the inner face of lower portion 146 to hold heat sink contact lens 106 centered in the lower open face of collar 104, with central hole 122 of the contact lens substantially at the center of the face. FIG. 6D is an exploded view of interface 100 that shows how spacer 102, collar 104 and speculum 132 are assembled. Collar 104 is placed between blades 138, 140 of speculum 132 and the inner faces of the speculum blades conform to the external cylindrical surface of lower portion 146 of the collar to engage and retain the collar between the blades. Spacer 102 may then be docked against collar 104.

An example of spacer 102 in FIG. 6D has a shape that tapers from an open top face circumscribed by circular lip 150 to a narrower bottom face circumscribed by a circular lip 152 that mates with top portion 144 of collar 104. Spacer 102 includes an upper generally cylindrical collar 152 joined to a frustoconical middle section 154 that tapers to a docking section 156 from which depend snap-fit members 158 to engage the inner face of portion 144 of collar 104 and retain spacer 102 in selective engagement with collar 104. Snap-fit members 158 are coupled to complementary members inside collar 104 for releasably interconnecting spacer 102 and collar 104 with a compression fitting for conveniently connecting and disconnecting the spacer and collar. In other embodiments, snap-fit connections between spacer 102 and collar 104 are not used, and spacer 102 is instead soft-docked against collar 104 using an X-Y-Z positioning system and imaging system.

Figure 6E:
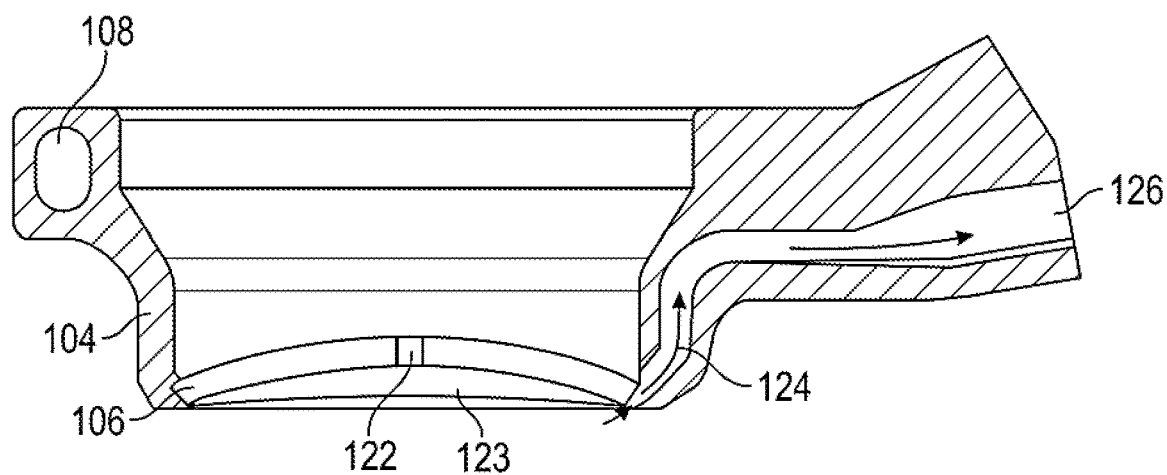
FIG. 6E is an enlarged side-sectional view of the lens holder showing the contact lens vaulting over the suction chamber.

FIG. 6E is an enlarged view of collar 104 with the peripheral edge of contact lens 106 seated in an internal lip of collar 104 with central hole 122 centered in collar 104. Suction chamber 123 is formed below contact lens 106, and chamber 123 communicates with suction line 124 through an opening in collar 104 below the peripheral edge of contact lens 106. External suction port 126 draws a suction through line 124 to establish suction between contact lens 106 and the surface of the eye to retain collar 104 and patient interface 100 relatively immobile against the eye.

Figure 7A:
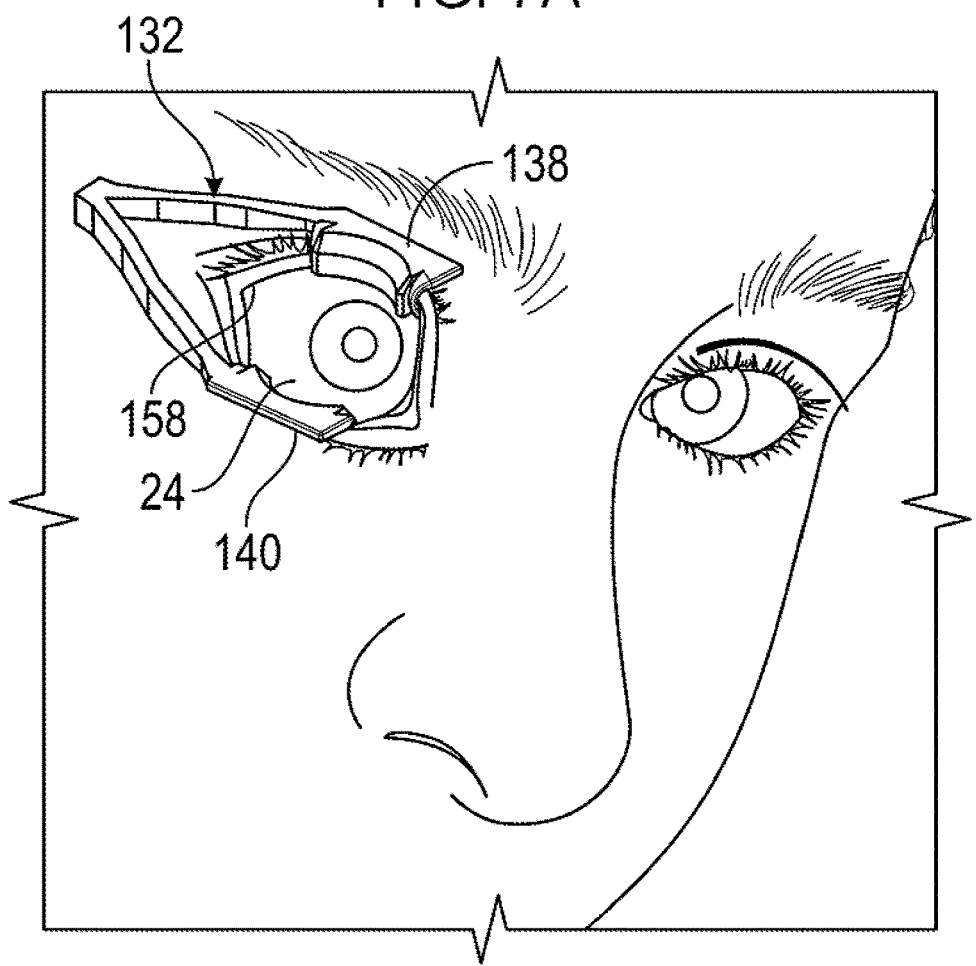
FIG. 7A illustrates the speculum as it would be placed in a subject's eye to expose the sclera for the trans-scleral procedure.
Figure 7B:
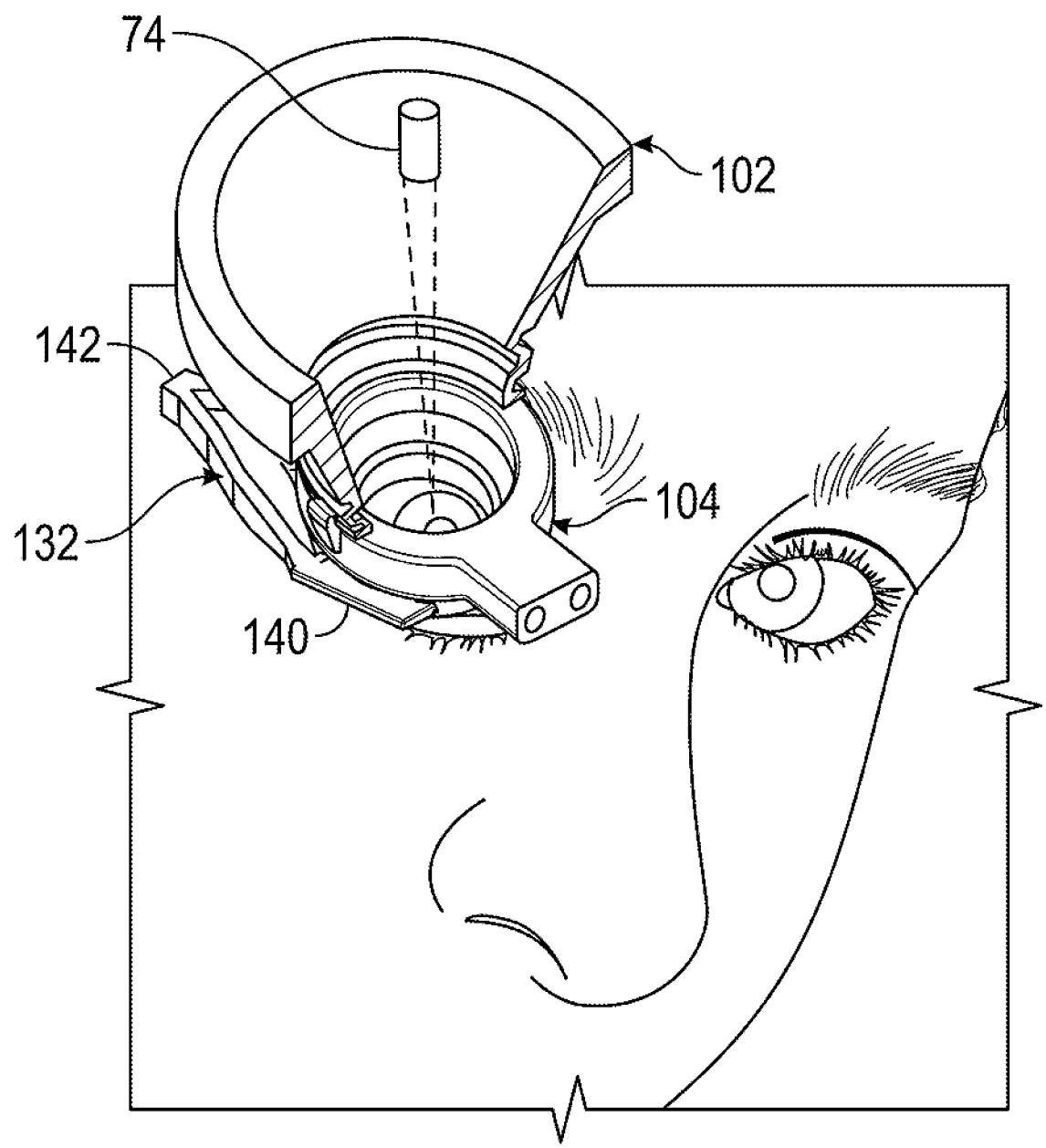
FIG. 7B schematically illustrates the assembled patient interface in the eye. Typically the interface would be inserted in the eye of a recumbent person, but for purposes of illustration a perspective view has been shown.

FIG. 7A illustrates speculum 132 positioned in the palpebral fissure 158 of a subject to expose sclera 24 for treatment. FIG. 7B shows assembled interface 100 with spacer 102 docked against collar 104, and collar 104 itself retained between blades 138, 140 of speculum 132 with contact lens 106 placed against the surface of the eye (for example the cornea and/or sclera). Interface 100 substantially immobilizes the eye of the subject being treated to inhibit differential motion of an eye with respect to a laser beam directed toward the eye from a laser energy source 74 spaced outwardly from the surface of the eye. Control of eye movements is particularly effectively achieved by suctioning air from the suction chamber within sealing ring 120 below contact lens 106. Suction may be guided by clinical circumstances. For example, the procedure may be performed without suction or with suction. When suction is applied, the negative pressure in the suction chamber is controlled for example to under 35 mm Hg. Gentle levels of suction are preferred that do not increase IOP by more than 5 mm Hg. Central hole 122 of contact lens 106 permits an inflow of air into the suction chamber to help regulate the pressure in the suction chamber in combination with the outflow of air from the chamber induced by the applied suction.

The patient interface 100 improves detection of the limbus and/or corneolimbal junction with an optical imaging system. Differential movement of the eye with respect to the laser beam may be minimized by also using patient interface 100 (FIG. 8A) to control relative movement of the eye to avoid interfering with targeted delivery of the laser energy. The resilient sealing face of sealing ring 120 is seated against the eye and suction is drawn between lens 106 and eye 70 to minimize the differential eye movement. Patient interface 100 may also maintain the non-contact laser energy source or optic 74 at a predetermined distance from and not contacting the surface of eye 70.

The laser energy may be trans-sclerally delivered by the patient interface under spatial and temporal processor control while cooling the surface. For example, a method is performed with a computer-driven electro-optical scanning beam delivery system 200 (FIG. 8B) designed for limbus-guided non-contact trans-scleral cyclo-deposition of infrared (I.R.) electromagnetic energy (for example 1.475 µm laser energy) in arcuate or circumferential arc patterns at selectable scleral meridian positions posterior to the anterior (apparent) limbus over i) perilimbal outflow structures (collector channels, Schlemm's canal, trabecular meshwork); ii) pars plicata ciliary body; and iii) the pars plana uveoscleral region. The scanning speed is adjustable, for example within the range of 0.1-50 mm/s.

The amount of infrared laser energy delivered may be titrated with the laser irradiance (W/cm$^2$) and the exposure duration (by controlling the cyclic scanning rotational speed in mm/s) to produce localized photo-thermal elevations, which are non-coagulative, but that may induce biomechanical responses with minute morphologic changes to the microarchitecture of the perilimbal, pars plicata and pars plana regions, that result in reorganization of the aqueous humor (AH) outflow pathways that enhance both conventional (trabecular meshwork) and non-conventional (uveoscleral) outflows. The method also induces biochemical responses elicited by a concomitant photo-stimulating hyperthermia (43-45° C.) as the heat spreads and decays in surrounding tissues to re-equilibrate and return to baseline body temperature, which triggers a biological cascade of cytokine expression and subsequent endogenous molecular transcriptional activities that contribute to long lasting IOP lowering effect.

Figure 8A:
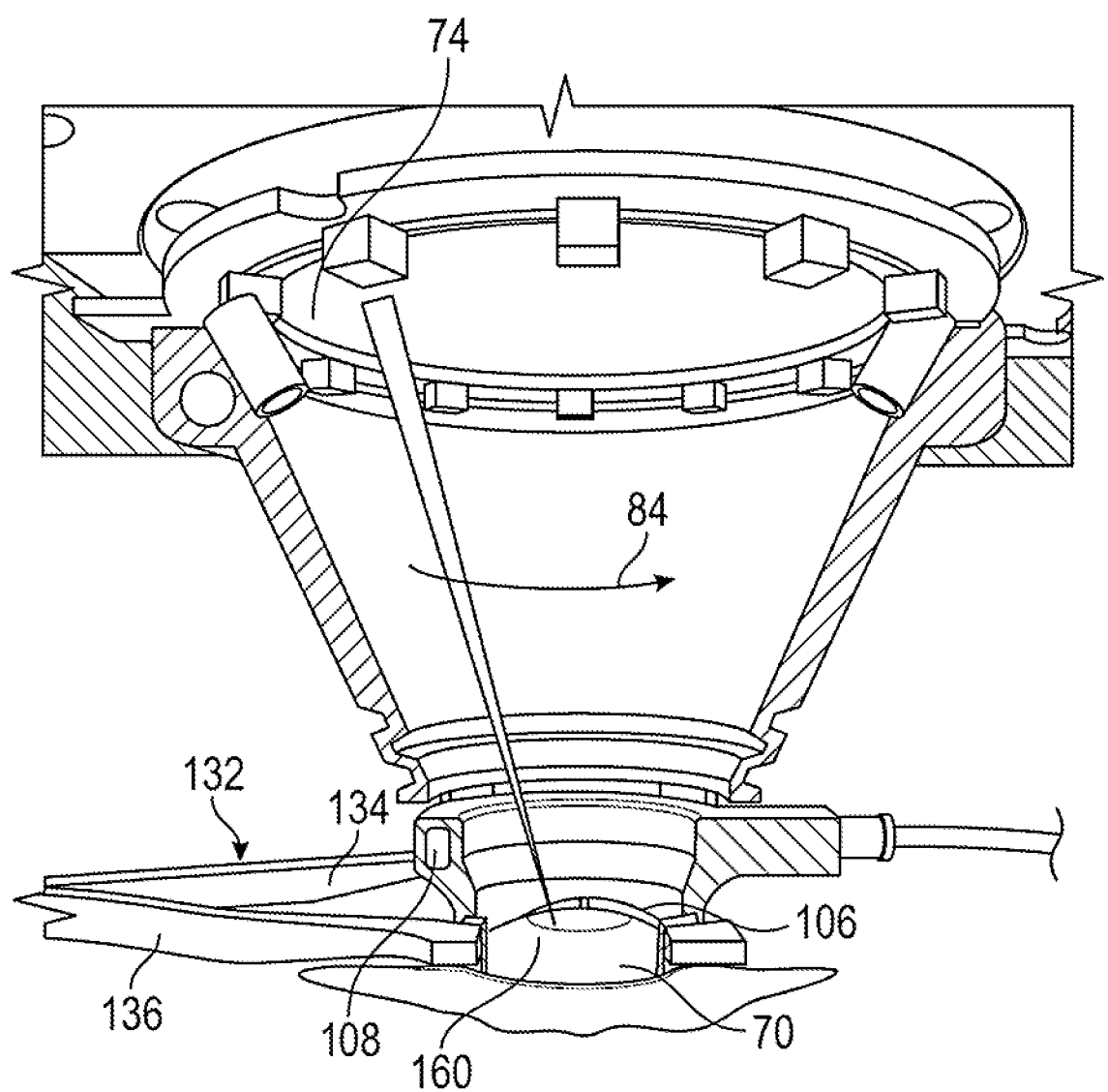
FIG. 8A is a cross-sectional view illustrating the patient interface docked to the eye of a recumbent subject with laser energy directed at the eye.
Figure 8B:
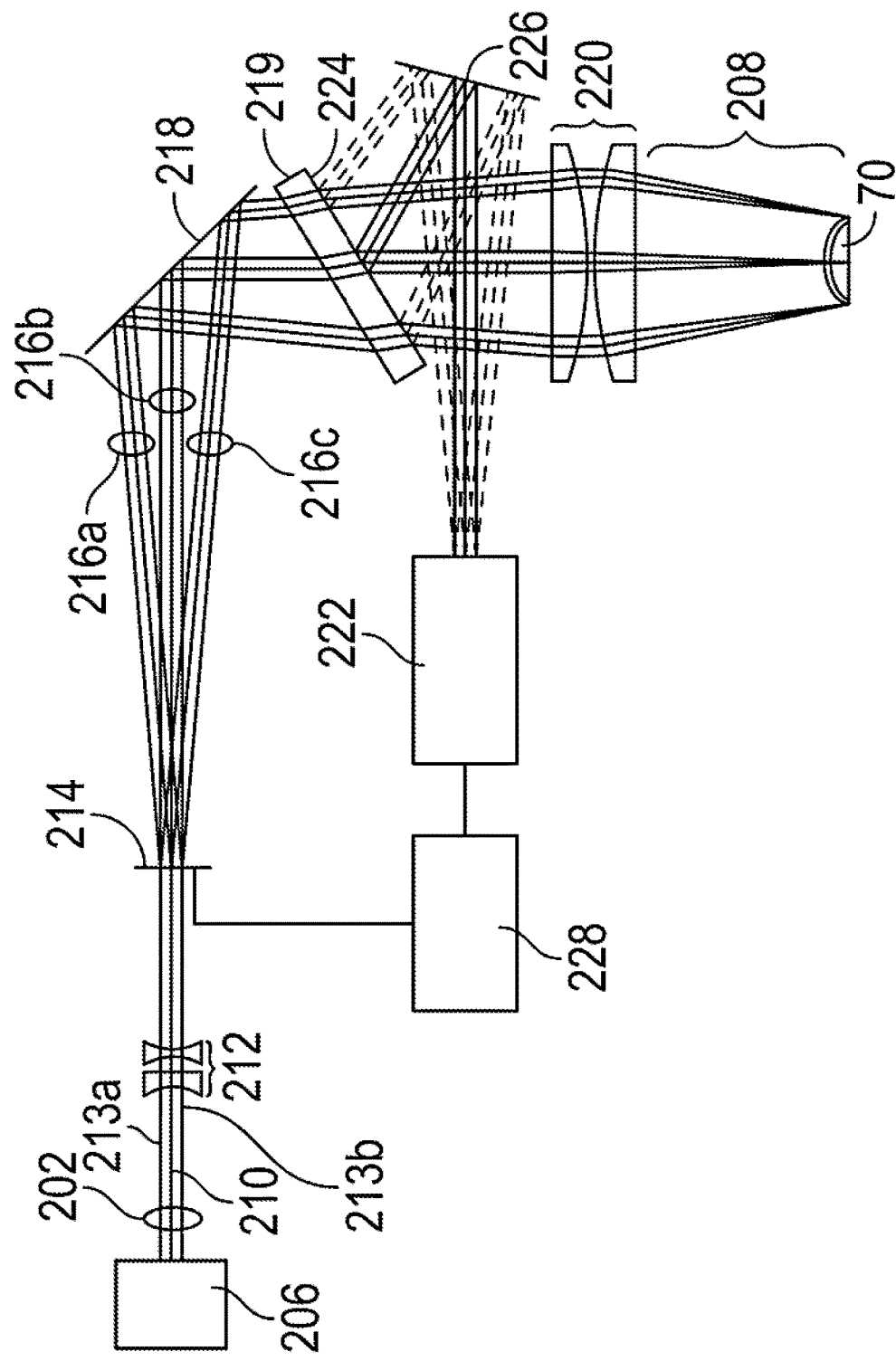
FIG. 8B is a schematic view of a 3-D scanner to image the front of an eye for treatment and/or positioning the patient interface.

Laser Treatment Optical System of FIG. 8B

FIG. 8B shows a representative optical system 200 that is configured to direct a laser beam to a targeted surface of eye 70 and rapidly move beam (as in FIG. 4M or 8A) in rotational or other cycles around the optical axis OA of eye. For example, the optical system may be a digital Galvano scanner system, such as one from Canon in which an LED optical encoder (digital position sensor) and high-speed digital servo controller scans a laser beam across the eye with high precision and accuracy. The movement of the scanned beam may, for example, be in a clockwise or counterclockwise movement inside interface 100.

Optical system 200 of FIG. 8B produces an optical beam 202 from an optical beam source 206. Optical beam source 206 includes one or more laser sources, such as one or more semiconductor diode lasers, fiber lasers, solid state lasers, frequency changing nonlinear optical materials (e.g., frequency doubling), etc. In representative examples, optical beam 202 has a predetermined wavelength (corresponding to one or more specific wavelengths and/or wavelength ranges) that is selected to be in the infrared region of the optical spectrum of about wavelength of 800-2200 nm or 1000-2200 nm, such as 1000 to 1700 nm or 875 nm to about 2100 nm, for example 1000 to 2100 nm. In general, the predetermined wavelength of optical beam 202 is selected to produce the trans-scleral therapeutic hyperthermia already described. For example, the predetermined wavelength may be selected to be sufficiently long that the optical beam 202 is absorbed by water in the scleral cells of eye 104, to a greater extent than would occur with shorter wavelengths such as 808 nm, 650 nm, 532 nm, 355 nm. In an example, optical beam 202 has a wavelength at 1475 nm and is generated in optical beam source 206 with a 1475 nm diode laser. The increased absorption at the longer predetermined wavelengths can allow the optical beam 202 to be directed to the eye target 70 through an offset 208 (e.g., free space) between a focusing lens 220 of the optical system 200 and target eye 70. The distance of offset 208 is, for example, at least 45 mm, for example 45 to 55 mm. In a disclosed example the offset is 35-45 mm, such as 40 mm.

In representative examples, optical beam 202 is emitted from optical beam source 206 as a collimated beam propagating along an optical axis 210. A lens group 212 is configured to adjust beam characteristics, such as beam area, divergence, convergence, etc. For example, a beam width, shown generally in relation to side rays 213a, 213b can be adjusted with lens group 212. Optical beam 202 is received by an optical scanner 214 that is configured to vary the direction of optical beam 202 and can, for example, move the beam in a rotary movement within interface 100. For purposes of illustration, optical scanner 214 is shown deflecting optical beam 202 along three optical beam paths 216a, 216b, 216c. Reflective element 218 is situated to redirect beam paths 216a-216c of optical beam 202. A beam splitting element 219 is situated to receive optical beam 202 and pass optical beam 202 to a focusing lens 220, which can include one or more lens elements. A camera 222 is also coupled to the optical system 200 by the beam splitting element 219. A surface 224 of the beam splitting element 219 can include a wavelength-selective coating that is configured to receive illumination from the eye target 70 through the focusing lens 220 and to direct the illumination to a reflective element 226 that directs the illumination to the camera 220 to image eye target 70.

Optical scanner 214 can be of various types that are suitable to scan an optical beam relative to eye target 70, including XY galvo scanners, 3D scanners, electro-optic scanners, or acousto-optic scanners. A controller 228 can be coupled to the optical beam source 206, optical scanner 214, and/or camera 222 to coordinate and control emission of optical beam 202 from optical beam source 206, scanning of the optical beam 202 with the optical scanner 214, and alignment of the optical scanner 214 relative to the eye target 70 or other process monitoring of the eye target 104. Controller 228 typically includes a processor and memory that can store scan files, laser parameters, and software for aligning and/or laser processing eye targets. The controller 228 can be of various types, including one or more computing devices, computing units, PLCs, PALs, ASICs, etc. The memory can include volatile memory, such as registers, cache, and RAM, as well as non-volatile memory, or a combination. The memory is accessible by the processor (or processors) of the controller and can store the software in the form of computer-executable instructions that can be executed by the processor. In some examples, the controller 228 can be distributed between different components (such as between the optical beam source 206 and the optical scanner 214), and in some examples communication is not required between all components.

In representative examples, optical beam 202 is a continuous-wave beam that is focused or defocused to a selected spot size at a predetermined position that is radially spaced outward from a corneolimbal or corneoscleral junction of eye 70. For example, optical beam 202 is directed along the optical beam paths 216a, 216c to positions at eye target 70 that are radially spaced outward from the corneolimbal or corneoscleral junction, and the optical beam path 216b at eye target 70 can also understood to be radially spaced outward from the corneolimbal junction if the position is sufficiently below or above the plane of the figure. In representative examples, the controller 228 controls the optical scanner 214 to scan the optical beam 202 in a cyclical annular pattern radially spaced outward from the cornealscleral junction. The scanning of the optical beam 202 produces a selected duty cycle of heating at sequential azimuthal positions of the annular pattern at the eye target 70 so that thermal relaxation can occur between scan cycles.

Unexpected lens slippage and/or eye movement may be detected by the camera software. The camera display at Z-focus provides added assurance of alignment.

Control Box and Positioning Arm

Figure 9A:
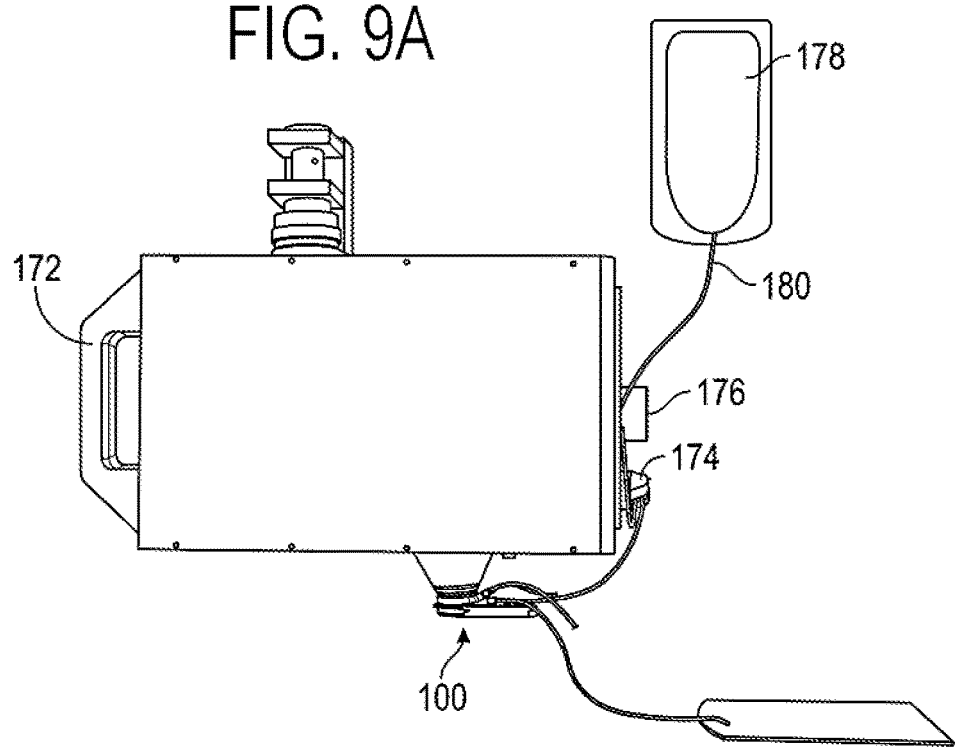
FIG. 9A is a side view of a control box for the patient interface, and a source of cooling liquid. The patient interface includes a laser cone that projects from the bottom face of the control box and is connected to a lens holder and speculum. Tubing connects the source of cooling liquid with the interface to cool the lens.

As illustrated in FIG. 9A, interface 100 may be suspended from and positioned by control box 118 that includes a handle 172 on a side face of the box for manually moving or positioning the unit, a tubing clamp 174 for suspending tubing without inducing torque on interface 100, and a peristaltic pump 176 (such as a Welco Ultra pump) for controlled movement of cooling liquid from a source 178 of cooled liquid, such as sterile saline or water, for example phosphate buffered saline (PBS). The illustrated pump 176 may move the cooling fluid at up to 100 ml/min, but generally the peristalic flow rates are controlled to about 50 ml/min to cool the contact lens 106 in holder 104 as the cooled liquid moves from source 178 through tubing 180 and pump 176. Contact lens fogging can be minimized with the coolant liquid temperature set to about −10° C. The lens heat capacity requirement is determined by thermal profiling of the material of the lens, such as a PMMA or BK7 lens.

Figure 9B:
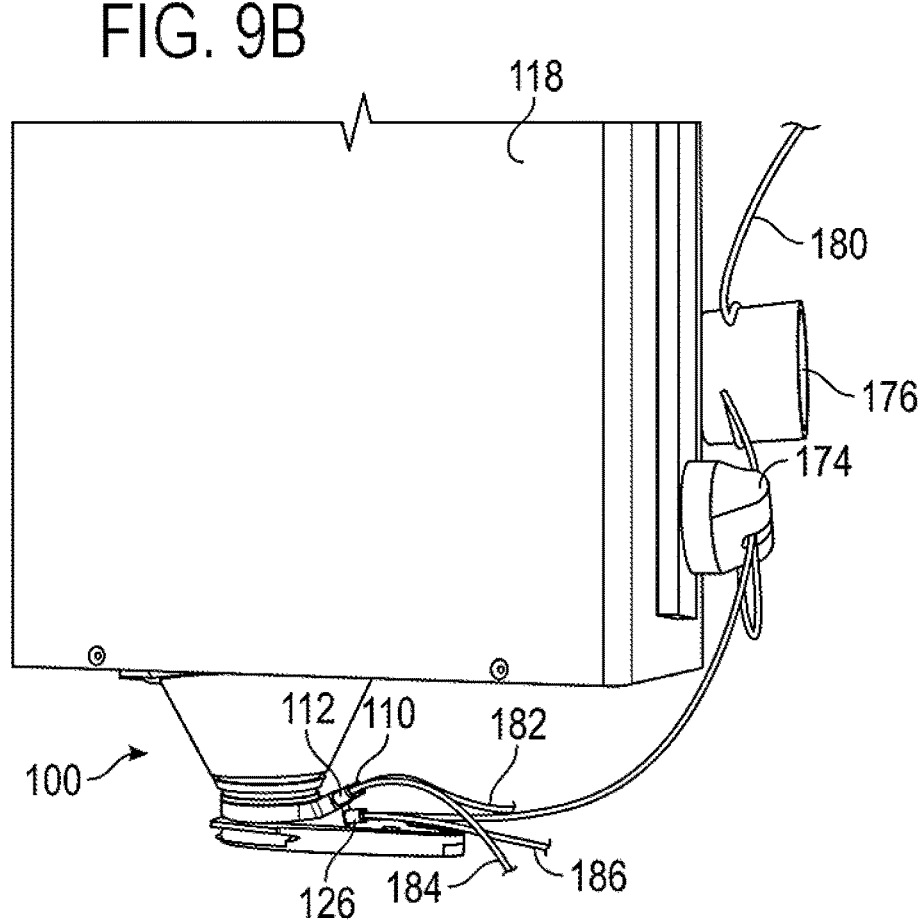
FIG. 9B is a perspective view of the control box of FIG. 9A, illustrating tubing clamps that reduce tip/tilt stress on the contact lens holder, and more clearly illustrating inlet and outlet tubing for the cooling liquid, and suction control tubing that communicates with the suction chamber.

As illustrated more clearly in FIG. 9B, pump 176 moves cooled liquid from control box 118 to interface 100 through an inlet line 182 that communicates with inlet port 110 to move the cooled liquid through channels 108 in lens holder 104 to cool lens 106 in situ. The liquid then passes through outlet port 112 and outlet line 184. A suction line 186 communicates with suction port 126 for drawing suction below lens 106 to improve contact between resilient sealing ring 120 and the surface of the eye during the laser implemented procedure.

Control box 118 may include a laser support structure (not shown), such as that disclosed in US 2018/0177632. The laser support structure may include one or more channels accommodating one or more optical fibers or light source cables. An optics tray may support one or more optical components that direct one or more lasers to a surface of eye 70, as described for example with respect to FIG. 8B. One or more optical components may also be contained within interface 100 to illuminate the eye.

Figure 9C:
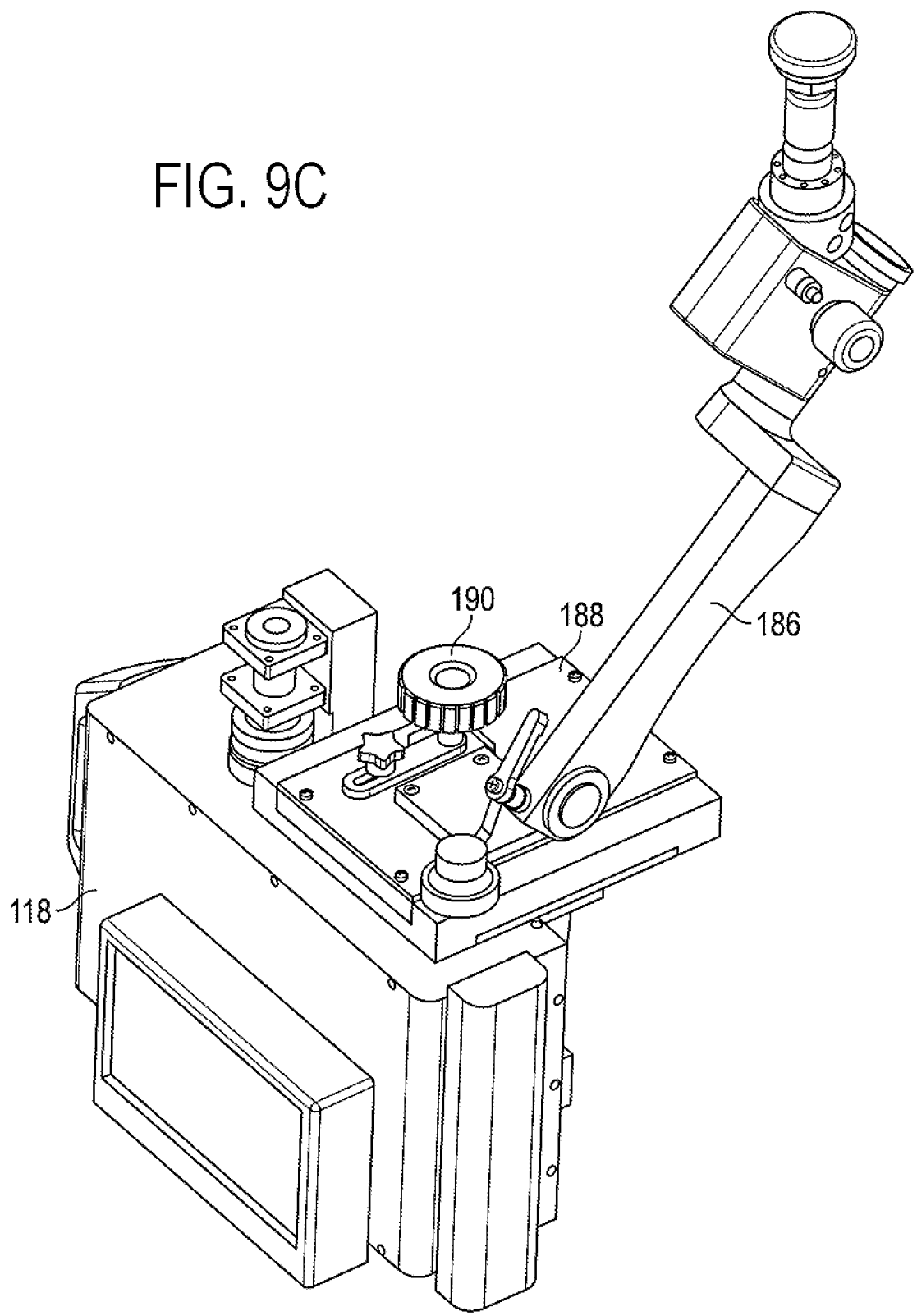
FIG. 9C is a perspective view of a control arm for positioning and docking the patient interface with the eye of the subject.

Control box 118 may be suspended from a positioning arm, such as an X-Y-Z positioning arm 186 (FIG. 9C) that may be computer-controlled for precise placement of the control box 118 and interface 100. Arm 186 is secured to box 118 by a flange 188 that has positioning knobs 190 that can be loosened to move flange 188 in a horizontal plane.

Patterned Energy Delivery System and Processor

For any of the desired treatment patterns, a processor may be coupled to the laser energy source and the scanner and configured with instructions to heat tissue at the plurality of treatment locations, providing an automated or computer-implemented treatment method that more precisely delivers energy to the preselected treatment locations. The plurality of treatment locations, for example a first annular treatment pattern and a second annular treatment pattern, may avoid underlying anatomic structures such as the insertions of intraocular muscles. In some embodiments computer implementation of automated treatment patterns can achieve controlled heating of specific locations to achieve the desired treatment outcomes.

Figure 10A:
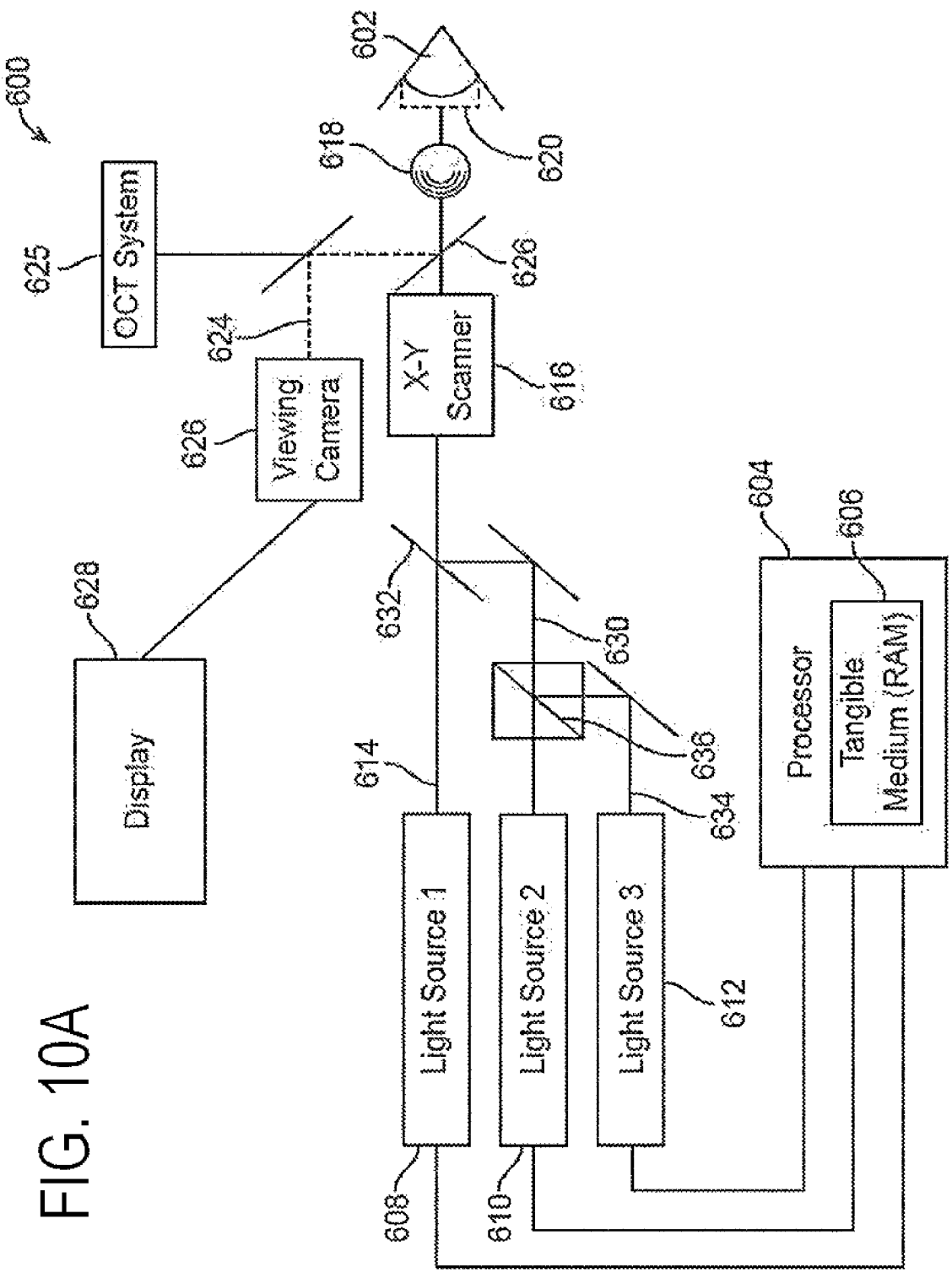
FIGS. 10A and 10B are schematic diagrams of an automated computer-controlled system for the treatment method.

FIG. 10A illustrates a system 600 for patterned delivery to an eye 602, in accordance with embodiments. The system 600 includes a processor 604 having a tangible medium 606 (e.g., a RAM). The processor 604 is operatively coupled to a first light source 608, an optional second light source 610, and an optional third light source 612. The first light source 608 emits a first beam of light 614 that is scanned by X-Y scanner 616 through an optional mask 618 and optional heat sink 620 onto the eye 602. The mirror 622 directs light energy from the eye 602 to a viewing camera 627 coupled to a display 628. An independent non-treatment light source for the optional viewing camera can be provided, for example. The mirror 622 may direct a portion of the light beam returning from eye 602 to the camera 627, for example. The second light source 610 emits a second beam of light 630 that is combined by a first beam combiner 632 with the first beam of light 614 prior to passing through X-Y scanner 616. The third light source 612 emits a third beam of light 634 that is combined by a second beam combiner 636 with the second beam of light 630 prior to passing through the first beam combiner 632.

The processor may be configured with one or more instructions to perform any of the methods and/or any one of the steps and sub-steps of the methods or treatments described herein. The processor may comprise memory having instructions to perform the method, and the processor may comprise a processor system configured to perform the method for example. In many embodiments, the processor comprises array logic such as programmable array logic ("PAL") configured to perform one or more steps of any of the methods or treatments described herein, for example. The processor may comprise one or more instructions of a treatment program embodied on a tangible medium such as a computer memory or a gate array to execute one or more steps of a treatment method as disclosed herein. The processor may comprise instructions to treat a patient in accordance with embodiments described herein.

The processor may be configured with instructions to determine one or more locations of the limbus, and/or one or more locations of the corneolimbal junction. In response to the determined location of limbus, for example, one or more locations of the corneolimbal junction may be determined. The processor may be configured with instructions to determine a treatment pattern based on the one or more locations of the limbus and/or the one or more locations of the corneolimbal junction. The treatment pattern may for example comprise a treatment pattern that is spaced one or more of 1.5 mm, 2.5 mm and 3.5 mm from the corneolimbal junction. The processor may be configured to deliver non-coagulative energy to the treatment locations on the treatment pattern to induce the thermal effects described herein.

The optical delivery system may comprise one or more of the first light source, second light source, third light source, X-Y scanner, optional mask, or a heat sink. The energy is directed by the automated optical energy delivery system to achieve repeatable heating of the same locations during repetitive cycles of heating. In some embodiments, the beams of light 614, 630, and 634 can be scanned onto the eye 602 at a specified X and Y position by the X-Y scanner 616 to treat the eye 602. An optional mask 618 can be used to mask the light applied to the eye 602, for example, to protect masked portions of the eye 602 while treating other portions as described herein. An optional heat sink 620 can be placed on the eye 602 during treatment to avoid heating specified portions of the eye 602, as described herein.

The system 600 can be used to apply light energy to the eye 602 in accordance with any suitable treatment procedure, such as the embodiments described herein. In many embodiments, the first light beam 614 has a first wavelength, the second light beam 630 has a second wavelength, and the third light beam 634 has a third wavelength. Each wavelength can be the same or a different wavelength of light. The processor can be coupled to each of the light sources to selectively irradiate the eye with light having wavelengths within a desired range of wavelengths. The software may comprise instructions of a treatment table so as to scan the laser beam to desired treatment locations as described herein, for example.

The laser system 600 may comprise an OCT system 625, such as a commercially available OCT system. The OCT system may for example be a CASIA2 or CASIA SS-100 OCT scanner (TOMEY). The OCT system may for example be a commercially available OCT system such as one sold by Tomey, Heidelberg, Visante, or Optovue. The OCT system can be coupled to the viewing optics and laser delivery system with a beam splitter 626. The viewing optics may for example comprise an operating microscope (such as one sold by Zeiss, Haag Streit, Leica, or Moller Weidel), a slit lamp, or other custom optics. The OCT system can be used to measure the eye in situ during treatment. For example, the OCT system can be used to generate OCT images as described herein in order to generate tomography of the eye to determine the location of target tissues, movement of target tissues, and stretching of target tissues as described herein. The OCT system 625 can be coupled to processor 604 and used to control the laser system with a feedback loop, for example. Ophthalmoscopes or other suitable eye imaging devices can be used to generate images of the exterior and/or interior of the eye, and can include imaging detectors such as CCD or CMOS detectors.

The processor can be configured with instructions to scan the laser beam on the eye in accordance with the treatment patterns and parameters as described herein.

Figure 10B:
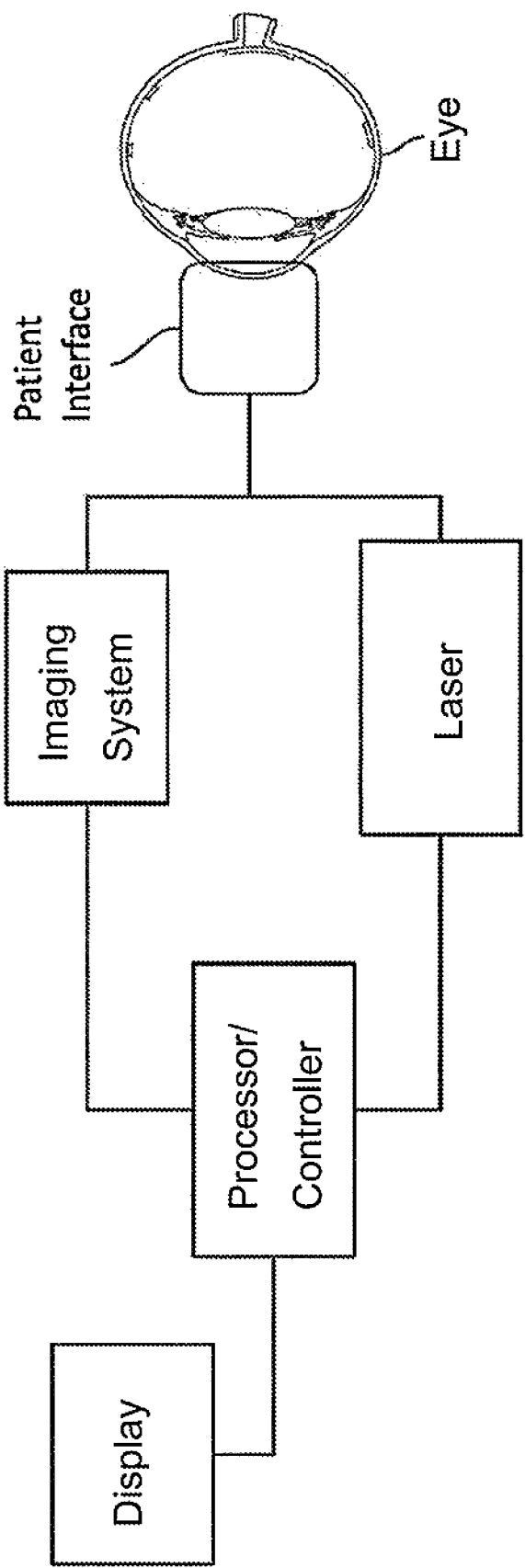

FIG. 10B shows another embodiment of a treatment system which may be used for any of the treatment methods described herein. The system may comprise a laser scanner (such as that shown in FIG. 8B) which directs and scans laser energy from a continuous wave or pulsed laser to one or more locations on or inside the eye. The scanner may be coupled to a patient interface or patient coupling structure as described herein. The scanner may further be coupled to an imaging system, for example a camera, OCT, UBM, ophthalmoscope, etc., as described herein. The imaging system may be used to capture one or more images of the eye before, during, or after treatment as described herein.

A processor or controller may be coupled to the energy source (such as the laser) and the imaging system and be configured with instructions to scan the energy beam to a plurality of locations or in one or more patterns and image the tissue during treatment. The system may also comprise a display coupled to the processor that allows the user to visualize the tissue prior to, before, or after treatment. The display may show images that allow the user to see the tissue treated and plan the treatment. Images shown on the display may be provided in real-time and can be used prior to treatment to allow the user to align the tissue and/or select a treatment zone or pattern to target. Identified target treatment zones may be input by the user to program the treatment depth, location, and pattern in response to the images shown on the display. The imaging system can be used to visualize movement of ocular structures during treatment in order to detect beneficial treatment effects.

The glaucoma treatment systems described herein may simultaneously provide imaging guidance, quantitative characterization of the tissue (for example measuring mechanical properties such as elasticity or the presence of tissue coagulation), and/or perform therapeutic tasks.

In some embodiments, the treatment system described herein may comprise two or more lasers. The processor may be configured with instructions to treat the eye with a first wavelength of light at a first location (or plurality of locations) and a second wavelength of light at a second location (or plurality of locations). The treatment system described herein may comprise one or more lasers within a range of about 1.0 μm to about 2.2 μm, about 1.4 μm to about 1.5 μm, for example about 1.47 μm.

Figure 11:
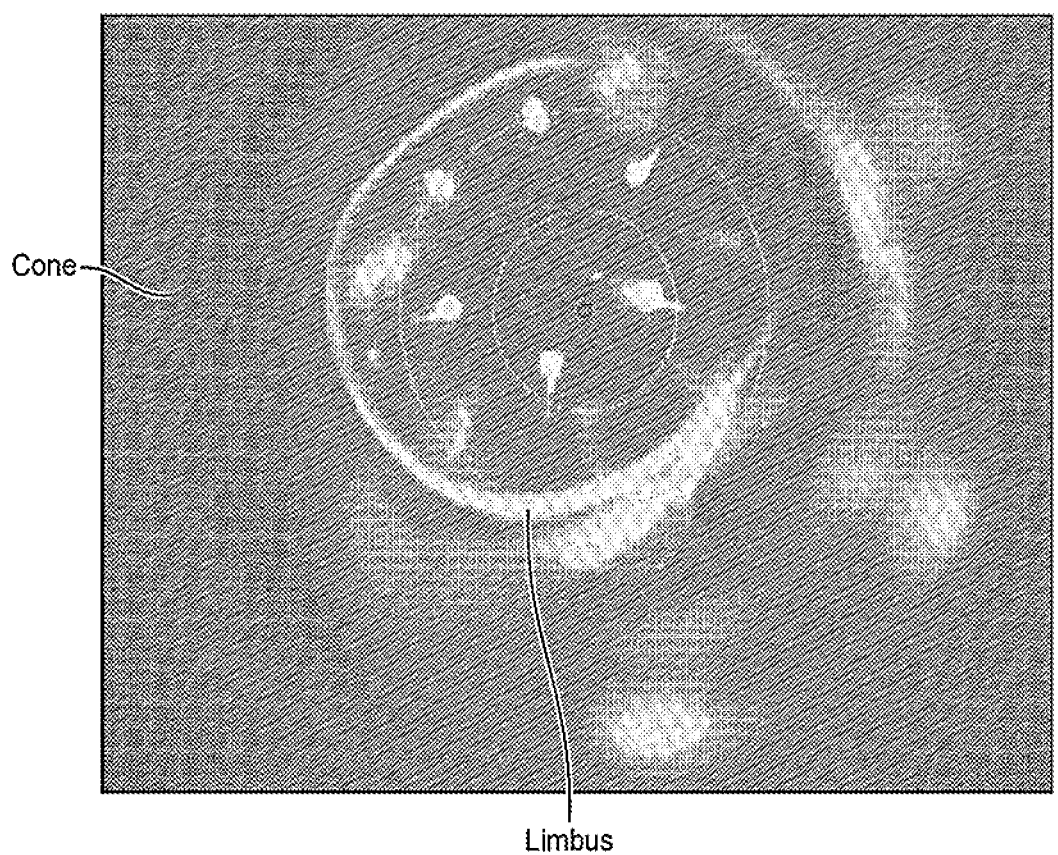
FIG. 11 shows an image of an eye taken by a camera after docking the patient interface and system to the eye, in accordance with embodiments, with an image of the limbus illustrated on the eye. The limbus location helps identify the corneoscleral or corneolimbal junction. The anterior border of the limbus is the corneolimbal junction.

FIG. 11 shows an image of an ex vivo porcine eye taken with a camera after docking the patient interface and system to the eye. The limbus was clearly visible for use to pattern glaucoma treatment relative to the location of the limbus or corneolimbal junction. Patterning may be selected manually by the user (e.g. medical professional) or the patterns may be determined automatically (or semi-automatically) by the system based on an estimated location of the limbus, or other fiducial of interest. The location of the limbus may be estimated manually by the user or determined automatically through imaging and feature detection. The location of the limbus may for example be "tracked" automatically by the system using a camera and/or other imaging system such as OCT as described herein. The location of the limbus may comprise a complete, annular outline of the limbus or may comprise multiple locations along the limbus which may be used as reference points for determining the shape of the limbus and/or where treatment should occur (i.e. an incomplete outline of the limbus).

Figure 12A:
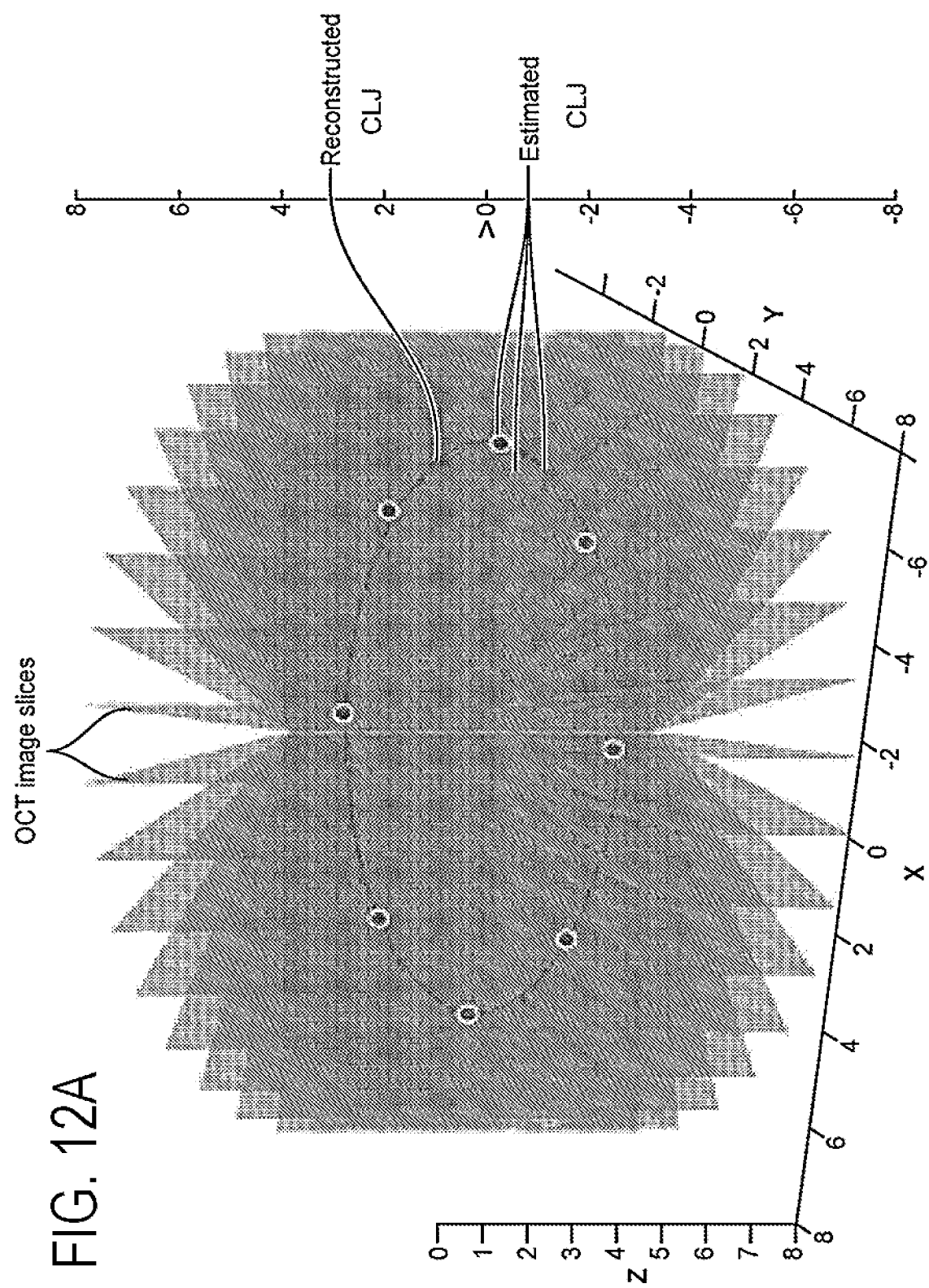
FIG. 12A shows an imaging scheme which may be used to estimate the shape of the limbus and the corneoscleral or corneolimbal junction.

Identification of one or more locations of the limbus as described herein may be used to estimate one or more treatment locations. The anterior border of the limbus may be used as a surrogate for the corneolimbal junction 32. Alternatively, or in combination, one or more locations of the corneolimbal junction 32 may be estimated from one or more OCT slices. For example, a single OCT image taken through the center of the eye may be used to identify two locations of the corneolimbal junction (one on either side of the eye) and the treatment locations/pattern may be determined in response to the two corneolimbal junction locations identified. In some instances, multiple OCT images may be taken at different angles relative to the center of the eye and a plurality of the corneolimbal junction locations may be identified and used to estimate the shape of the corneolimbal junction. FIG. 12A shows one such imaging scheme which may be used to estimate the shape of the corneolimbal junction. Multiple OCT images may be taken across the center of the eye at varying angles and the one or more location of the corneolimbal junction may be estimated from each image. The locations (and optionally the images as shown) may then be used to estimate the shape of the corneolimbal junction using partial 3-D reconstruction.

Figure 12B:
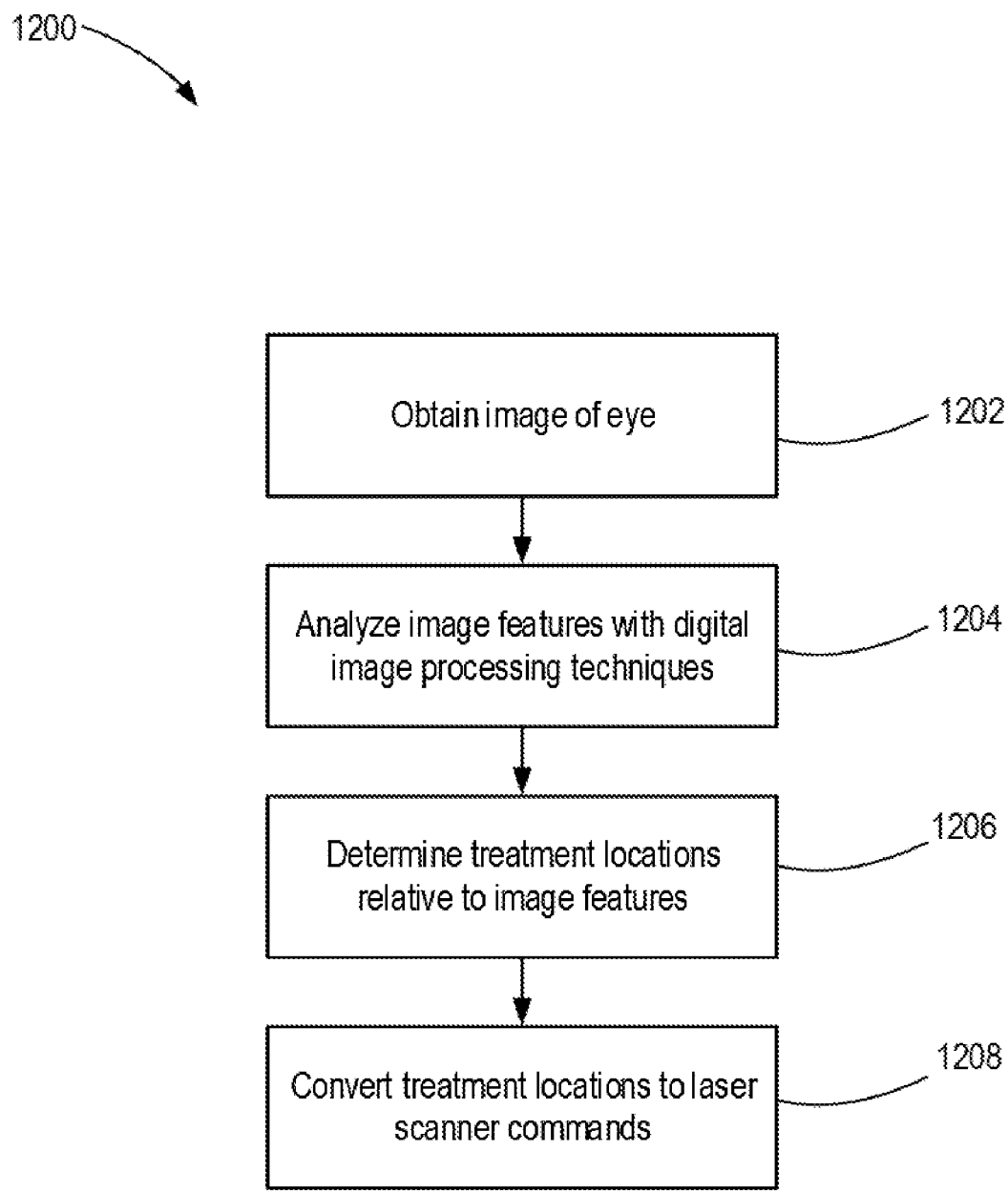
FIG. 12B is a flowchart of an example method of imaging and determination of treatment locations.

In some instances, the location and/or shape of the corneolimbal junction may be estimated in response to a plurality of limbus locations of the eye. As an example, an image (e.g. an anterior image of the eye) including the limbus may be acquired (e.g. as shown in FIG. 11). The locations of the limbus, or plurality of limbus locations may be determined, based on the image of the eye. For example, by detecting changes in intensity in the anterior image (e.g. across the image, over a series of images, etc), the location of a plurality of limbus locations may be determined. In some instances, one or more processors may be utilized to analyze the image to determine the limbus locations. Based on the plurality of limbus locations, a plurality of the corneolimbal junction locations may be estimated substantially as described throughout. Suitable techniques for automated image analysis include automated digital image processing techniques, including machine learning, object identification algorithms, pattern recognition algorithms, video tracking algorithms, convolutional neural networks, etc. FIG. 12B shows an example of an automated process 1200 for determining treatment locations. At 1202, an image of the eye is obtained with a suitable imaging device, and at 1204, image features in the image are analyzed with digital image processing techniques, such as through any of the digital image processing techniques described herein. At 1206, suitable treatment locations are determined relative to the features in the image. For example, where anatomical features are found, such as a corneolimbal junction in trans-scleral treatment examples or fundus features like the macula or optic disk in trans-pupillary examples, suitable treatment locations can be determined relative to and based on the found features. At 1208, the treatment locations can be converted to suitable laser scanner commands for an aligned and calibrated laser scanner and a scanner command table that maps scanner command values to one or more scanning planes, surfaces, or volumes.

Figure 13A:
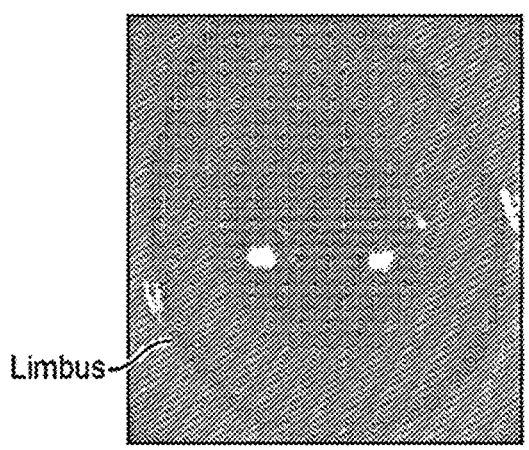
FIGS. 13A-13D show an exemplary process for generating a treatment pattern based on one or more locations of the limbus and corneoscleral junction.
Figure 13B:
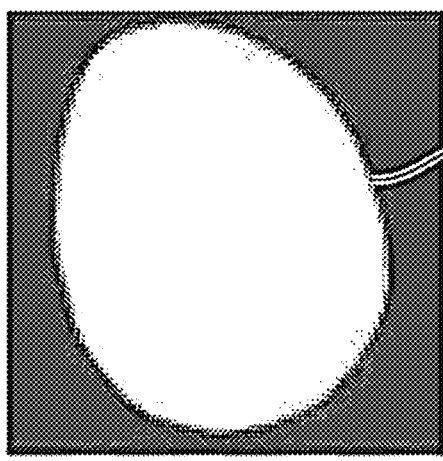
Figure 13C:
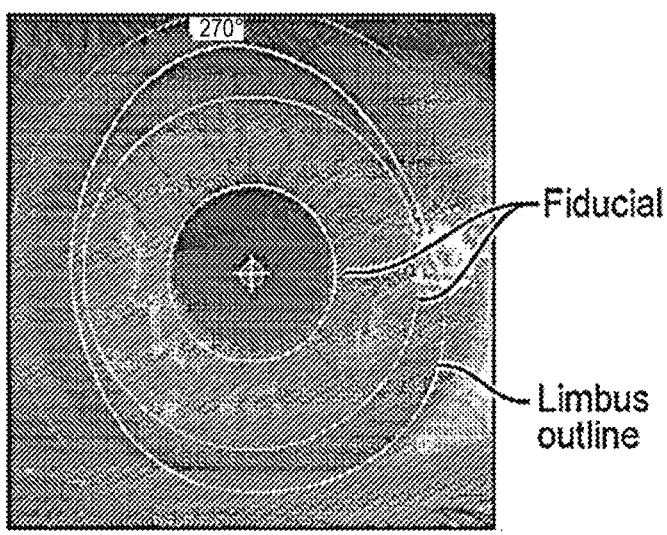
Figure 13D:
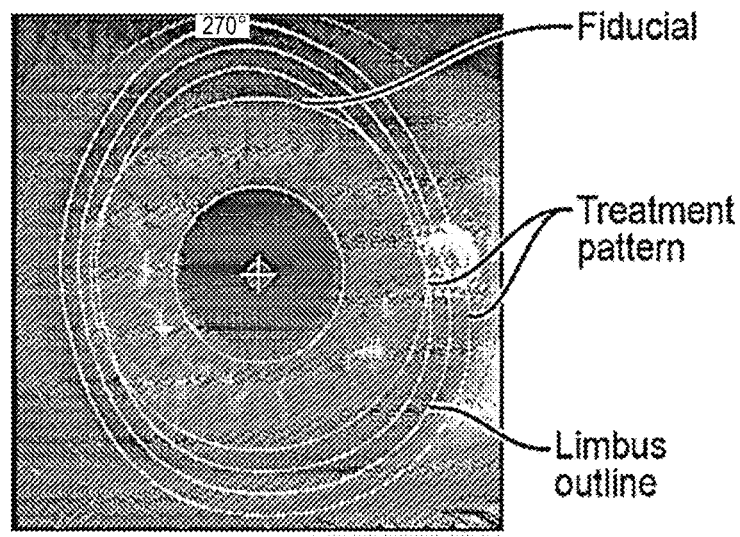

FIGS. 13A-13D show an example of a process for generating a treatment pattern based on one or more locations of the limbus. FIG. 13A shows an anterior image of an eye taken with a front camera of a CASIA2 OCT system. The anterior image of the eye may be transferred to the processor for detection of the limbus edge. FIG. 13B shows the image after processing to determine the boundaries (edges) of the limbus. The portion of the eye within the limbus has been colored white while the portion of the eye outside the limbus has been colored black. This black and white image may then be used to generate X-Y coordinates of the edge of the limbus. The processor may then use the X-Y coordinates to generate an outline of the limbus which may be overlaid onto a real-time image of the eye shown on the display as shown in FIG. 13C. The X-Y coordinates may be registered with the real-time image of the eye such that the limbus shown on the display and the X-Y coordinate generated limbus outline are co-aligned. Treatment patterns can also be automatically generated based on the outline. Where arcs are formed, treatment patterns can be generated using the orientation of the patient so as to align the arcs relative to superior/inferior directions or selected azimuths. In some examples, posterior trans-pupillary images can be taken using the CASIA2 OCT system or another camera, and anatomical feature boundaries determined so that laser scanning coordinates may be generated relative to the anatomical feature boundaries.

The image may also display fiducials with reference to the center of the eye to aid in centration of treatment, for example circles displayed radially outward every 5 mm from the center of the eye. The processor may further use the X-Y coordinates and/or the generated outline of the limbus to determine a treatment pattern, for example a series of limbus-guided treatment locations. It will be understood by one of ordinary skill in the art that during use the limbus outline and/or treatment patterns may be registered to one another (i.e. co-aligned) such that the outline and real-time location of the limbus overlap or are offset by a pre-selected amount to space the limbus-guided treatment pattern a desired distance from the corneolimbal junction.

Figure 14:
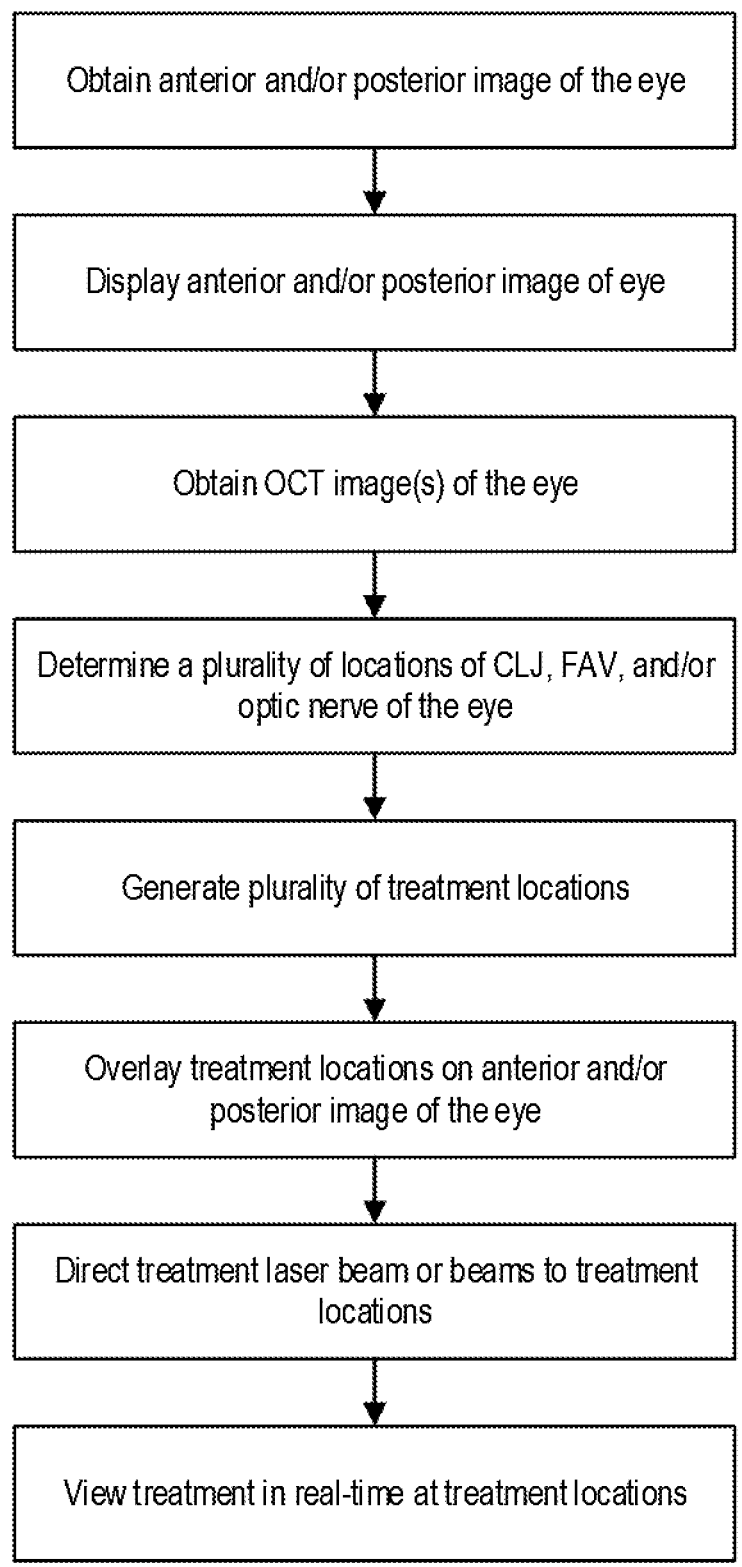
FIG. 14 is a flowchart of a method for determining a target treatment location, in accordance with embodiments.

FIG. 14 shows a method for determining a target treatment location. The method may use one or more of the systems described herein. In a first step, an anterior image of the eye may be obtained by a camera or video recorder. In some examples, a posterior image may be taken. In a second step, the image of the eye may be displayed to a user as described herein, though in some examples image display for a user or user-intervention based on the obtained image is not needed. In a third step, one or more images of the eye, such as video or OCT images, may optionally be obtained. In a fourth step, a plurality of locations of the corneolimbal junction (or the limbus or other fiducial described herein) may be determined from the anterior image of the eye, the one or more OCT images of the eye, or any combination thereof. In some examples, a plurality of locations of macular features, such as a foveal avascular zone, optic nerve, etc., are determined from a posterior image, OCT image, or combination. The plurality of locations of the corneolimbal junction or macula may be estimated manually by the user or automatically by the processor. The plurality of the corneolimbal junction locations may optionally be registered with a corresponding plurality of anterior or posterior image locations. In a fifth step, a plurality of treatment locations for the eye may be determined in response to the plurality of locations of the corneolimbal junction or macular features. The plurality of treatment locations may be determined manually by the user or automatically by the processor. In a sixth step, the treatment locations may be overlaid onto the anterior image shown on the display, though such display may be omitted in automated or streamlined processing. The treatment locations may optionally be adjusted or approved by the user. In a seventh step, treatment energy may be directed to the treatment locations displayed on the image by a laser source and scanner as described herein. Typically, the laser source includes a plurality of lasers operating at different wavelengths or suitable for operating in selected modes (such as pulsed, continuous-wave, or with selected pulsed characteristics, such as repetition rate, pulse duration, power, pulse energy, etc.). In an eighth step, the treatment may be viewed and/or automatically monitored in real-time at the treatment locations to adjust or halt treatment if movement of the eye occurs.

A processor may be provided that is configured with instructions for performing the series of steps illustrated in FIG. 14. In some instances, the processor may provide instructions to obtain an anterior and/or posterior image of the eye. For example, the image of the eye may be obtained with a camera with aid of the processor. In some instances, the processor may be configured with instructions for receiving an image of the eye.

The processor may provide instructions to display one or more of the images of the eye. In some instances, the processor may provide instructions to obtain OCT image(s) of the eye. In some instances, the processor may provide instructions to determine a plurality of locations of the corneolimbal junction of the eye. The processor may estimate in some instances the plurality of the corneolimbal junction canal locations in response to the anterior image of the eye and/or the plurality of retinal locations in response to the posterior image of the eye. Alternatively, or in addition, the processor may estimate the plurality of Schlemm's canal locations, retinal locations, or other ocular locations, in response to the plurality of OCT images of the eye.

In some instances, the processor may be configured with instructions to generate a plurality of treatment locations. Optionally, the processor may be configured with instructions to generate the plurality of treatment locations for the eye in response to the plurality of the corneolimbal junction locations.

In some instances, the processor may provide instructions to overlay treatment locations on the anterior and/or posterior images of the eye. The processor may be configured with instructions to overlay the plurality of treatment locations and the plurality of the corneolimbal junction locations on the anterior image of the eye. Optionally, the processor may be further configured to register the plurality of locations of the corneolimbal junction with a corresponding plurality of anterior image locations. Optionally, the processor may be further configured with instructions to overlay the plurality of treatment locations and the plurality of retinal locations on the posterior image of the eye, and the processor may be further configured to register the plurality of locations of the retina with a corresponding plurality of posterior image locations.

The processor may provide instructions to direct treatment energy to treatment locations on the display. In some instances, the processor may be configured with instructions to alternate treatment at a first plurality of treatment locations with treatment at a second plurality of treatment locations. Optionally, the processor may be configured with instructions to generate a treatment table that includes a plurality of coordinate reference locations corresponding to the plurality of treatment locations overlaid on the anterior and/or posterior images. Optionally, the energy source directed to the eye may comprise a pulsed laser source wherein each of the plurality of coordinate references corresponds to a pulse from a laser source. In some instances, the processor may provide instructions to display treatment in real-time at the treatment locations.

Although the steps described above show acquiring an image of an eye and treating the tissue at a treatment region selected by a user, one of ordinary skill in the art will recognize many variations based on the teachings described herein. The steps may be completed in a different order. Steps may be added or deleted. Some of the steps may comprise sub-steps. Many of the steps may be repeated as often as necessary to treat the tissue as desired. The steps can be applied with any suitable apparatus herein and are not limited to trans-scleral treatment examples.

Examples herein include apparatus and methods for performing selected trans-pupil retinal treatments and combined trans-scleral-trans-pupil treatments.

Figure 15:
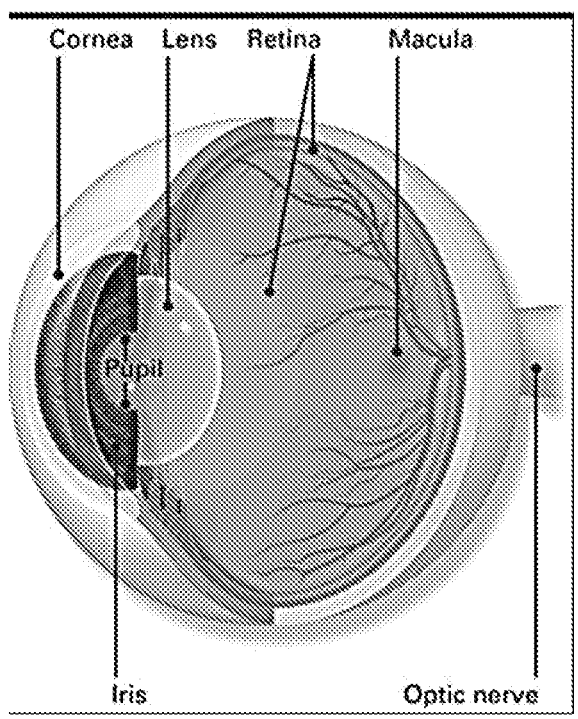
FIG. 15 is a perspective, and partially cross-sectional, schematic view of a human eye.
Figure 16:
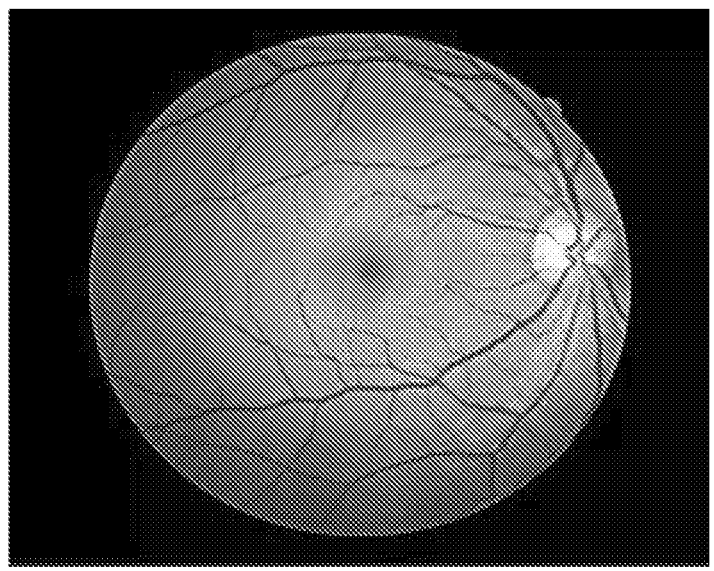
FIG. 16 is a photographic image of the fundus including the central retina showing the macula, the fovea avascular zone (FAZ), and the foveola at the center of the image.

FIG. 15 schematically shows an example of a human eye including the cornea, lens, iris, and pupil structures near the anterior surface of the eye, and the retina, macula, and optic nerve towards the posterior pole of the eye. FIG. 16 shows the central retina of FIG. 15 within the vascular arcades, including the darker macula portion near the center. In representative examples herein, the sclera of the eye (adjacent to the cornea) is targeted for irradiation with a 1475 nm trans-scleral laser beam with a selected set of trans-scleral laser and scan parameters for IOP lowering treatment, and/or the retina of the eye, for example macula, is targeted for irradiation with an 810 nm separate set of trans-pupil laser and scan parameters for panmacular neuroprotective therapy, thereby inducing sublethal and therapeutically advantageous biomodulation or biostimulation of eye tissue in one or both places, e.g., during a complete treatment window or instance. Therapeutic benefits can include reduced intraocular pressure (IOP), neuroprotection, and comprehensive management of glaucoma such as open-angle glaucoma.

Biomechanisms

In accordance with representative examples herein, the central retina of the eye can receive sublethal laser photostimulation, for the treatment chronic progressive neurogenerative vascular retinopathies and of other disorders, such as POAG, that share similar common characteristics. Sublethal non-damaging laser photostimulation of the central retina targets the retinal pigment epithelium (RPE) cells with subthreshold laser energy so as to trigger a stress response. With carefully selected laser parameters and/or scan patterns, the stress response can be configured to activate a cascade of molecular cellular biochemical activities that can rebalance pathological retinovascular neuro-trophic deficiencies preventing and possibly reversing progressive apoptotic processes (i.e. the loss of retinal ganglion cells in POAG). Thus, in representative examples, laser parameters are selected such that energy is delivered in patterns configured to produce biological effects in a photo-thermal-stimulation therapeutic window that is above an activation threshold but below a lethal threshold (e.g., between 44° C. and 50° C.). In general, various parameters (such as laser pulse energy, duration, fluence, irradiance, pattern, etc.) are selected to recruit and activate in a pathoselective manner a large amount, and preferably the highest possible number of, RPE cells for the biological photo-stimulation process. Such photo-thermal-stimulation can be configured so as not to harm or have an effect on normal healthy RPE cells but activates endogenous reparative and/or regenerative processes that selective affect and improve only dysfunctional RPE cells according to their specific dysfunction. A primary response to RPE sublethal photostimulation is understood to be the activation of heat shock proteins (HSPs) and of cytokine expression, which triggers a cascade of events leading to RPE cellular repair, replacement and regeneration. These events can result in improved transport function, normalized retinal autoregulation, reduced biomarkers of chronic inflammation, reparative acute inflammation, and immunomodulation. Such effects can provide neuroprotection, neuro-trophic enhancement, with restoration and/or regeneration of sick dysfunctional cells, reducing, delaying, or preventing vision loss, for example restoring visual functions in various chronic progressive degenerative retinal disorders and in POAG (which can share similarities).

The effects of subthreshold laser central retina sublethal photostimulation with no discernable retinal damage, can be entirely "homeo-trophic," normalizing retinal function, reducing disease progression and the risk of visual loss. The normalization of retinal cytokine expression can be neuro-protective in POAG in the same way that it is retinal protective in diverse chronic progressive retinopathies that are pathogenically disparate, that exhibit very different drug response profiles (such as diabetic macular edema (DME) and central serous retinopathy (CSR)) and that respond in ways specific to, and characteristic of, the particular disease process. Sublethal RPE laser photostimulation can be a non-specific trigger of disease specific RPE HSP activation and cellular repair. Furthermore, because sublethal RPE laser photostimulation can only normalize the function of dysfunctional cells, it is also pathoselective, affecting abnormal cells while having negligible effect on the healthy ones, as has been clinically observed in the significantly greater improvements in eyes with the worst pre-treatment conditions.

Disease specific response can be further demonstrated by the characteristically different Pattern ElectroRetinoGraphy (PERG) responses in dry AMD compared to the PERG responses in inherited retinopathies after subthreshold laser central retina sublethal photostimulation treatment. In each case, there is a retinal abnormality. Thus, a therapeutic response to the non-specific trigger of sublethal laser photostimulation is observed. In each case, the retinal abnormality is different. Thus, the therapeutic response, while always homeotrophic, is different, and reflects the nature of the underlying retinal abnormality (the disease specific repair response). POAG may represent, at least in part, a primary optic neuropathy or a manifestation of central nervous system disease. Electrophysiologic tests such as PERG and visually evoked potential (VEP) testing can objectively measure and monitor electrophysiologic indices of functionality of the ganglion cells and of the optic nerve. Thus, by treating the retina, a unique disease-specific therapeutic response in glaucomatous optic nerves can be elicited. Thus, a not yet identified retinal abnormality underlying at least some cases of POAG may exist, which might help to explain the progressive optic atrophy observed despite IOP reduction, and in "normal" or "low" tension glaucoma. It may also be possible that retinogenic loss of neurotrophism is a separate and unique retinal disease entity that may underlie some, or all, cases of OAG, though further study is required.

Subthreshold panmacular micropulse laser photo-stimulation treatment has been disclosed by Luttrull et al., Chapter 20—Glaucoma research and Clinical Advances: 2018 to 2020: Samples J R and Klepper P A, Eds. Kugler Publications: Amsterdam, Neederlands (incorporated herein by reference), as a neuroprotective treatment for patients with primary open-angle glaucoma. Subthreshold panmacular micropulse laser can restore RPE cells transport and gene expression functions, improving retinal trophic deficiency and resulting in increased ganglion cells electrophysiologic functionality on pattern electroretinography (PERG) and in improved visual functions on automated perimetry. These improvements indicate that the sublethal laser photostimulation can rescue dysfunctional but still viable retinal elements, possibly through the upregulation of endogenous neuro-enhancing and neuro-protective neuro-trophic factors, promoting the long-term survival and enhancing the functionality of ganglion cells and other neurons. POAG shares most of the common characteristics found in any and all chronic progressive degenerative retinopathies (AMD, DR, CSC, RP, etc.) and POAG could similarly benefit from the same sublethal laser photostimulation of the RPE.

Theoretically, the primary mechanism of action of sublethal photostimulation of the RPE is a reparative acute inflammatory response prompting the activation of heat shock proteins (HSPs), which triggers a cellular cascade resulting in cytokine expression, upregulation of pigment epithelium derived factor (PEDF), intracellular repair, replacement, regeneration, improved RPE cell function, normalized retina homeotrophy autoregulation, suppression of apoptosis, reduction of chronic inflammation biomarkers, and restoring reparative immunomodulation responses, including the mobilization to the retina of bone marrow-derived hematopoietic stem cells able to differentiate in epithelial and/or endothelial cells. In-vivo studies have shown that improvements in retinal electrophysiologic indexes on PERG, in mesopic visual function on automated perimetry can be documented within 24 hours from the sublethal treatment. The absence of discernable iatrogenic damage makes the neuroprotective homeotropic sublethal laser photostimulation treatment a native renewable physiologic process with the potential of early POAG treatments, prophylactic treatments and of periodic retreatments to maintain the homeotropic effects, slow disease progression and reduce the risk of visual loss.

The use of laser trans-pupillary thermo therapy (TTT) to perform a sublethal hyperthermia photostimulation treatment to elicit retinal biochemical responses with the expression of endogenous neuroprotective heath shock proteins (HSPs) has also been proposed by Kim et al. (Neuroprotective effect of trans-pupillary thermotherapy in the optic nerve crush of the rat. *Eye* (2009); 23:727-733) and by Ma J et al. (Neuroprotective effect on retinal ganglion cells by trans-pupillary laser irradiation of the optic nerve head. *Neurosci. Lett.* (2010), doi:10.1016/j.neulet.2010.01.001). Heat shock proteins are a group of proteins that are upregulated by hyperthermia or other types of physiological and environmental stress. HSPs can enhance cell survival under conditions of further severe stress. Some of HSPs are constitutively expressed, whereas other HSPs are inducible in response to various kinds of stress. In the nervous system, HSP70 family, which consists of Hsc70 or constitutive form, and HSP72 or inducible form, can have a protective effect against ischemia, seizures, and axotomy. Also, retinal ganglion cells (RGCs) can be protected against intraocular pressure elevation or axotomy by induction of HSP72 by hyperthermia, zinc, as well as medications such as geranylgeranylacetone. RGC death is one of the major pathologic events in glaucoma, so protection of RGCs by induction of HSPs can be used to treat to glaucoma. However, some methods have shown increased HSPs expression with a neuroprotective effect, non-invasive and safe methods to induce HSPs without any systemic effects deserve further investigation.

TTT is a treatment modality in which hyperthermia is created with infrared irradiation energy directly delivered to the posterior segment of the eye by, e.g., an 810 nm diode laser. TTT can be performed with a broad beam and long exposure times. Mainster (Mainster M A, Reichel E., Trans-pupillary thermotherapy for age related macular degeneration: long-pulse photocoagulation, apoptosis, and heat shock proteins. *Ophthalmic Surg Lasers* 2000; 31: 359-373) showed TTT increased temperature in treated tissue up to 10° C. above baseline levels. Using this hyperthermia, TTT has been tried for the treatment of various intraocular tumors (i.e., choroidal melanoma, hemangioma, and retinoblastoma) and choroidal neovascularization in age-related macular degeneration. TTT increases the temperature in the treated tissue, and therefore TTT may stimulate the expression of HSPs. TTT performed on the optic nerve head, which is a primary site of glaucomatous optic nerve damage, induced expression of HSP72 effectively in the treated tissue. Optimal parameters of TTT for maximal HSP72 expression in the optic nerve head with no damage to the ocular tissues were determined by Kim et al. (Kim J M, Park K H, Kim Y J, Park H J, Kim D M. Thermal injury induces heat shock protein in the optic nerve head in vivo. Invest Ophthalmol Vis Sci 2006; 47:4880-4894) to be 100 mW for 60 s. In this setting, no tissue damage was detected with confocal scanning laser ophthalmoscope, light microscope, and scanning electron microscope as well as fundoscopic examination. In a next step, TTT was applied to an optic nerve crush injury model of the rat to investigate neuroprotective effect and it was found that the use of TTT increased the survival of RGCs in retinal areas close to the optic nerve head in the optic nerve crush injury model of the rat.

In representative examples herein, many patients may require or benefit from the IOP lowering treatment complemented with neuroprotective therapy. In these cases, trans-pupillary sub-lethal photothermal stimulation therapy methods are performed optionally in association with systems configured for trans-scleral laser treatments for the reduction of IOP. Thus, system examples are operable to perform neuroprotective trans-pupillary sub-lethal photothermal stimulation therapy of the central retina, which can elicit biochemical responses that can result in neuroprotection, neuroenhancement and possibly regeneration of retinal ganglion cells (RGCs), including by way of example "starving, sick, but not yet dead" RGCs, for the goal of delaying, preventing, or even restoring the loss of visual functions in eyes with POAG and other retinovascular trophic neuropathies. According to examples herein, retinal sub-lethal photo-stimulation is achieved using annular (e.g., circular) treatments that produce an advantageous temperature distribution profile having a flat top histogram characteristic over the panmacular area (including the central fovea, if needed) that does not exceed 45-47 Celsius, and thereby avoids a central cumulative thermal peak rise with a gaussian like thermal peak profile. In some examples, a diode laser operating at a selected wavelength, e.g., 810 nm, in a repetitive micropulse emission mode (for the fine control of laser-induced thermal elevation at the RPE level) is directed in circular patterns irradiating an annulus, avoiding irradiation of a 1.0-2.0 mm central hole centered over the fovea, and expanding an external edge a predetermined distance, such as up to about 3 disk diameters (4.5-5.0 mm). In this way, the panmacular area of the eye can receive a safe hyperthermic stimulation including the foveal center region, which will not be directly heated by laser-induced-heating, but by indirect conductive-heating.

Example Systems and Methods for Trans Pupil and/or Trans-Scleral Treatments

Example interface apparatus 100 shown in FIG. 8A can be used to couple a non-contact laser system 74 (with a scan optic portion of the laser system being shown for simplicity) to an eye 70 that receives biostimulation treatment in accordance with method examples herein. In trans-pupillary method examples, a laser beam 71 is directed by the non-contact laser system (e.g., with a laser scanner) through a pupil of the eye 70 to the macular region of the retina of the eye 70.

Example optical scanning system 200, shown in FIG. 8B, can be configured to direct beams trans-sclerally and trans-pupillary. An optical beam source 206 emits an optical beam 202 that is directed through optics and with a laser scanner 214 (e.g., a two-axis or three-axis galvo-scanner) and focusing optics 220 to an eye 70. In representative examples, for trans-scleral processing, the optical beam 202 can have a wavelength of about 1475 nm based on emission from a 1475 nm diode laser of the optical beam source 206, and for trans-pupillary processing, the optical beam 202 can have a wavelength of about 810 nm based on emission from an 810 nm diode laser of the optical beam source 206. It will be appreciated that other wavelengths can also be used. In general, wavelengths can be selected based on the location and absorptivity (such as the absorbing chromophores) of targeted eye tissue. In some examples, the optical scanning system 200 is configured to direct the optical beam 202 at least one of trans-sclerally (e.g., 1475 nm) or trans-pupillary (e.g., 810 nm), as well as both.

Figure 17A:
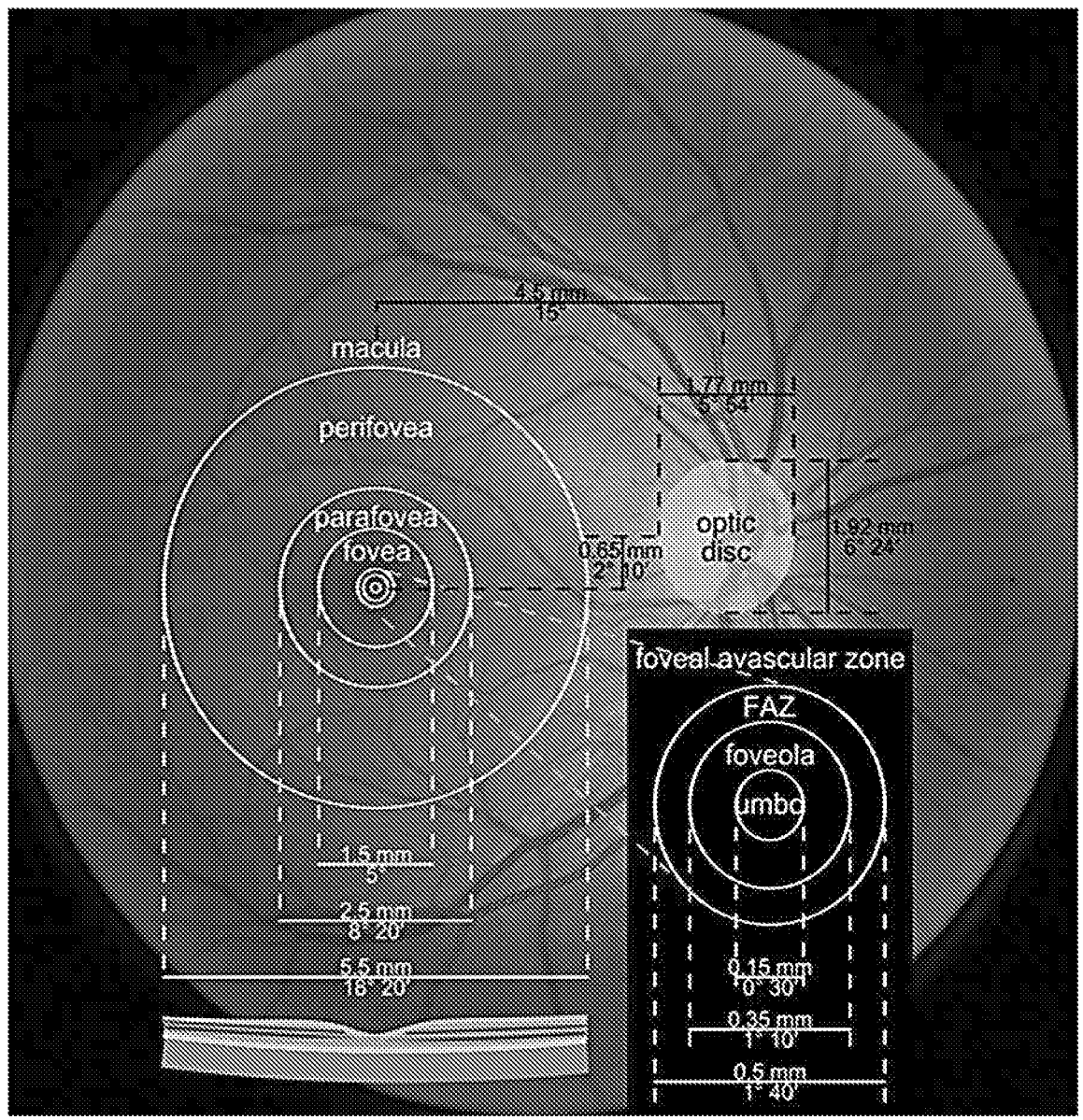
FIG. 17A is a retinal image similar to the image in FIG. 16 but showing target regions for pan-macular non-damaging laser photostimulation as viewed through the pupil. A cross-section of the macula is shown at the bottom of FIG. 4A and illustrates the varying thickness of the macula from its central to peripheral zones.
Figure 17B:
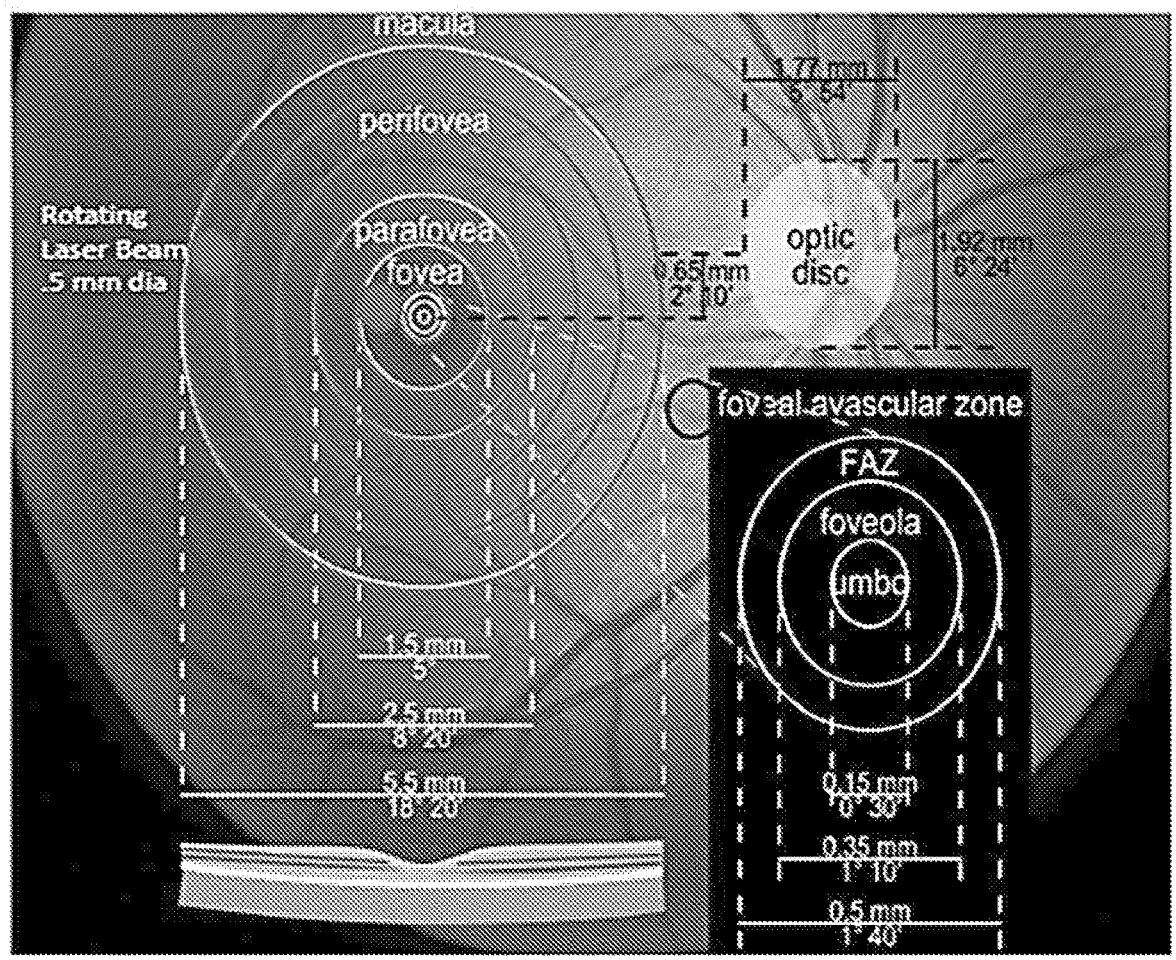
FIG. 17B is a schematic of a retina similar to FIG. 17A but including an example of a circular laser beam scan pattern.

In FIG. 17A, a macula of a retina is divided in a plurality of circular (or oval) regions concentric about an umbo, including a foveola, foveal avascular zone (FAZ), fovea, parafovea, and perifovea, in the order of increasing diameter and radial distance from the center of the umbo. Typical dimensions of the illustrated regions are shown. FIG. 17B shows a plurality of concentric paths for a laser beam directed to the macula to biostimulative treatment. With a spot size of about 0.5 mm, five adjoining concentric paths can span the area radially beginning at the FAZ and extending radially outward to the outer radius of the perifovea (e.g., from 0.25 mm from the center of the umbo to 2.75 mm from the center of the umbo). In some examples, predetermined values for spot size and scan pattern radii can be based on average or typical dimensions of the macula, and in further examples, radii and/or spot size can be adjusted or selected after imaging and examining a patient macula (e.g., through an anatomical estimation of dimensional differences, such as color, relative to a typical macula, by an expert or with machine learning image identification software tools).

Figure 18A:
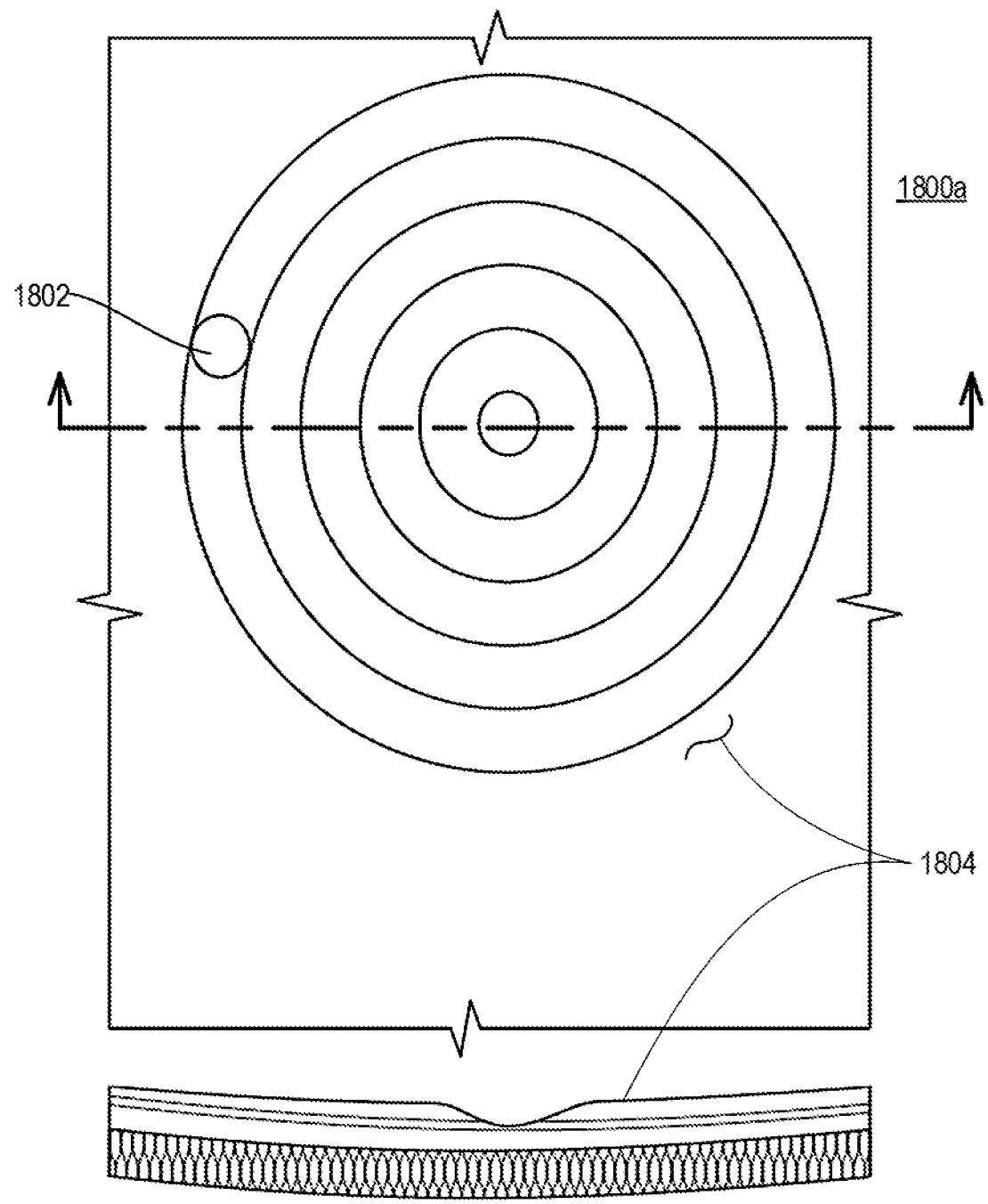
FIGS. 18A-18G is a series of retinal images similar to FIG. 17B, illustrating patterns of irradiation of the retina during later panmacular laser photostimulation treatment.
Figure 18B:
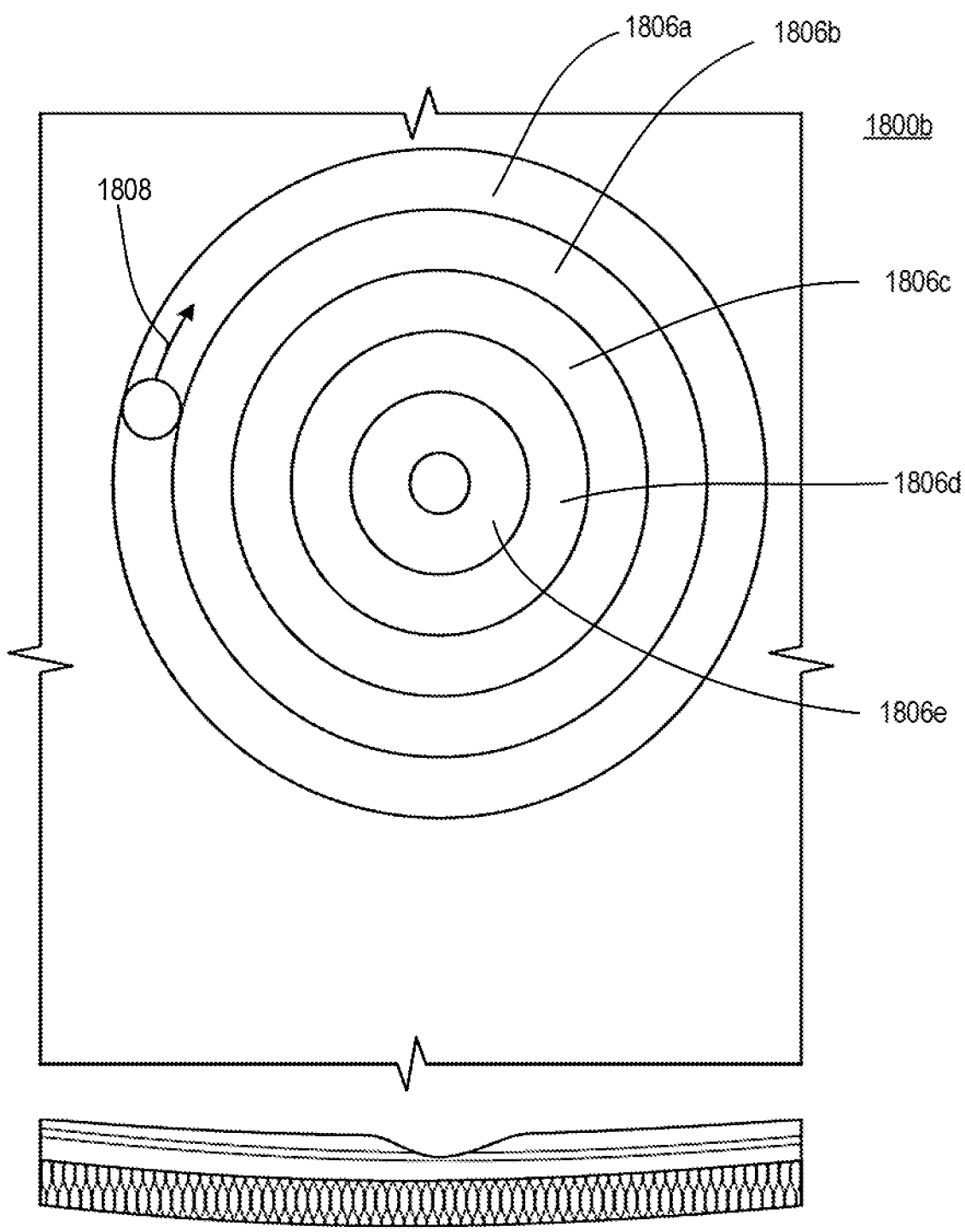
Figure 18C:
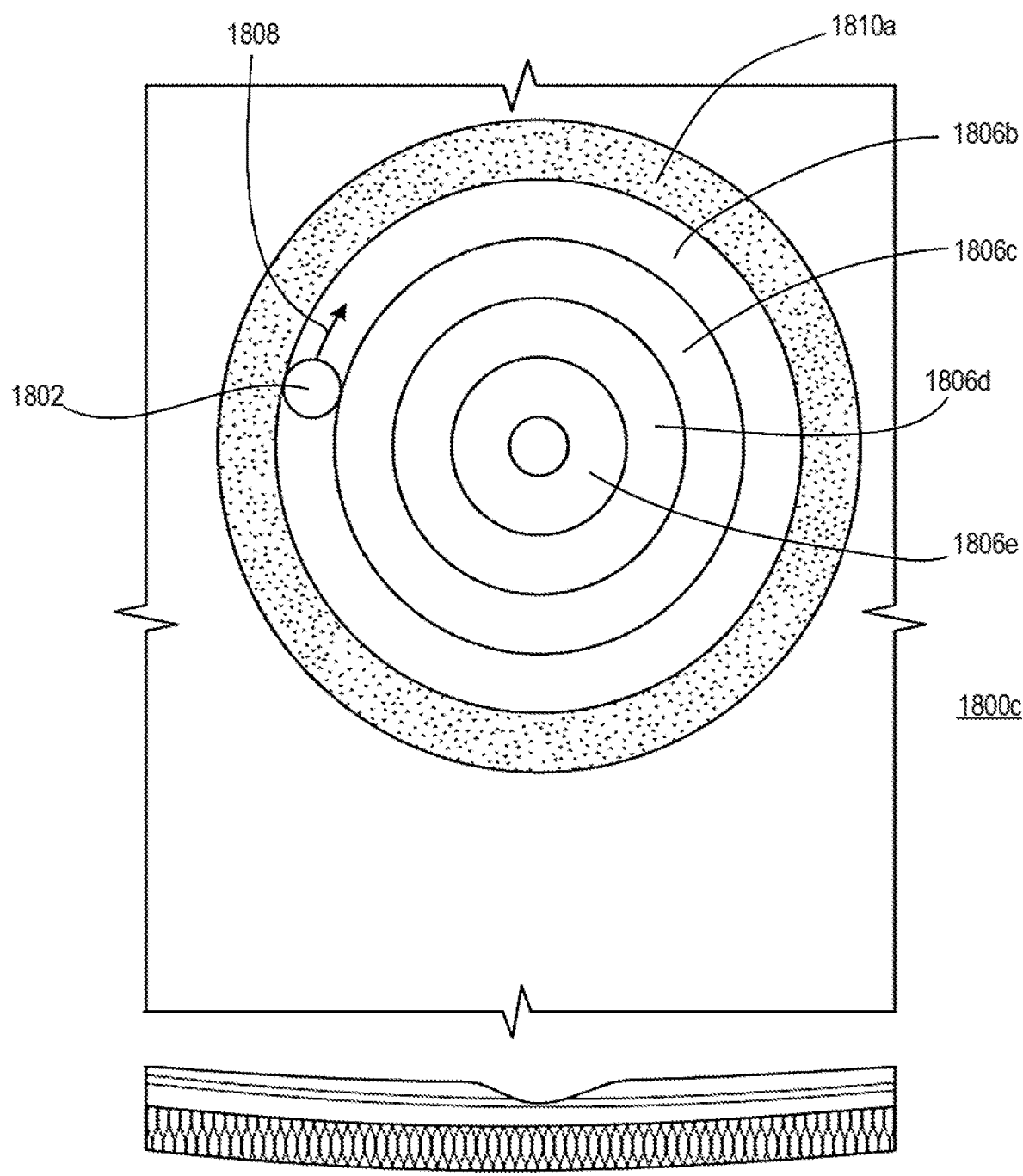
Figure 18D:
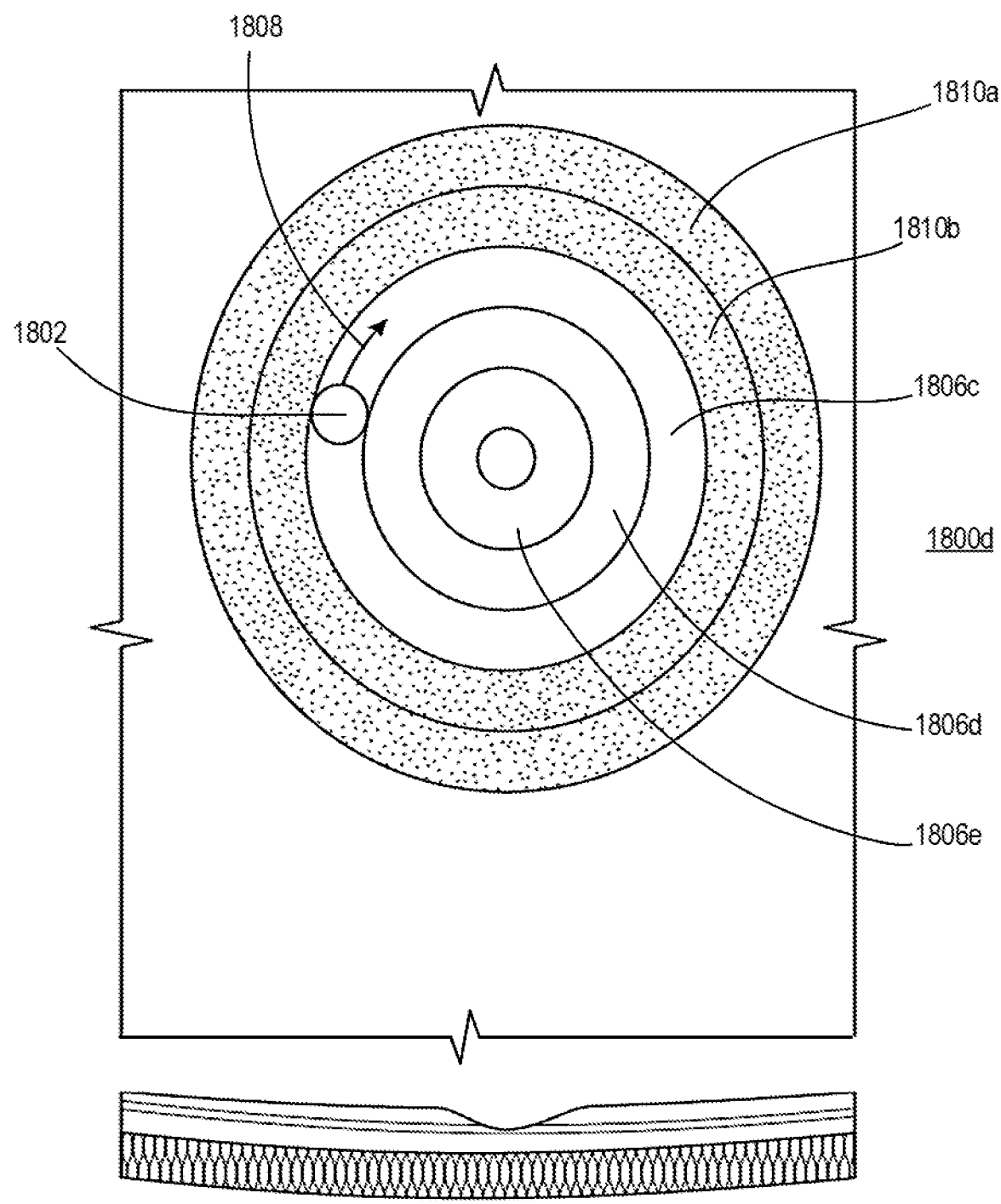
Figure 18E:
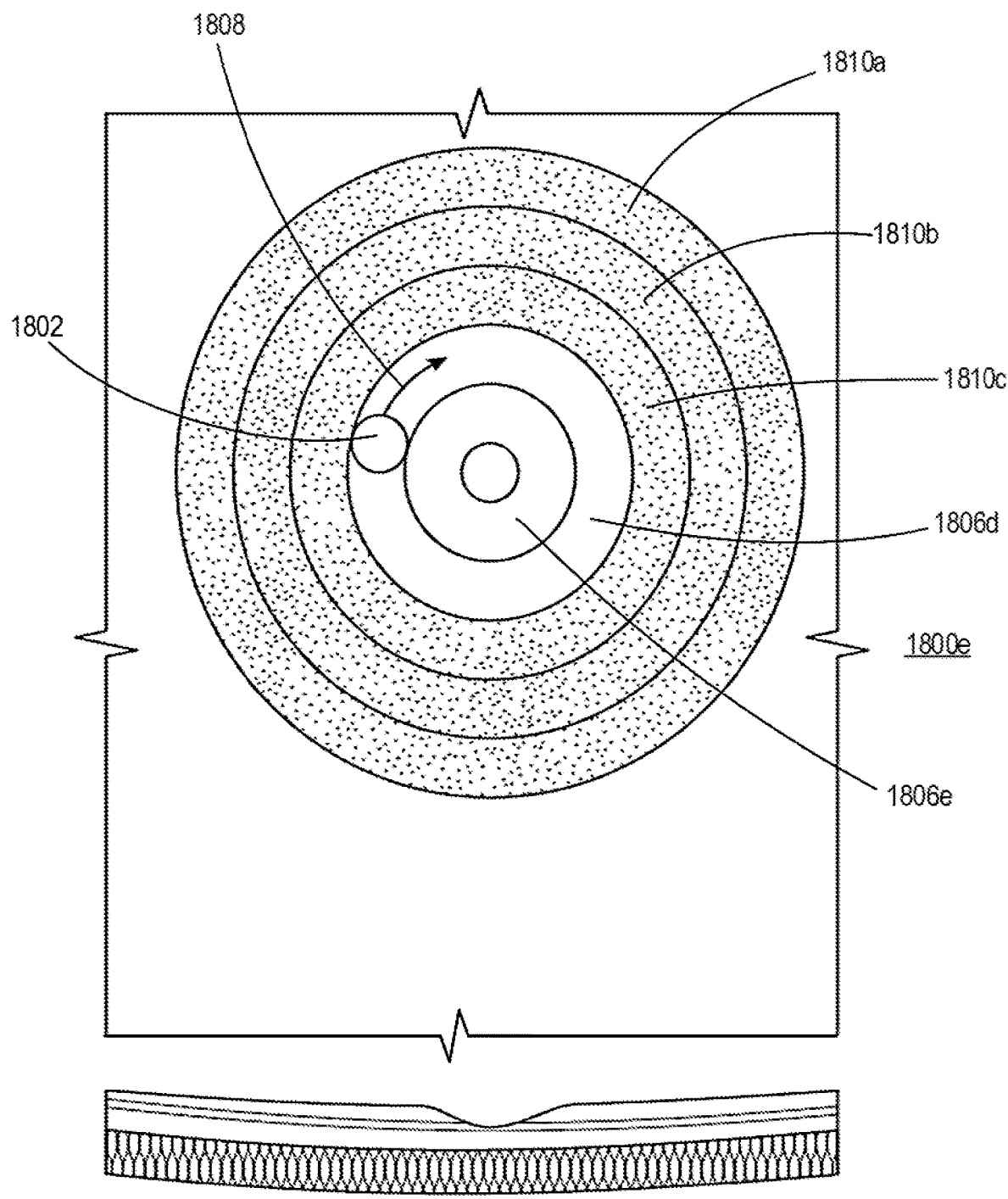
Figure 18F:
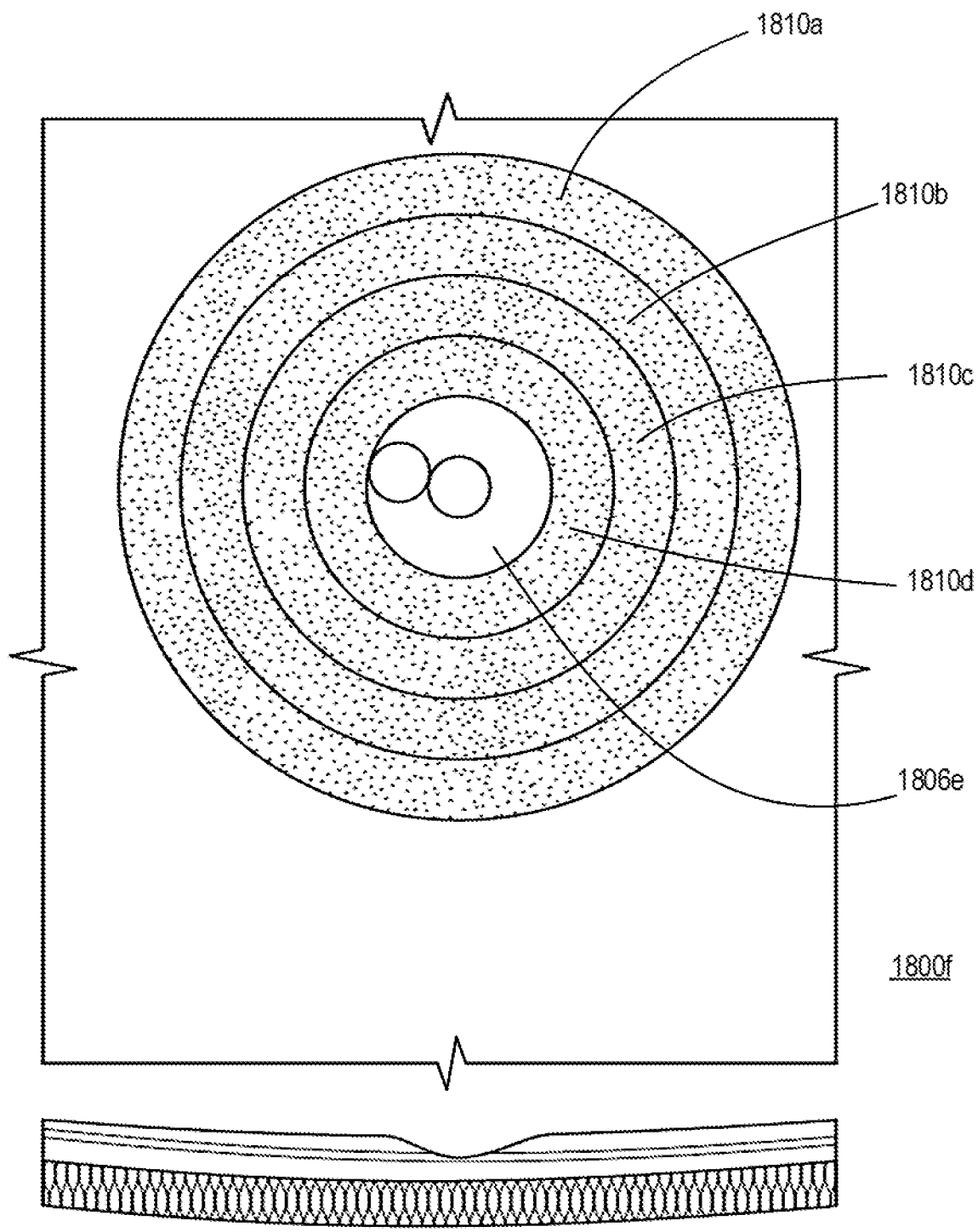
Figure 18G:
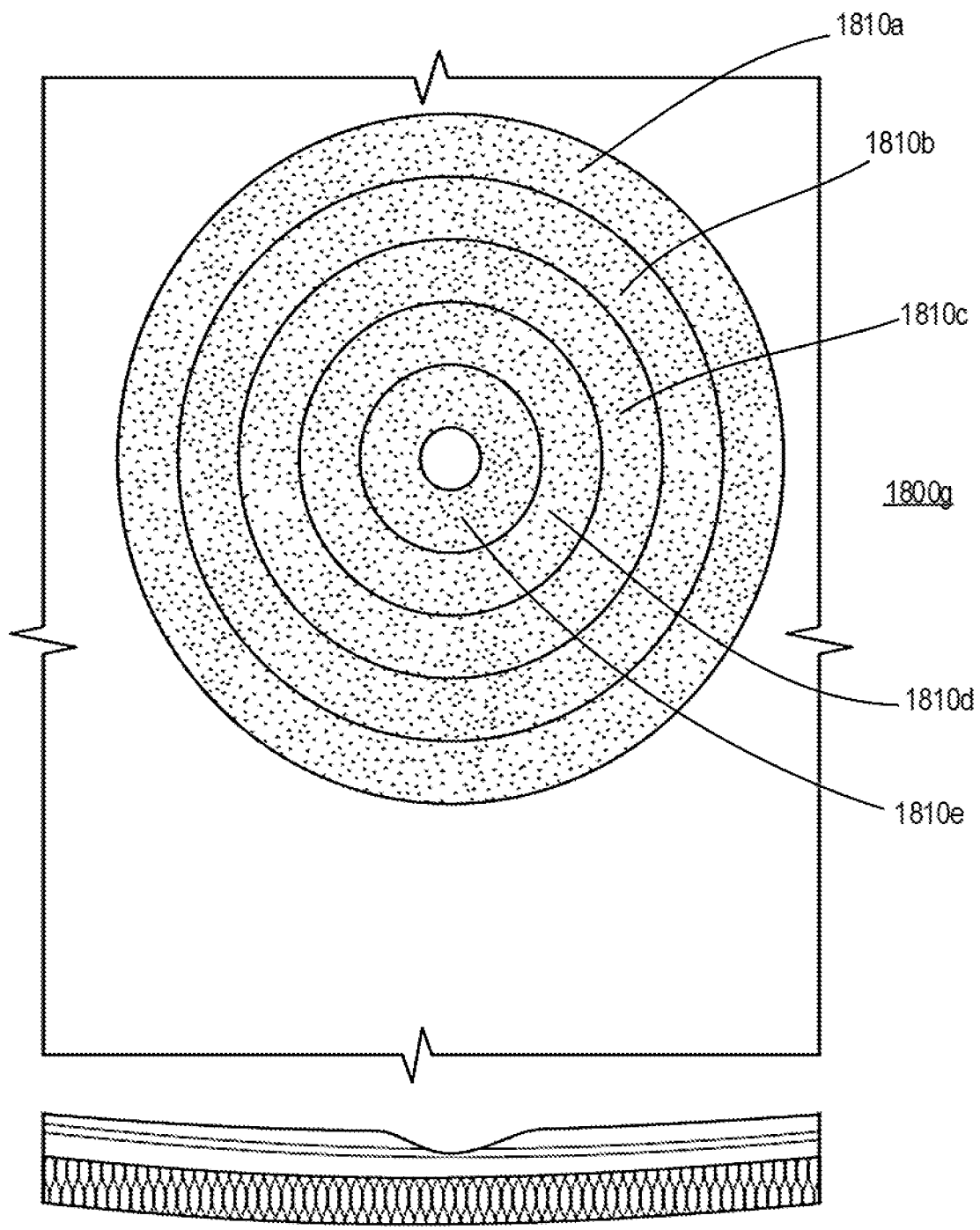

FIGS. 18A-18G depict an example trans-pupillary treatment method at different times during the treatment process. In FIG. 18A, at an initial time 500a, a spot 502 of a pulsed laser beam is directed through a pupil of a human eye and impinges at an outer location of a macula 504 (e.g., in or proximate the perifovea) of the eye. The macula 504 is shown on-axis through the pupil, with a cross-sectional depiction projected below the on-axis view. FIG. 18B shows a time 500b immediately after initial time 500a as the spot 502 is scanned in a clockwise direction along an unprocessed first annulus 506a of a curvilinear scan path 508 about the macula 504. Unprocessed second, third, fourth, and fifth annuli 506b-506e are also shown to adjoin each other at their neighboring beam boundaries to form a contiguous area for treatment that excludes the FAZ, foveolar, and umbo. In typical examples, the beam boundaries are defined as a radial location of the spot 502 where an intensity of the pulse of the pulsed laser beam drops to a predetermined value, such as full-width half-max (FWHM), 1/e, $1/e^2$, zero, etc. Beam intensity is preferably uniform across the spot, so as to avoid uneven heating or temperature spikes towards a spot center. Uniform intensity can be achieved through various ways, such as homogenizing light pipes, lens arrays, diffusers, etc. Spot size can be fixed in some examples, or adjusted with, e.g., a beam expander or other optics. FIG. 18C depicts a time 500c after the spot 502 has completed treatment of the unprocessed first annulus 506a to form a processed first annulus 510a. The spot 502 proceeds on the curvilinear scan path 508, now scanning clockwise along the unprocessed second annulus 506b. FIG. 18D shows a time 500d during laser treatment after the pulses of the pulsed laser beam have been scanned to complete a processed second annulus 510b. The spot 502 is then directed to begin scanning along the curvilinear scan path 508 around the unprocessed third annulus 506c. At a time 500e shown in FIG. 18E, the treatment process has formed a processed third annulus 510c, and the laser spot 502 is directed along the curvilinear scan path 508 to begin treating the unprocessed fourth annulus 506d with the pulses of the pulsed laser beam. FIG. 18F shows a time 500f during laser treatment after which processed annuli 506a-506d have been completed, and the scanning of the unprocessed annulus 506e is to begin. FIG. 18G shows a time 500g after the spot 502 has been directed consecutively directed through each of the unprocessed annuli 506a-506e to form the processed annuli 510a-510e. In selected examples, more or fewer than five annuli can be used, typically accompanying a different or variation in beam spot diameter.

Figure 19:
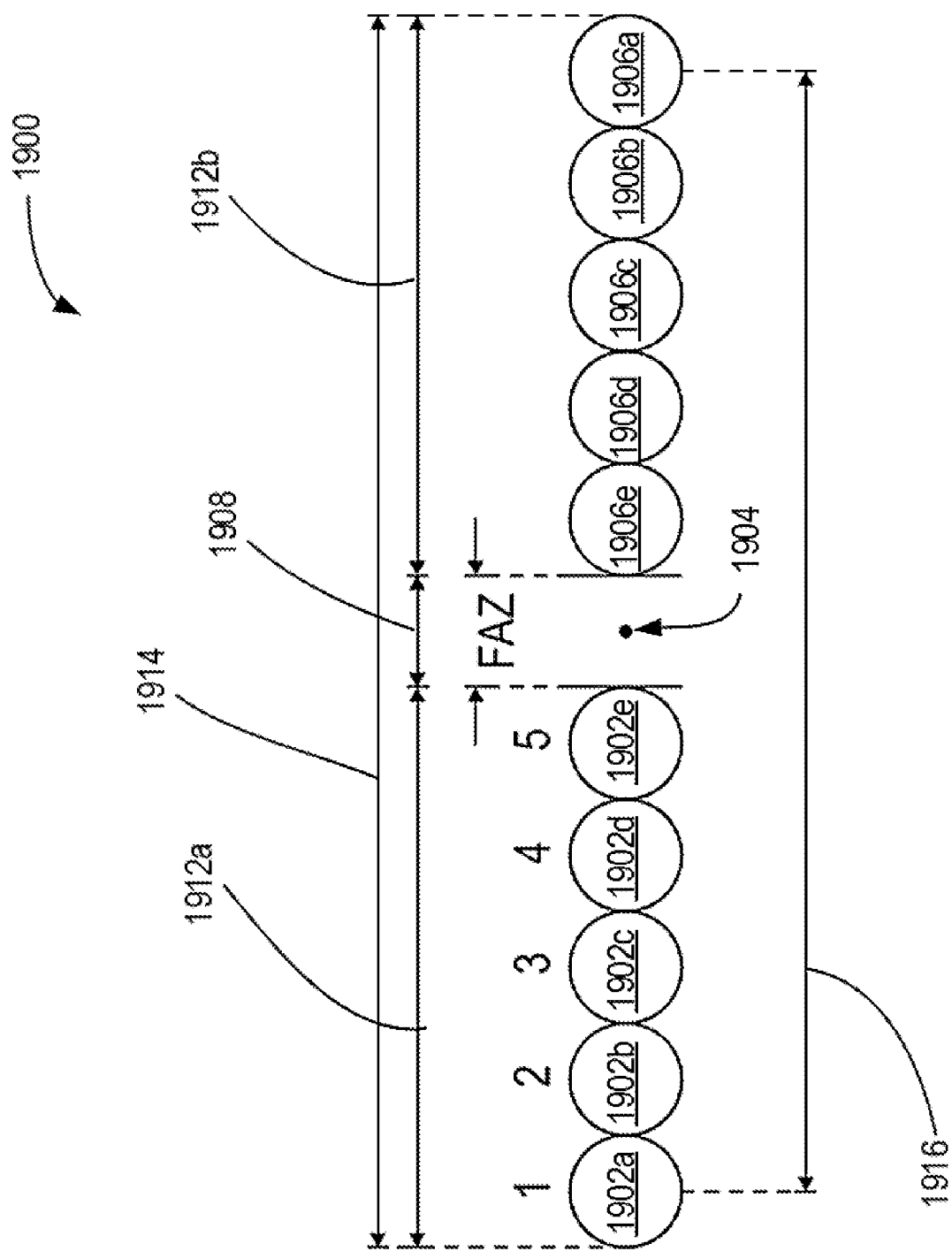
FIG. 19 is schematic showing the relative locations of laser spots with respect to the central fovea avascular zone (FAZ) applied to perform a central retinal photostimulation treatment.

FIG. 19 shows a dimensioned representation 1900 of the positions of beam spots 1902a-1902e at different distances from a central umbo position 1904, and the positions of beam spots 1906a-1906e arranged at opposite positions that corresponds to distances that are diameter lengths of respective concentrically arranged treatment annuli, such as the annuli 506a-506e shown in FIGS. 18A-18F. In representative examples, the FAZ is approximately 0.5 mm wide, and thus radially interior positions of the beam boundaries of the beam spots 1902e, 1906e define a distance 1908, and corresponding circular area during annular treatment, in which laser beam treatment does not occur through direct irradiation. In examples in which the size of the beam spots 1902a-1902e extending radially outward from the central umbo position 1908 is the same for each annulus and in which the boundaries of adjacent ones of the beam spots 1902a-1902e adjoin each other, cumulative radial lengths 1912a, 1912b can be defined, such as 2.5 mm for a common spot size of 0.5 mm Thus, an overall length 1914 can be defined for an outer treatment diameter, and an outer annulus diameter 1916 (aligned with a beam spot center) can be smaller by one radially extending spot size.

Figure 20:
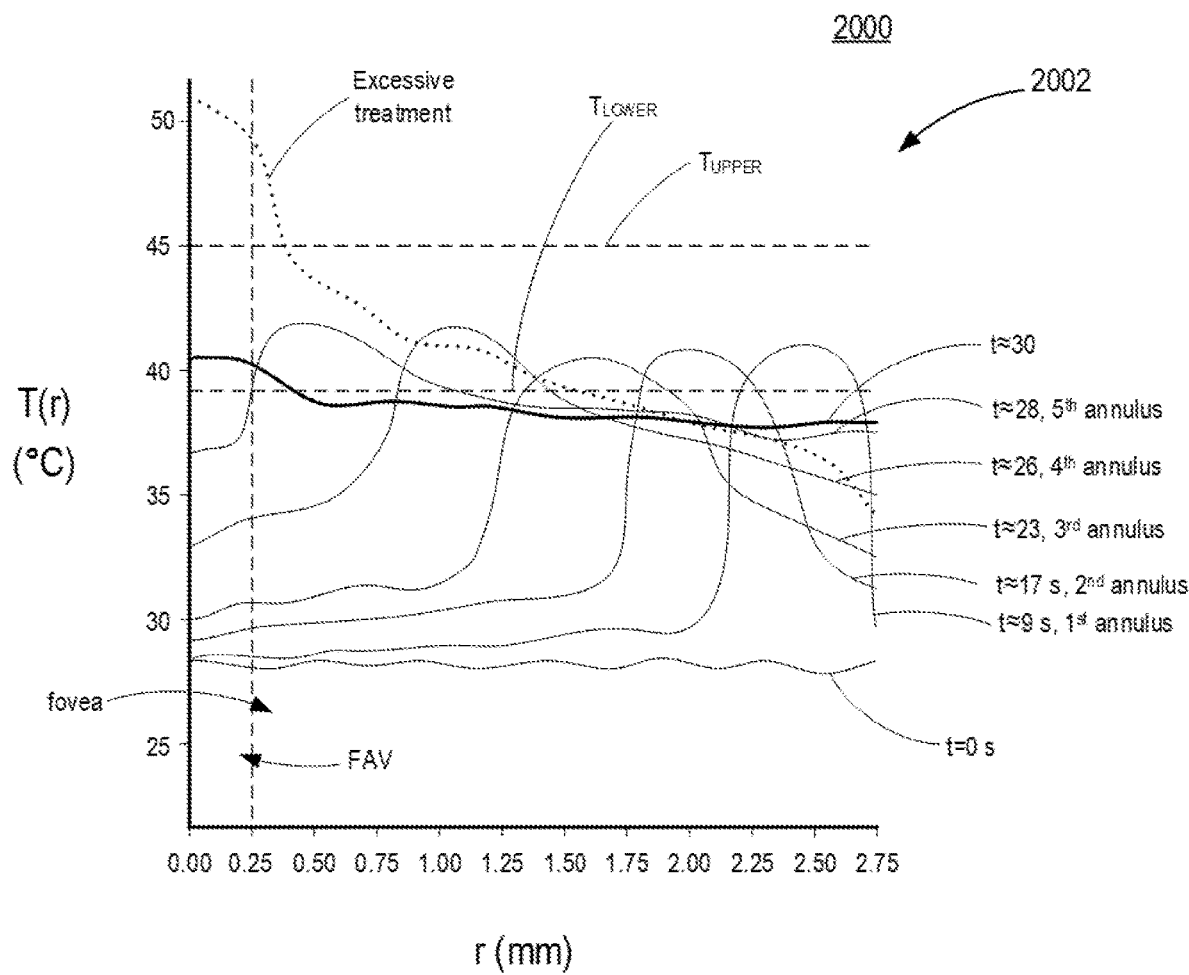
FIG. 20 is a graph illustrating an example of retinal heating gradients during treatment.

In FIG. 20, a graph 2000 shows a prediction of a time-evolved temperature profile 2002 of treating a macula region centered at an umbo at r=0 mm using an example set of parameters for a laser beam and scan pattern. The profile 2002 is produced with an annular pattern of a pulsed laser beam scanned about five annuli, with a first ring having a beam center radius of 2.5 mm, a second ring having a 2.0 mm radius, a third ring having a 1.5 mm radius, a fourth ring having a 1.0 mm radius, and a fifth ring having a 0.5 mm radius. A circular beam spot having a diameter of 0.5 mm at the macula defines an irradiative beam boundary that avoids direct irradiation of the FAZ, foveolar, and umbo of the macula. The spot size in the radial direction of the annuli and the annuli radii define a contiguous laser treatment area.

In a particular example, laser beam and scan parameters further include a constant scan speed of 1.66 mm/s during the scanning of one or more of the annuli thereby providing a 300 ms exposure time at each RPE cell irradiated by the beam spot diameter in the scanning annulus. It will be appreciated that other speeds can be selected so as to produce a range of exposure times in additional examples, such as 10 ms, 50 ms, 100 ms, 200 ms, 500 ms, etc. A series of processing pulses are generated and directed to the macula according to the annular pattern of five annuli at the constant scan speed. The processing pulses for the pulsed laser beam can have a pulse period of 2 ms (0.5 kHz pulse repetition rate) with a 5% duty cycle, corresponding to a processing pulse duration (FWHM, or other suitable metric) of 100 μs. At 1.66 m/s scan rate and 0.5 mm beam spot diameter, a pulse to pulse area overlap at the macula of greater than 99% is achieved, with an irradiation area density at the macula greater than 99%. When the peak power of the micropulse is set to 100 mW (e.g., with a duty cycle of 5% —0.1 ms "ON" and 2 ms period), this can correspond to an average power of 5 mW for a continuous wave (CW) equivalent setting. The power density (irradiance) for the laser micropulse at the macula is approximately 50 W/cm$^2$ (without considering absorption/scattering losses in the ocular media). In another example, the peak power of the micropulse is set to 1000 mW with the same 5% duty cycle, producing an average power of 50 mW for a continuous wave equivalent setting, and resulting in a power density at the macula of 510 W/cm$^2$. In accordance with different examples, laser and scan treatment parameters can be varied by selected amounts that achieve similar treatment effects, such as by varying values by 1%, 2%, 5%, 10%, 50%, 100%, etc.

With the aforementioned spot size and five annuli radii defining a contiguous scan area through the inner radial beam boundary of each annulus adjoining the outer radial beam boundary of the adjacent smaller annulus, a total area of about 23.5 mm$^2$ is treated with the processing pulses, resulting in the delivery of 141 mJ of total energy at a fluence of 600 mJ/cm$^2$, using a 100 mW micropulse peak power. This delivery can be similar to a fluence of about 760 mJ/cm$^2$ directly delivered to an RPE cell with 150 micropulses of 1 mJ each, over a duration of 300 ms. At a peak power for the micropulses in the range of 1.0-2.0 W, each 0.5 mm diameter area receives a total energy of 15-30 mJ. In general, repetitive pulse application at low duty cycle can reduce the significance of a total process fluence upon therapeutic effectiveness as time-based characteristics take on increased significance. Scan breaks or pauses can occur between annuli or during processing of an annulus, and can be selected to be repetitive or periodic, e.g., based on characteristics of the laser source generating the pulsed laser beam, such as a duty cycle defined for CW pulses, where the processing pulses are generated by modulating or chopping the CW pulses. As shown in the profile 2002 without scan breaks or pauses, the first ring can be completed after about 9 s, the second ring at about t=17 s, the third ring at about t=23 s, the fourth ring at about t=26 s, and the fifth ring at about t=28 s. By processing in a sequentially through the annuli, a temperature in the FAV, foveolar, and umbo can increase to be within a therapeutically advantageous range, e.g., between $T_{LOWER}$ and $T_{UPPER}$, without exceeding the range (e.g., by avoiding a temperature profile as depicted with the "excessive treatment" line). Thus, a temperature uniformity across the macular treatment area can be improved and Gaussian heat spikes associated with the central macular area can be avoided or reduced.

Figure 21:
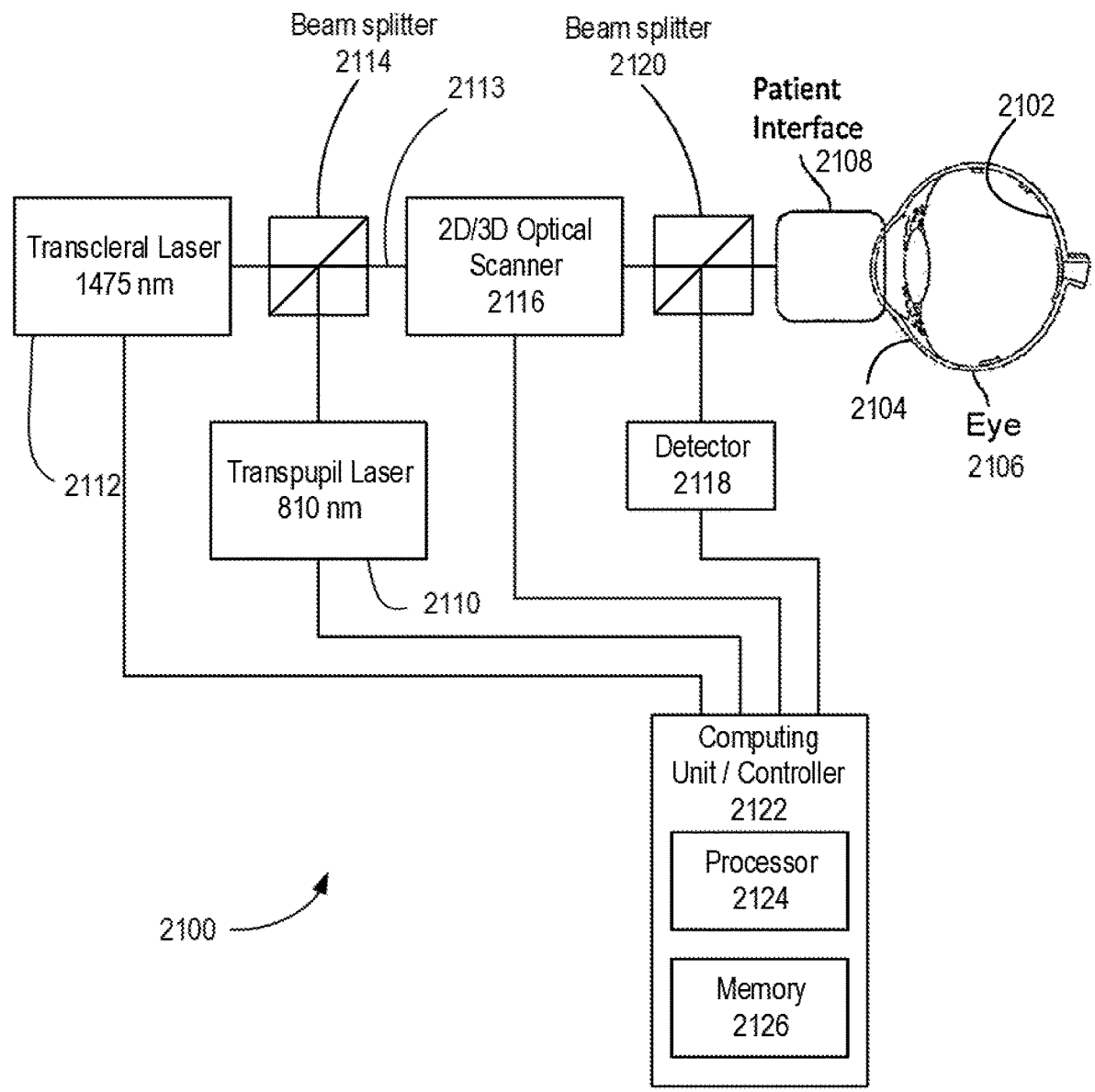
FIG. 21 is a schematic of an example optical imaging and scanning system.

FIG. 21 shows an example of an apparatus 2100 that can be used for treating the retina 2102 and/or sclera 2104 of an eye 2106 of a treatment subject (typically human), as well as other target tissue of the eye 2106. The apparatus 2100 includes a patient interface device 2108 that couples the apparatus 2100 to the eye 2106. The apparatus 2100 includes a light source that includes a plurality of laser sources, such as a trans-pupillary laser source 2110 that can generate laser pulses at predetermined durations, repetition frequencies, powers, duty cycles, etc., at a wavelength of 810 nm, and a trans-scleral laser source 2112 that can generate a continuous-wave laser beam at 1475 nm. In different examples, other additional laser sources can be used, and other laser source characteristics, including continuous-wave or pulsed, wavelength, power, etc., can be selected based on the eye tissue targeted and the type of laser treatment process used for the targeted eye tissue.

The plurality of laser sources can be directed to propagate along a common optical path 2113 with a beam splitter 2114. An optical beam scanner 2116, such as a two-axis or three-axis galvanometer scanner, is coupled to the common optical path 2113 to receive the laser beam from the plurality of laser sources and directs the beam towards a predetermined location of the eye 2106 according to a predetermined scan pattern, depending upon on the treatment process selected. In representative examples, a detector 2118, such as a camera, photodiode, CCD, CMOS, imaging system (such as an OCT system), etc., is optically coupled to the eye 2106, e.g., through a beam splitter 2120. As shown the optical coupling for the detector 2118 is between the optical beam scanner 2116 and the patient interface device 2108, though other positions are possible, including between the beam splitter 2114 and the optical beam scanner 2116. The detector 2118 can be used, for example, to monitor a position of the eye tissue that will be processed or that is being processed, so that the optical beam scanner 2116 can direct the laser beam or beams from the plurality of laser sources to the targeted locations of the eye 2106. In some examples, the working distance of the laser beam or beams is substantially larger than a propagation distance difference between the scleral tissue and the retinal tissue, such that a commanded focal plane does not change during processing different portions of the eye 2106. In further examples, the commanded focus can vary, e.g., between a location at the sclera and at the retina, or at different locations of the sclera or retina.

The plurality of laser sources, such as the laser sources 2110, 2112, the optical beam scanner 2116, and the detector 2118 can be coupled to a computing unit 2122. The computing unit 2122 includes a processor 2124 and a memory 2126 having stored instructions executable by the processor 2124 for controlling laser treatment, such as laser beam characteristics, laser wavelength selection, pulse repetition rate, duty cycle, beam initiation, scan pattern commands, and eye registration and/or scan calibration, by way of example. The memory 2126 can be configured with one or more pattern command files defining scan positions and paths for directing the laser beam with the optical beam scanner 2116 in relation to the patient interface 2108 with the eye 2106 in a predetermined position. In some examples, the computing unit 2122 can also receive signals from the detector 2118 and use the received signals to generate an image of the eye 2106 before, during, and/or after treatment. In some examples, the detector 2118 can provide location information for the eye 2106 so that pattern command files can be updated so that scanning can be performed in relation to the detected location information. Suitable location information can include anatomical reference features, color variations, reflectivity variations, etc. In some examples, the detector 2118 can be configured to detect a temperature of the target eye tissue, e.g., with a pyrometer, and the detected temperature can be used to adjust laser beam characteristics, such as pulse duration, peak power, repetition rate, etc., including in situ during treatment. In some examples, the memory 2126 is configured with instructions for the processor 2124 to control and direct delivery to macular annuli a total laser energy in the range of 1 J to 3 J in an annular processing area surrounding the foveal avascular zone of 20 mm² to 30 mm² (e.g., 23.5 mm²) at a peak pulse power in the range of 1 W to 2 W, and to deliver to annuli on the sclera in the form of N continuous-wave cycles at a constant scan speed in the range of 5 mm/s to 200 mm/s at a scleral radius and along a circumferential arc length that corresponds to a cycle duty factor for the annuli in the range of 0.5% to 50% and that does not produce photocoagulative effects with temperature rise in the range of 8° C. to 20° C. and exposure times proportionally reduced. Suitable values can be determined from clinical practice on specific patient cohorts. For example, treatment parameters providing subthreshold non-damaging pan-macular laser photo-thermal-stimulation for diverse patients may vary with different ethnicity, pigmentation, morphology, ocular characteristics and glaucoma conditions. In particular, the non-uniformity or great variability of the distribution of melanin (the main absorbing chromophore) in the human retinal pigment epithelium RPE, tends to alter the photo-thermal effects more than laser pulse fluence parameters. Energy values can be determined from or vary based on selected wavelength, including pigmentation variation among patients, and can affect and determine suitable thermal elevations. Such delivery to macular annuli can correspond to delivery of repetitive pulse trains of 150 micropulses over each consecutive 300 ms period, a laser spot diameter of 500 μm, a laser spot area of 0.00196 cm², an irradiance range of 510 to 1020 W/cm², a single micropulse duration of 0.1 ms in an energy range of 0.1 to 0.2 mJ producing a 150 pulse exposure energy range of 15 to 30 mJ and a single micropulse fluence of 51 to 102 mJ/cm².

For example, in a clinically validated and documented study, laser parameters using other retinal laser devices performed successful and effective non-damaging pan-macular photostimulation retinal treatments, and example devices herein can be controlled to deliver laser exposures similar to such clinically validated procedures. The laser parameters included an 810 nm diode laser operated in a micropulse emission mode at 5% duty cycle of a 2.0 ms period (0.1 ms ON+1.9 ms OFF) and 500 pps repetition rate, an exposure duration of 300 ms (delivering a train of 150 micropulses), a laser spot diameter of 500 μm, a laser spot area of 0.00196 cm², a laser power of 1.7 W, an irradiance of 867 W/cm², a single micropulse (0.1 s) energy of 0.17 mJ, a 150-pulse exposure total energy of 25.5 mJ, and a single micropulse fluence 86.7 mJ/cm². Each single RPE cell, with 10-14 μm diameter and a macular area density of about 4,220±727 cells/mm² (Songhomitrapanda-Jonasm D. et al., Retinal Pigment Epithelial Cell Count, Distribution, and Correlations in Normal Human Eyes. *AJO* Volume 121, Issue 2, February 1996, Pages 181-189) targeted by the 0.00196 cm² area of the 500 μm diameter spot was irradiated with a train of 150 consecutive micropulses with the above parameters. In example annular macular treatment patterns described herein without overlap, RPE cells at the edges of a selected annulus can be exposed to laser energy for a shorter duration relative to portions more central to the selected annulus (due to the circular shape of the spot) and will receive less energy (e.g., fewer than 150 pulses). However, this reduction can be compensated by the proximity the photo-thermal-stimulation effects from an adjacent treatment annulus. In some examples, a radial overlap of adjacent annuli can be provided to reduce a fluence variation in the radial direction.

Figure 22:
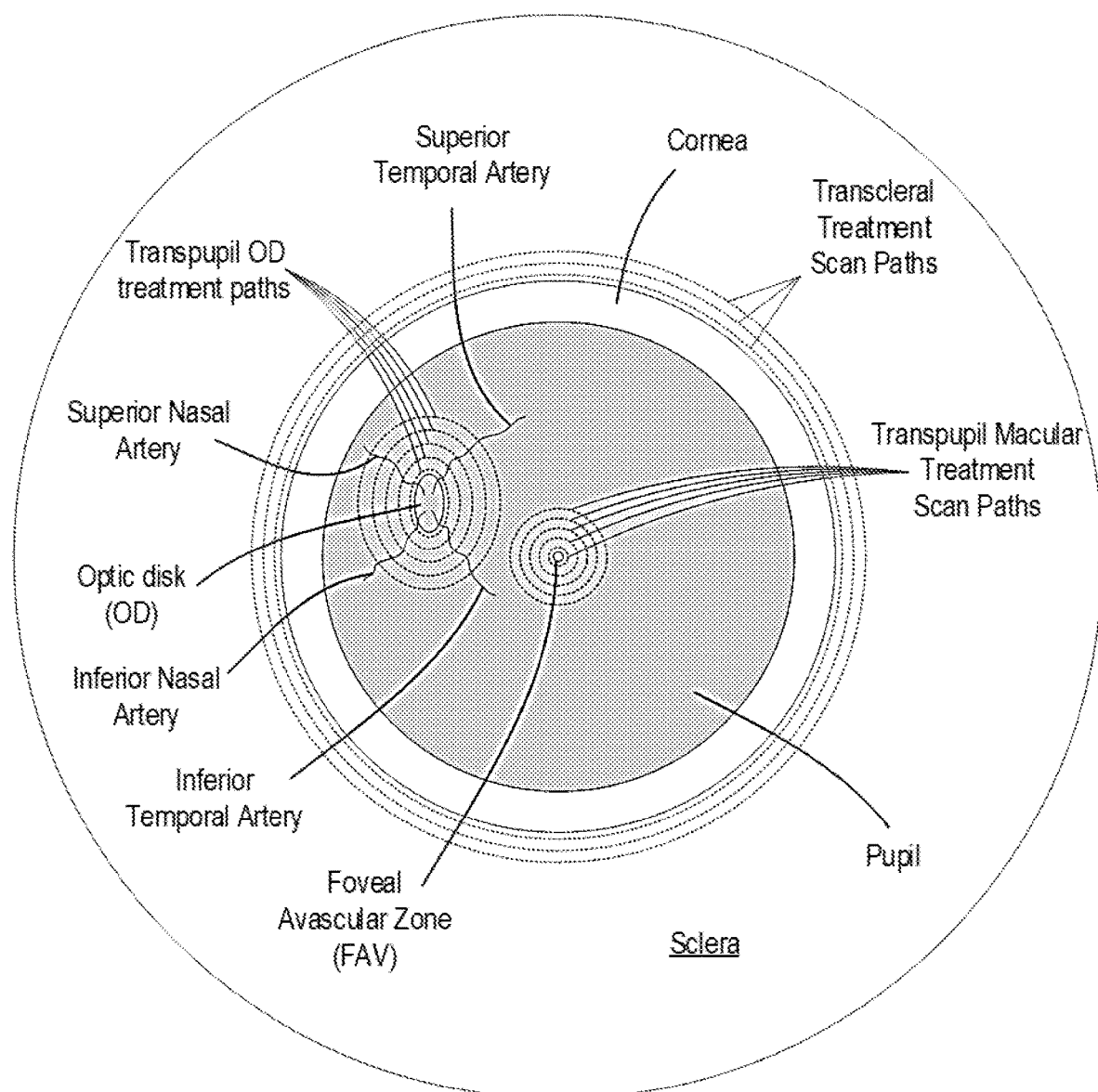
FIG. 22 is an end view schematic of an example treatment scan pattern that treats both the sclera and retina.

In a representative treatment example that combines scleral and retinal treatments, the one or more pattern command files can include a first set of pattern commands for a trans-scleral treatment, a second set of pattern commands for a trans-pupillary treatment proximate a macula, and a third set of pattern commands for a trans-pupillary treatment proximate an optic disk. In particular, some treatments can be applied prophylactically, such as before an onset of glaucoma or without an indication of glaucoma, to reduce the probability of glaucoma occurring or retard glaucoma development. For example, it can be determined from a patient's family history, genetics, or population clusters, whether predisposition towards certain eye diseases is more likely, and treatments can be applied based on positive determinations. Alternatively, other treatments can be applied any indicators or with few or less dispositive indicators, to provide a neuroprotective therapy that can slow, stop, and/or reverse neurodegenerative progression. A view of an eye shown in FIG. 22 shows an example of trans-scleral treatment annular scan paths and trans-pupillary treatment annular scan paths overlaid on the eye. The trans-scleral pattern commands can be configured to control beam characteristics and to direct the beam to a plurality of treatment locations 0-4 mm posterior to the corneolimbal junction on an external surface of the sclera 2104. At least one (and typically all) of the treatment locations can include a curvilinear or arcuate scan path segment of a predetermined length (e.g., a full circle or an arcuate portion thereof), and the laser beam, operating a continuous-wave mode (though a continuous series of pulses can be used in some examples), is repetitively directed to scan along the same scan path segment at a predetermined scan speed. The length and scan speed can define a duty factor for the repetitions that is sufficient to induce protective thermal preconditioning and therapeutic bio-stimulation of one or more of the trabecular meshwork and/or ciliary body of the eye. In some examples, the plurality of trans-scleral treatment locations are defined by three concentric circular scan paths at different diameters in the range of 0-4 mm posterior to the corneolimbal junction on an external surface of the eye (e.g., 1 mm, 2 mm, and 3 mm, 1.5 mm, 2.5 mm, and 3.5 mm, etc.), with each circular scan path including a single scan path arc segment forming a complete circle or less than a complete circle or including multiple arcuate segments including contiguous, spaced apart, and/or overlapping segments. In a particular example, each of circular scan paths includes a superior 150° arc from 9:30 to 2:30 o'clock and an inferior 150° arc from 3:30 to 8:30 o'clock while avoiding the nasal and temporal 30° arcs.

The second set of trans-pupillary treatment commands can be configured to control beam characteristics and to direct the beam to a plurality of treatment locations at the macular region of the retina 2102 exclusive of the FAZ, foveola, and umbo. In a representative example, the plurality of treatment locations includes five annular scan paths concentric about the FAZ, scanned in a sequence from the outer-most larger diameter annulus to the inner-most smallest diameter annulus. An inner most annulus has an inner beam boundary that adjoins or is adjacent to the FAZ so as to avoid direct irradiation of the FAZ, and, beginning with the inner most annulus, each outer beam boundary adjoining or adjacent to (or overlapping in some examples) the next larger diameter annulus so as to form a contiguous treatment area. With a beam dimension of 0.5 mm in the radial direction outward from the FAZ and with adjacent annuli having adjoining boundaries, the outer most annulus of the five annuli can have an outer beam boundary at a radius of 2.75 mm for a typical human eye macula. In other examples, fewer or more than the five annuli can be scanned, and different beam spot dimensions in the radial direction can be used. In typical examples, the beam spot is circular resulting in a common value for the beam spot dimension along the direction of scanning and the beam spot dimension in the radial direction from the umbo, and in further examples oval, square, rectangular, or other non-circular beam spot shapes can be used. The treatment annuli can be scanned in a sequence from largest diameter to smallest, and the sequence can be associated with a suitable temperature increase in the FAZ, foveola, and umbo to within a therapeutic temperature range, such as between 37-47° C. In some examples, the thickness of different annuli can be different.

The beam characteristics for the laser beam targeting the macular region can include pulsed operation with selectable pulse characteristics. For example, the pulse repetition rate and curvilinear scan speed can be selected such that each individual retinal pigment epithelium (RPE) cell within the laser treatment area receives approximately 150 pulses. To achieve such delivery for a circular beam spot having a diameter of 0.5 mm at the macula, a scan speed of 1.666 mm/s and a pulse repetition rate 0.5 kHz (2 ms pulse period) can be used, thereby irradiating approximately 150 pulses over 300 ms. With a suitable pulse duration and peak power selected (e.g., 100 μs and 100 mW), a time-temperature history of 150 consecutive small non-lethal temperature spikes can be created for each RPE cell, each spike producing a very high rate of temperature change that elicits a biological stress response but that does not kill the RPE cell. In creating a non-lethal 7° C. gradient with a rising front of 0.1 ms, each spike can infer to the cell a thermal shock at a rate of approximately 70,000° C./second.

The third set of trans-pupillary treatment commands can be configured to control beam characteristics and to direct the beam to a plurality of treatment locations proximate the optic disk region of the retina 2102 but exclusive of the optic disk and underlying optic nerve (e.g., by having irradiated laser light avoid substantial impingement on the area bounded by the dura mater of the optic nerve). The plurality of treatment locations can include a similar scan pattern as the second set of trans-pupillary treatment commands, but instead navigating around the optic disk. For example, the plurality of treatment locations can include five annular scan paths concentric about the optic disk, scanned in a sequence from the outer-most larger diameter annulus to the inner-most smallest diameter annulus. An inner most annulus has an inner beam boundary that adjoins or is adjacent to the optic disk so as to avoid direct irradiation of the optic nerve, and, beginning with the inner most annulus, each outer beam boundary adjoining or adjacent to (or overlapping in some examples) the next larger diameter annulus so as to form a contiguous treatment area. With a beam dimension of 0.5 mm in the radial direction outward from the major diameter (~1.92 mm) of the optic disk and with adjacent annuli having adjoining boundaries, the outer most annulus of the five annuli can have an outer beam boundary at a radius of 3.46 mm for a typical human eye optic disk. With oval-shaped paths matching the oval shape of the optic disk, the five annuli can be oval-shaped, e.g., with an outer beam boundary along a minor diameter (~1.76 mm) direction at a radius of 3.38 mm for a typical human eye optic disk. In other examples, fewer or more than the five annuli can be scanned, and different beam spot dimensions in the radial direction can be used. In typical examples, the beam spot is circular resulting in a common value for the beam spot dimension along the direction of scanning and the beam spot dimension in the radial direction from the optic disk center, and in further examples oval, square, rectangular, or other non-circular beam spot shapes can be used. The treatment annuli can be scanned in a sequence from largest diameter to smallest, and the sequence can be associated with a suitable temperature increase in the areas having retinal cells surrounding the optic disk to within a therapeutic temperature range, such as between 37-47° C. In some examples, the thickness of different annuli can be different.

Figure 24A:
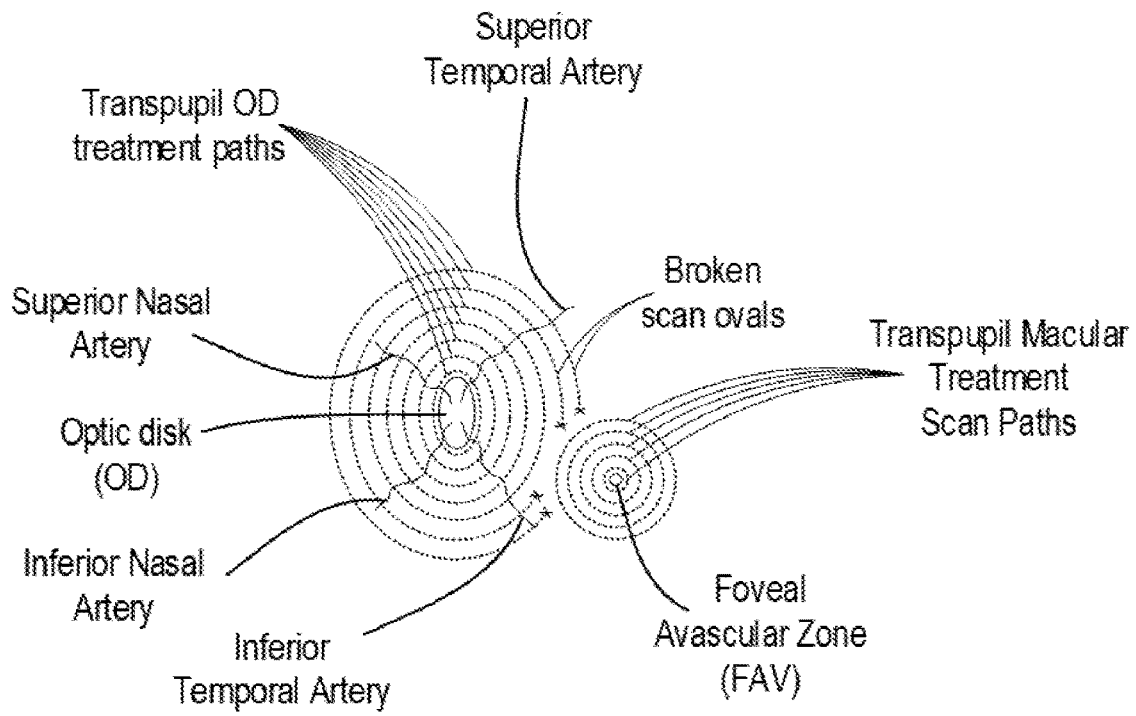
FIGS. 24A-24C illustrate retinal areas and example laser treatment patterns.
Figure 24B:
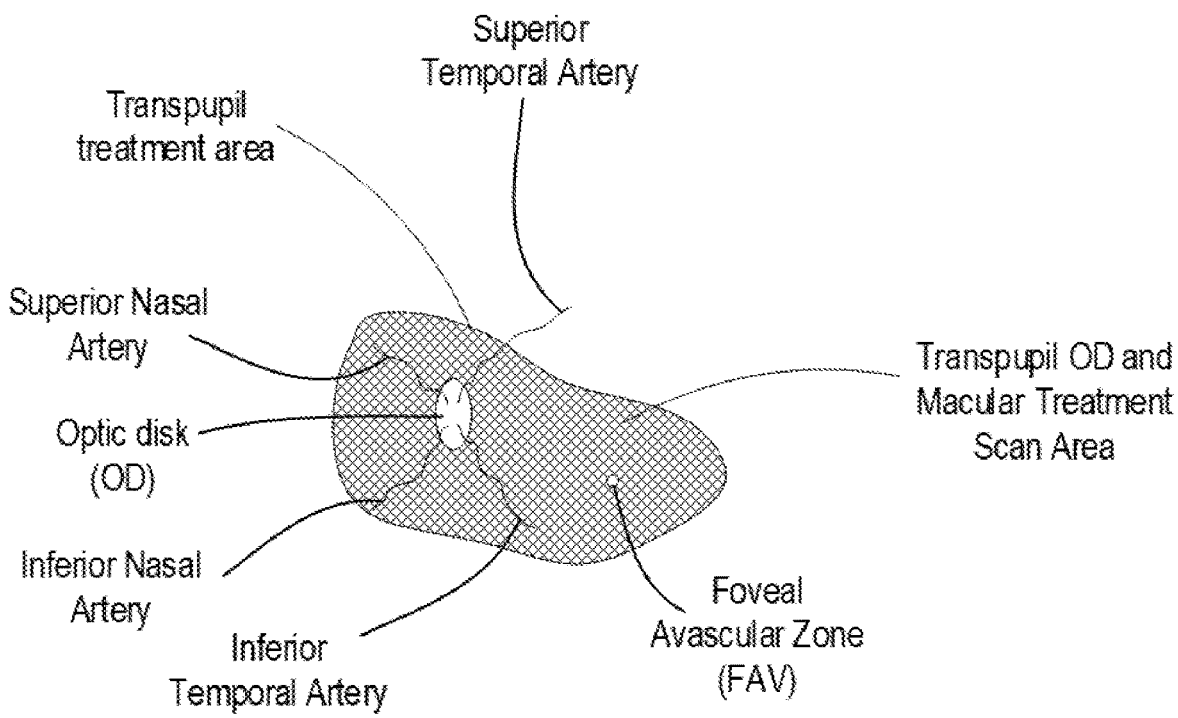
Figure 24C:
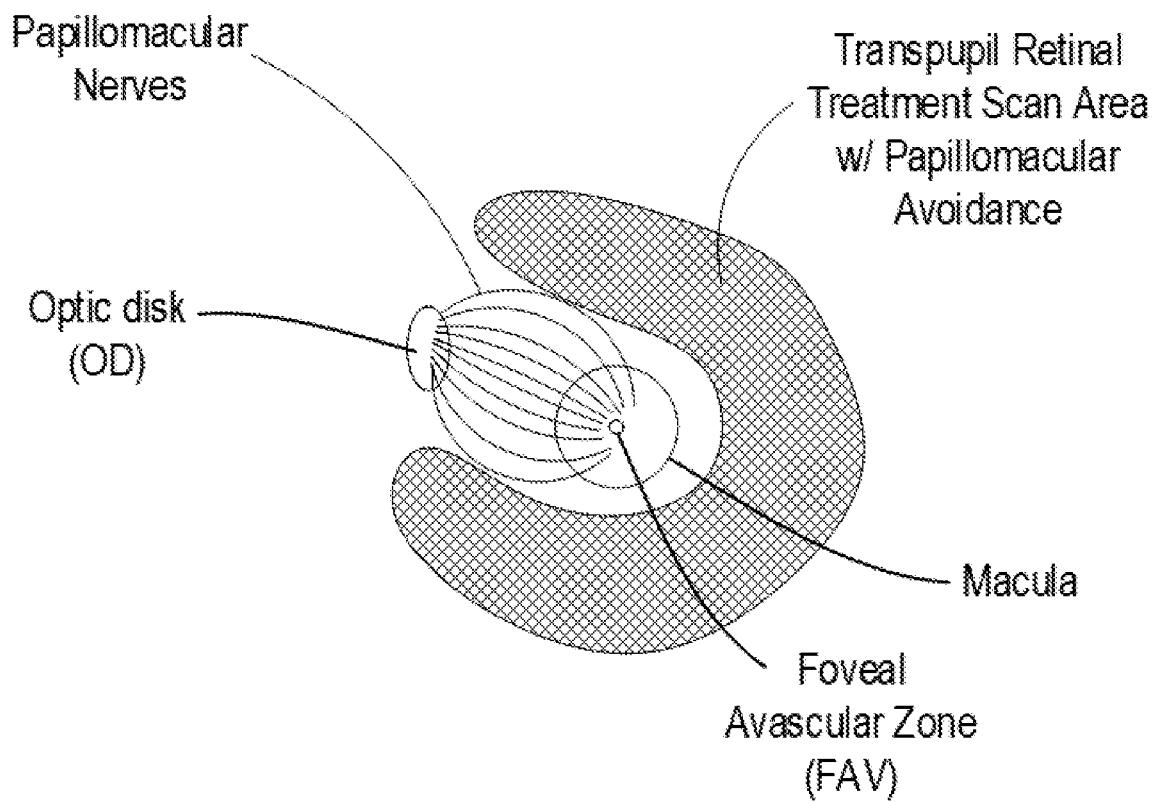

Because of the proximity between the macula and the optic disk at the fundus of the typical human eye, examples of annuli formed with the second and third sets of trans-pupillary treatment commands can be made to overlap at the fundus, resulting in double-stimulation treatment of selected areas. Examples herein can also include avoidance of double-treatment, by changing scan patterns associated with the second and/or third sets of trans-pupillary treatment commands so that beam spots delivered along one beam scan paths (such as a path encircling the macula) do not substantially overlap beam spots delivered along an adjacent beam scan path (such as another path encircling the optic disk). Additional treatment pattern options are shown in FIGS. 24A-24C. In FIG. 24A, trans-pupillary treatment commands produce example laser scan paths proximate the optic disk that generally follow the oval contour of the optic disk. Where trans-pupil macular treatment commands are provided, to avoid excessive treatment the processed areas proximate the macula (or in the foveal avascular zone), scan paths can be adjusted to terminate to prevent an overlap, such as with the broken scan ovals shown. FIG. 24B shows a trans-pupillary treatment area that surrounds and avoids the optic disk and the foveal avascular zone. In some examples, a scan path or paths defining the trans-pupillary treatment area can include contoured circles and ovals (similar to that shown in FIG. 24A), but other scan paths can be chosen as well to "paint" the selected treatment area proximate the optic disk and macula. In typical examples, the scan path of the laser beam treats the area without overlapping scan path segments in one pass, though in additional examples paths can be retraced. As discussed herein, treatment parameters are selected to produce sub-threshold sublethal laser photostimulation of the retina that triggers a stress response by targeting retinal pigment epithelium (RPE) cells through continuous scanning of a laser beam according to predetermined scan patterns and with selected CW or pulsed laser parameters and laser scan parameters. FIG. 24C shows another example treatment pattern in which an area of the retina is targeted for sub-threshold sublethal laser photostimulation but an area corresponding to the position of a papillomacular nerve bundle is avoided. As shown a macular area, including a perifovea and other macular areas outside an FAZ, is avoided, but in some examples, a macular area exclusive of the papillomacular nerve bundle or including the papillomacular nerve bundle can be treated.

In some examples, the second and third sets can also be combined to form a single set of treatment commands By using OCT or another imaging device, the macula and optic disk can be located and their positions determined, and the second and third sets of treatment locations and corresponding treatment commands can be defined in relation to the determined positions. While locations can be found by a trained person performing treatment, representative examples can use a coupled control device to compare detected features of the patient's fundus with images or schematics depicting macula and optic disks. For example, detected features can be processed through one or more image identification or pattern recognition algorithms (such as deep learning, convolutional neural networks, circle Hough Transform, etc.) to determine centroid positions, boundaries, orientations, relative positions, distances, etc., for a patient's macula and optic disk (or cornea/sclera features in trans-scleral treatments) and the treatment commands can be updated so that the laser beam is scanned to a correct position of the patient's eye.

Figure 23:
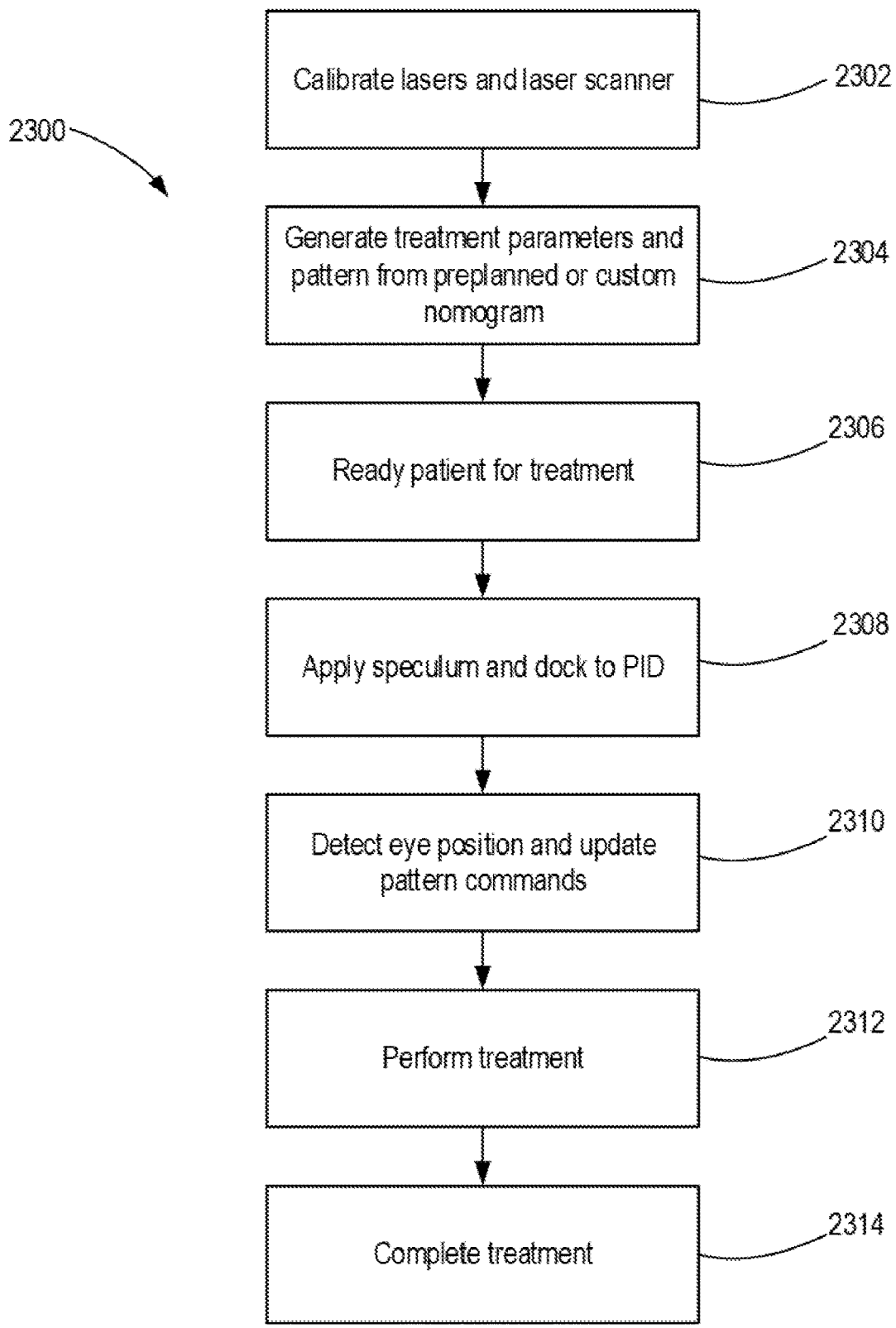
FIG. 23 is a flowchart of an example method of treatment.

Treatment or treatments can be performed using calibrated systems. For example, in a method 2300 shown in FIG. 23, laser power of the systems can be calibrated at 2302 using a detector to compare commanded peak and/or average powers to actual powers. The commanded locations for the laser beam delivery using the optical beam scanner and patient interface device can be compared to actual locations of beam delivery in one or more predetermined working planes or surfaces (e.g., that align with expected scleral or retinal surfaces) using spatial calibration devices, such as laser test surfaces and/or coordinate measuring machines or probes. At 2304, with a calibrated device, one or more sets of treatment pattern commands for a specific patient and corresponding to a pre-planned nomogram or a custom generated nomogram can be produced using software. At 2306, the patient is readied in a supine position for treatment, and anesthetic can be applied if appropriate, including by pre-instilling Thealose Duo drops (Thealose 3% API—Thea Pharma) for 10 minutes or longer, 2 drops per minute on the selected eye to receive treatment prior to anesthetic instillation. Topical proparacaine drops can be instilled when the treatment is ready to begin. At 2308, a speculum can be placed in the eye and a patient interface device can be centered on the cornea. Suction can be applied, and a cone of the speculum docked to the PID. At 2310, an eye position can be detected through the laser treatment system, and any changes to the treatment pattern that may improve accuracy, such as XY centration or annulus diameters or shapes, can be applied using software. The trans-scleral and/or trans-pupillary treatment can then proceed at 2312, and after completion at 2314, suction can be disengaged and the PID can be removed.

Figure 25:
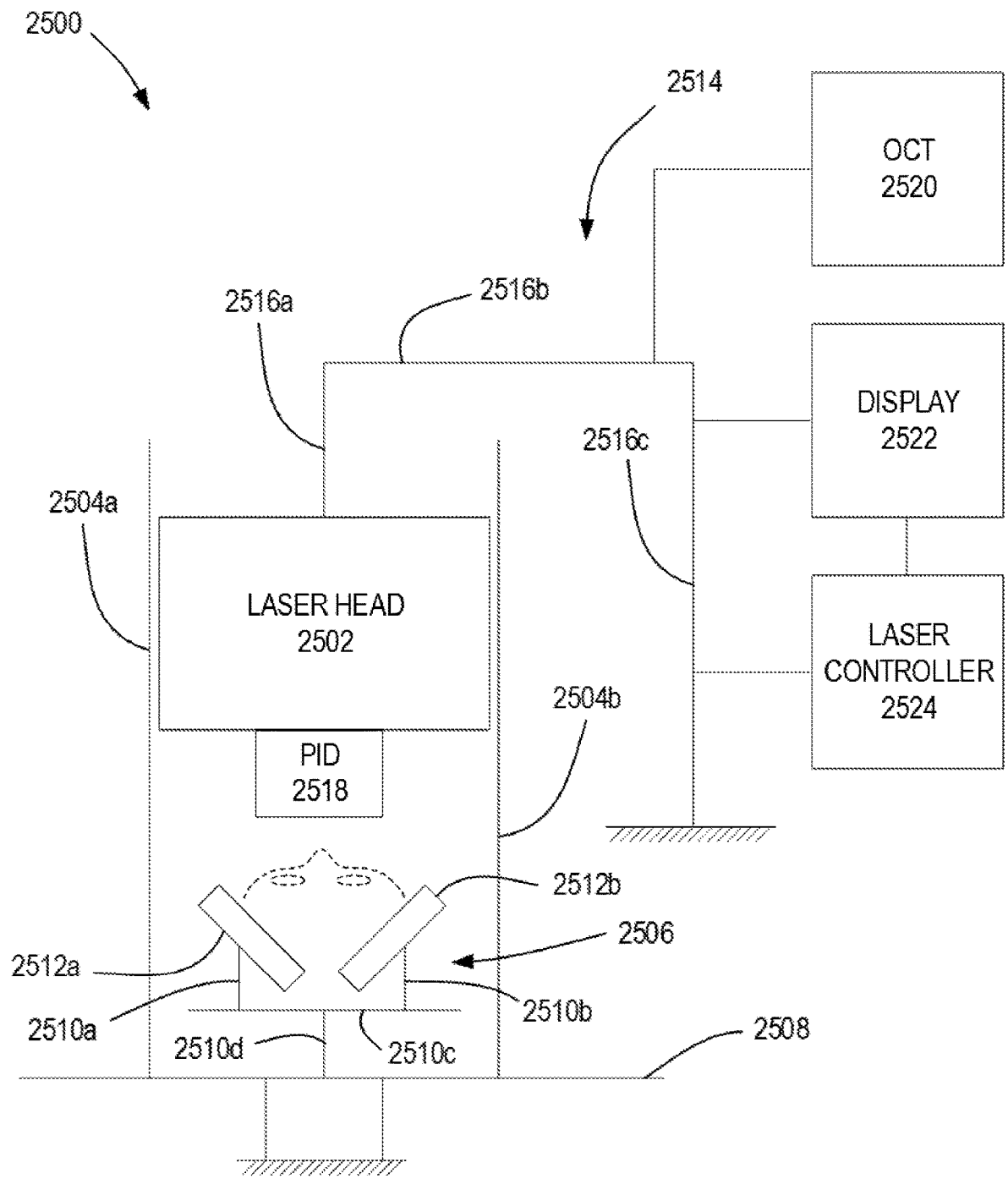
FIG. 25 is a schematic of an example laser treatment apparatus.

FIG. 25 shows an example laser treatment apparatus 2500 that can be used to deliver laser treatments in accordance with the various examples described herein. The apparatus 2500 includes a laser head 2502 slidably coupled to rails 2504a, 2504b so that the laser head 2502 can be fixed in a predetermined orientation in relation to a head rest 2506 and can slide towards the head rest 2506. The rails 2504a, 2504b are arranged in a fixed relation to the head rest 2506, though each can be adjustable, including relative to each other. For example, the rails 2504a, 2504b can be attached to a body support 2508, such as a recliner (e.g., a dental chair) having back and/or foot rests that can be reclined backwards and fine adjusted through electrical controls. The patient can also be positioned supine on a gurney. In additional examples, the patient can be upright with the view in FIG. 25 looking downwards onto the patient's head. The head rest 2506 can be firmly attached to, and adjustable relative to, the body support 2508, through one or more pivoted support members 2510a-2510d. The head rest 2506 can be configured as a horse-shoe shaped head rest that includes opposing adjustable pads 2512a, 2512b coupled to support members 2410a, 2510b. In representative examples, the head rest 2506 can be adjusted to accommodate different head sizes.

The laser head 2502 can be coupled to an end of an articulating support arm and stand 2514 that includes pivoted support members 2516a-2516c configured to allow movement and rotation of the laser head 2502, allowing the laser head 2502 to be brought in proximity to the body support 2508 and head rest 2506. In representative examples, the laser head 2502 can be removably coupled to the rails 2504a, 2504b so that the laser head 2502 can be secured and slidably translated along the rails 2504a, 2504b. Once mechanically mounted or 'clicked-in' to the rails 2504a, 2504b, the laser head 2502 can also be adjusted in various directions with internal movement stages for fine adjustments and to center optical components of the laser head 2502 in relation to a patient's eyes. In some examples, the attaching of the laser head 2502 to the rails 2504a, 2504b, a physician can be allowed to sit adjacent to the patient's head and control coupling of the laser head 2502 to the patient's eye or eyes through a patient interface device (PID) 2518 (such as the patient interface device 100 shown in FIGS. 5A-5C, by way of example). The PID 2518 can be affixed to the laser head 2502 and brought into contact with the patient's face and eye. The PID 2518 can include a liquid cooled suction ring configured to provide a coolant solution (such as PBS saline solution) to the cornea of the patient. The PID 2518 and laser head 2502 can be aligned with the patient's eyes with the patient's head resting in the head rest 2506. A foot pedal can be used by the physician for manual laser application, imaging controls, or mechanical adjustment.

The laser head 2502 typically includes a plurality of laser sources, such as two laser sources, three laser sources, four laser sources, or more, and a laser scanner, such as a 2-mirror galvo-scanner or two double-wedged prisms. In an example, the laser head 2502 includes a laser source configured to generate a laser beam at about 1470 nm, which can be used in trans-scleral treatments described herein, such as for lowering intraocular pressure or providing preventive treatments. In an example, the laser head 2502 further includes a laser source configured to generate a laser beam at about 810 nm, which can be used in trans-pupillary treatments described herein, such as for retinal neuroprotection applications. In some examples, the laser source at 810 nm (or another laser source) can generate a laser beam configured for standard glaucoma treatment modalities such as diode laser trabeculoplasty (DLT), micro pulse diode laser trabeculoplasty (MDLT) and Laser cyclophotocoagulation (LCP). In some examples, the laser head 2502 further includes a laser source configured to generate a laser beam at about 635 nm, which can be used for aiming and centering the other laser beams generated and scanned with the laser head 2502. The laser scanner of the laser head 2502 can be used to guide the one or more laser beams through the PID 2518 and/or contact lens coupled to the patient's eye. In typical examples, a fixed objective lens (such as an FO lens or other scan optic) is situated to receive the beam scanned to a selected position with the scan mirrors and to focus (or otherwise direct) the received beam to the targeted treatment locations. In some examples, a rotatable lens fixture can be provided so that alternative objectives (or no objective) can be coupled between the laser scanner and the PID 2518. In representative examples, each of the laser beams emitted from the laser sources can have a fixed spot size, though some examples can include a variable spot size, e.g., with an in-line beam expander or zoom lens. The laser beams typically have a uniform "top-hat" intensity profile, provided by suitable homogenizing optics, such as homogenizing waveguides and/or lens arrays.

The laser head 2502 can also include one or more imaging devices, such as a camera can be coupled through the PID 2518, e.g., through the laser scanner and/or objective lens, to image the eye of the patient. More complex imaging devices, such as an OCT apparatus 2520, can be stationed separated and coupled to the laser head 2502, e.g., along the support members 2516a-2516c, where there is insufficient form factor for housing in the laser head 2502. A display 2522 can be coupled to the stand 2514 to show images of the eye and/or provide a graphical user interface for control of the laser treatment. The display 2522 and laser head 2502 can be coupled to a laser controller 2524 (such as a PC or other computing device), which can include a processor and memory storing instructions to control laser treatment. As shown, the laser sources are situated in the laser head 2502 at the end of the support member 2516c, though in other examples, the laser sources can be coupled to the articulating support arm and stand 2514 at other positions and coupled along the support members 2516a-2516c through suitable waveguides, such as optical fibers. The physician can align the optics and laser beams emitted by the laser head 2502 through the PID 2518 with the patient's eyes by using an aiming beam, camera, and/imaging device. The laser controller 2524 can include an input interface configured with user controls to activate one or more treatment routines. For example, existing treatment patterns can be pre-loaded in the laser controller 2524 or additional routines, such as patient-specific ones, can be loaded from an external device.

Having described and illustrated the principles of the disclosed technology with reference to the illustrated embodiments, it will be recognized that the illustrated embodiments can be modified in arrangement and detail without departing from such principles. For instance, elements of the illustrated embodiments shown in software may be implemented in hardware and vice-versa. Also, the technologies from any example can be combined with the technologies described in any one or more of the other examples. It will be appreciated that procedures and functions such as those described with reference to the illustrated examples can be implemented in a single hardware or software module, or separate modules can be provided. The particular arrangements above are provided for convenient illustration, and other arrangements can be used.

In view of the many possible embodiments to which the principles of the disclosed technology may be applied, it should be recognized that the illustrated embodiments are only representative examples and should not be taken as limiting the scope of the disclosure. Alternatives specifically addressed in these sections are merely exemplary and do not constitute all possible alternatives to the embodiments described herein. For instance, various components of systems described herein may be combined in function and use. We therefore claim all that comes within the scope of the appended claims.

We claim:

1. An ab externo automated laser treatment system for treating an eye in a subject, comprising:

a non-contact laser source configured to generate a laser beam having at least one wavelength to treat the eye by directing the laser beam from a location spaced from the eye, wherein the at least one wavelength is a near-infrared 1.475 µm water-absorptive wavelength;

a laser scanner optically coupled to the non-contact laser source to receive the laser beam from the non-contact laser source and to scan the laser beam relative to the eye; and a processor and memory including stored computer-readable instructions that, responsive to execution by the processor, cause the laser treatment system to direct the laser beam to a plurality of perilimbal scleral treatment locations posterior to the corneolimbal junction to be irradiated in a predetermined treatment pattern on an external surface of the eye, wherein the trans-scleral treatment locations are 0-4 mm posterior to the corneolimbal junction such that the laser energy is absorbed in water-containing cells in the superficial sclera, creating a thermal elevation so that cell transduction cascades in the deeper ocular structures are affected, wherein directing the laser beam comprises repetitively directing the laser beam to the same irradiated scleral treatment locations on the surface of the eye at cyclic repetition intervals that induce protective thermal preconditioning and therapeutic bio-stimulation of one or more of the trabecular meshwork, the uveoscleral network and/or ciliary body without photocoagulation of the tissue of the eye,
wherein the laser parameters are configured to provide irradiance of the laser beam and a scanning speed with which the laser beam moves around the predetermined treatment pattern that are adapted to increase the temperature of the outer 200 μm scleral layers to the temperature of about 43-45° C.

2. The system of claim 1, wherein the memory includes stored computer readable instructions that cause the laser treatment system to direct the laser beam to a plurality of trans-pupillary treatment locations and to induce sublethal thermal elevations eliciting therapeutic biomodulation at the target eye tissue within a predetermined therapeutic temperature range, the plurality of trans-pupillary treatment locations including a predetermined curvilinear treatment pattern on target eye tissue of the eye comprising multiple concentric annuli on the macula around but not on the foveal avascular zone.

3. The system of claim 2, wherein each annulus on the macula of the curvilinear treatment pattern comprises a plurality of evenly-spaced and overlapping laser pulse spots sequentially delivered along a complete circle to produce an irradiated annular treatment zone within each annulus, wherein the laser pulse spots are delivered at a common scan speed for all macular annuli.

4. The system of claim 3, wherein the multiple concentric annuli comprise radially contiguous irradiated annular treatment zones on the macula.

5. The system of claim 2, wherein each concentric annulus has a width of between 400 μm and 600 μm.

6. The system of claim 2, wherein the annuli comprise three to five contiguous concentric annuli on the macula, each annulus having a substantially equal width, and wherein the plurality of scleral treatment locations comprises three concentric annuli on the sclera around the limbus at radii $R_1$, $R_2$ and $R_3$ that correspond respectively to locations overlying the primary aqueous outflow pathway, the pars plicata ciliary body, and the pars plana.

7. The system of claim 2, wherein the annuli comprise five contiguous annuli on the sclera, each annulus having a width of approximately 500 microns, and wherein the plurality of scleral treatment locations comprises three concentric annuli on the sclera at distances of approximately 1.5, 2.5 and 3.5 mm from the corneoscleral junction.

8. The system of claim 2, wherein the laser source comprises a first diode laser source operable to produce a pulsed laser beam at 810 nm for directing to the trans-pupillary treatment locations, a second diode laser source operable to produce a continuous-wave laser beam at 1475 nm for directing to the scleral treatment locations, and at least one beam splitter situated to receive and direct the beam at 810 nm and the beam at 1475 nm along a common optical path for receiving by the laser scanner.

9. The system of claim 1, wherein the memory includes stored computer-readable instructions that cause the laser treatment system to direct the laser beam to a plurality of trans-pupillary treatment locations and to induce sublethal thermal elevations eliciting therapeutic biomodulation at the target eye tissue within a predetermined therapeutic temperature range, the plurality of trans-pupillary treatment locations including an area (i) surrounding the macula, but not on the foveal avascular zone, and (ii) surrounding the optic disk, but not on the optic disk or adjacent peripapillary crescent.

10. The system of claim 1, wherein the memory includes stored computer-readable instructions that cause the laser treatment system to direct the laser beam to a plurality of trans-pupillary treatment locations and to induce sublethal thermal elevations eliciting therapeutic biomodulation at the target eye tissue within a predetermined therapeutic temperature range, the plurality of trans-pupillary treatment locations including an area surrounding the optic disk, but not on the optic disk or adjacent peripapillary crescent.

11. The system of claim 1, wherein the memory includes stored computer-readable instructions that cause the laser treatment system to direct the laser beam to a plurality of trans-pupillary treatment locations and to induce sublethal thermal elevations eliciting therapeutic biomodulation at the target eye tissue within a predetermined therapeutic temperature range, the plurality of transpupillary treatment locations including an area adjacent to the foveal avascular zone, but not on the area of the papillomacular bundle.

12. The system of claim 1, wherein the stored computer-readable instructions cause the laser treatment system to direct the laser beam to the plurality of scleral treatment locations at the intervals that induce the protective thermal preconditioning and bio-stimulation of targeted structures eliciting biomechanical and biochemical responses to lower intraocular pressure.

13. The system of claim 1, wherein the processor is configured with instructions to receive an input corresponding to a location of the corneolimbal junction or limbus of the subject and wherein the processor is configured to determine the plurality of scleral treatment locations in response to the input and wherein the plurality of scleral treatment locations is offset radially outward from the input location corresponding to corneolimbal junction or limbus to contour the treatment pattern to the anatomy of the eye of the subject.

14. The system of claim 1, wherein the scleral treatment locations are in a 360° annular pattern posterior to the corneolimbal junction, and the processor is configured to direct the laser beam to a set of pre-identified scleral treatment locations on the surface of the eye during a first treatment cycle, and during a subsequent treatment cycle direct the laser beam to the same pre-identified scleral treatment locations, to achieve precise cyclic thermal elevation of scleral tissue underlying the pre-identified scleral treatment locations at intervals of time with thermal relaxation of the irradiated tissue between treatment cycles.

15. The system of claim 14, wherein the processor is configured to set the speed of each treatment cycle to achieve the thermal relaxation by spacing irradiation of the scleral treatment locations at intervals such that an exposure time and relaxation time produce a targeted time-temperature history.

16. The system of claim 14, wherein the 360° pattern is interrupted nasally by 10-30° and temporally by 10-30°.

17. The system of claim 16, wherein the multiple annular treatment patterns target the
   (a) perilimbal outflow structure;
   (b) pars plicata; and
   (c) pars plana.

18. The system of claim 1, wherein the interval between irradiation of the same scleral treatment location produces a duty factor, corresponding to the ratio between the active exposure ON time/(active exposure+relaxation OFF time), in the 2-50% range.

19. The system of claim 18, wherein the interval between irradiation of the same scleral treatment location is about 10-300 ms.

20. The system of claim 19, wherein the interval between irradiation of the same scleral treatment location is about 100-200 ms.

21. The system of claim 1, wherein the predetermined treatment pattern is located about 1.5 mm posterior to the corneolimbal junction.

22. The system of claim 1, wherein the predetermined treatment pattern comprises multiple annular treatment patterns, and wherein the multiple annular treatment patterns are spaced about 1.5 mm, 2.5 mm and 3.5 mm posterior to the corneolimbal junction, wherein the annular treatment patterns comprise one or more of circular, oval, elliptical, egg-like, non-circular, non-elliptical, or asymmetrical patterns, or patterns that correspond to the shape of Schlemm's canal or the limbus.

23. The system of claim 1, further comprising a heat sink placed in contact with the eye over the scleral treatment locations to conduct heat away from the surface of the eye.

24. The system of claim 23, wherein the heat sink comprises a curved contact lens placed on the surface of the eye.

25. The system of claim 24, wherein the contact lens comprises a cooled contact lens that substantially conforms to the surface of the eye.

26. The system of claim 1, wherein the protective thermal preconditioning and therapeutic bio-stimulation are controlled by one or more of the laser's power, irradiance, scanning speed, cycle repetition rate, number of cycle repetitions, spot size and duty cycle.

27. The system of claim 1, wherein the processor is configured to direct the laser beam to the scleral treatment location in a spot having a diameter of 500-1000 µm.

28. The system of claim 27, wherein the spot has a diameter of about 600 µm.

29. The system of claim 1, wherein the system further comprises an optical imaging system for detecting the limbus and/or corneolimbal junction of the subject.

30. The system of claim 29, wherein the processor is configured to identify the predetermined scleral treatment locations at locations determined by the shape of the limbus and/or corneolimbal junction of the eye of the subject.

31. The system of claim 1, further comprising a patient interface for docking the non-contact laser source spaced away from the eye, the patient interface comprising a spacer that maintains the eye in a substantially fixed location for imaging and treatment, and the spacer maintains the non-contact laser source spaced from and not contacting the surface of the eye.

32. The system of claim 31, wherein the patient interface further comprises a speculum for placement between the eyelids of the subject to expose the eye to the laser beam.

33. The system of claim 31, wherein the patient interface further comprises a fixation ring for a contact lens, and the fixation ring comprises a resilient sealing face, wherein the system is configured to maintain negative pressure between the contact lens and the fixation ring to secure the patient interface to the surface of the eye and substantially immobilize the eye of the subject.

34. The system of claim 31, wherein the negative pressure is adjustable.

35. The system of claim 31, wherein the system is configured to cool the spacer and/or fixation ring and/or contact lens.

36. The system of claim 35, wherein the spacer and/or fixation ring comprise internal fluid flow channels, and the system is configured to introduce a cooled fluid through the fluid flow channels to cool the spacer and/or fixation ring and/or contact lens.

37. The system of claim 31, wherein the system further comprises a positioning arm for positioning the patient interface in a location relative to the surface of the eye of the subject.

38. The system of claim 1, wherein the laser source is configured to produce the laser beam with pulses at a pulse repetition period in the range of 1-3 ms, pulse repetition rate of 1000 to 333 pulses per second and a pulse duration in the range of 20-500 µs.

39. The system of claim 38, wherein the laser source is configured to produce the laser beam with pulses at a pulse repetition period in the range of 1.5-2.5 ms, pulse repetition rate of 666 to 400 pulses per second, and a pulse duration in the range of 50-150 µs.

40. The system of claim 38, wherein the laser source is configured to produce the laser beam with pulses at a pulse repetition period in the range of 1.8-2.2 ms, pulse repetition rate of 556 to 455 pulses per second, and a pulse duration in the range of 80-120 µs.

41. The system of claim 1, further comprising a detector optically coupled to the target eye tissue and wherein the stored computer-readable instructions cause the laser scanner to selectively direct the laser beam to the target eye location based on a change in a position of the target eye tissue detected with the detector.

* * * * *